(12) United States Patent
Moriconi et al.

(10) Patent No.: US 9,856,246 B2
(45) Date of Patent: Jan. 2, 2018

(54) TRPM8 ANTAGONISTS

(71) Applicant: Dompé farmaceutici S.p.A., Milan (IT)

(72) Inventors: Alessio Moriconi, L'Aquila (IT); Gianluca Bianchini, L'Aquila (IT); Sandro Colagioia, L'Aquila (IT); Laura Brandolini, L'Aquila (IT); Andrea Aramini, L'Aquila (IT); Chiara Liberati, Milan (IT); Silvia Bovolenta, Milan (IT)

(73) Assignee: Dompé farmaceutici S.p.A., Milan (IT)

(*) Notice: Subject to any disclaimer, the term of this patent is extended or adjusted under 35 U.S.C. 154(b) by 0 days.

(21) Appl. No.: 15/414,803

(22) Filed: Jan. 25, 2017

(65) Prior Publication Data

US 2017/0129881 A1 May 11, 2017

Related U.S. Application Data

(62) Division of application No. 14/366,796, filed as application No. PCT/EP2012/076147 on Dec. 19, 2012, now Pat. No. 9,585,875.

(30) Foreign Application Priority Data

Dec. 19, 2011 (EP) .................................... 11194365
Jul. 27, 2012 (EP) .................................... 12178327

(51) Int. Cl.

| | | |
|---|---|---|
| *C07D 417/12* | (2006.01) |
| *C07D 263/40* | (2006.01) |
| *C07D 413/04* | (2006.01) |
| *C07D 417/10* | (2006.01) |
| *C07D 277/56* | (2006.01) |
| *C07D 417/04* | (2006.01) |

(52) U.S. Cl.
CPC ......... *C07D 417/12* (2013.01); *C07D 263/40* (2013.01); *C07D 277/56* (2013.01); *C07D 413/04* (2013.01); *C07D 417/04* (2013.01); *C07D 417/10* (2013.01)

(58) Field of Classification Search
CPC .. C07D 417/12; C07D 263/40; C07D 413/04; C07D 417/10; C07D 277/56; C07D 417/04
See application file for complete search history.

(56) References Cited

U.S. PATENT DOCUMENTS

| | | | |
|---|---|---|---|
| 4,153,607 A | 5/1979 | Eilingsfeld | |
| 5,614,520 A * | 3/1997 | Kondo | A61K 31/425 514/236.8 |
| 2010/0160289 A1 | 6/2010 | Macielag | |
| 2014/0371276 A1 | 12/2014 | Moriconi | |

FOREIGN PATENT DOCUMENTS

| | | |
|---|---|---|
| EP | 1321463 A1 | 6/2003 |
| WO | WO2007089031 | 8/2007 |
| WO | WO2010125831 | 11/2010 |
| WO | WO2012036233 | 3/2012 |

OTHER PUBLICATIONS

Tsuge et al. Tetrahedron 1973, 29, 1983-1990.*
CAS Registry No. 190271-73-9, which entered STN on Jun. 24, 1997.*
CAS Registry No. 685541-90-6, which entered STN on May 25, 2004.*
Boyd, G.V., "Product Class 12: Oxazoles". Science of Synthesis 11.12, 383-479, 2002.
Dridi, K., et al., "Reaction of Mercaptoacetate and Halides Containing Activated Methylenes with Thiocarbamoylimidates: A Novel Approach to the Synthesis of Aminothiazole Derivatives." Synthetic Communications, 28(1), 167-174, 1998.
Hertzog D.L., et al., "The discovery and optimization of pyrimidinone-containing MCH R1 antagonists." ScienceDirect Bioorganic & Medicinal Chemistry Letters 16 (2006) 4723-4727.
Ilyin A.P., et al., "One-Step assembly of carbamoyl substituted annulated 1,4-oxazepines." Tetrahedron Letters 47 (2006) 2649-2653.
International Search Report and Written Opinion of the International Searching Authority for PCT/EP2012/076147, dated Jan. 30, 2013, 17 pages.
Kerdesky F.A.J., et al., "4-Hydroxythiazole Inhibitors of 5-Lipoxygenase." J. Med. Chem 1991, 34, 2158-2165.
Ronkin S.M., et al., "Discovery of pyrazolthiazoles as novel and potent inhibitors of bacterial gyrase." Bioorganic & Medicinal Chemistry Letters 20 (2010) 2828-2831, 4 pages.
Tsuge O. et al., "Studies of Acyl and Thioacyl Isocyanates—XII[1] The Reactions of Benzoyl and Thiobenzoyl Isocyanates with Sulfonium Ylides and with Diazoalkanes" Tetrahedron, vol. 29, 1983-1990, 1973.
Gaurav Mukerji et al, "Pain during ice water test distinguishes clinical bladder hypersensitivity from overactivity disorders", BMC Urology, Dec. 27, 2006, 6:31, 7 pages.

(Continued)

*Primary Examiner* — Matthew Coughlin
(74) *Attorney, Agent, or Firm* — Fish & Richardson P.C.

(57) ABSTRACT

The invention relates to compounds acting as selective antagonists of Transient Receptor Potential cation channel subfamily M member 8 (TRPM8), and having formula:

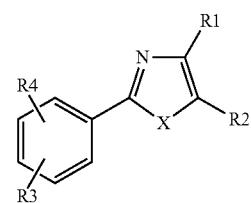

Figure 3:
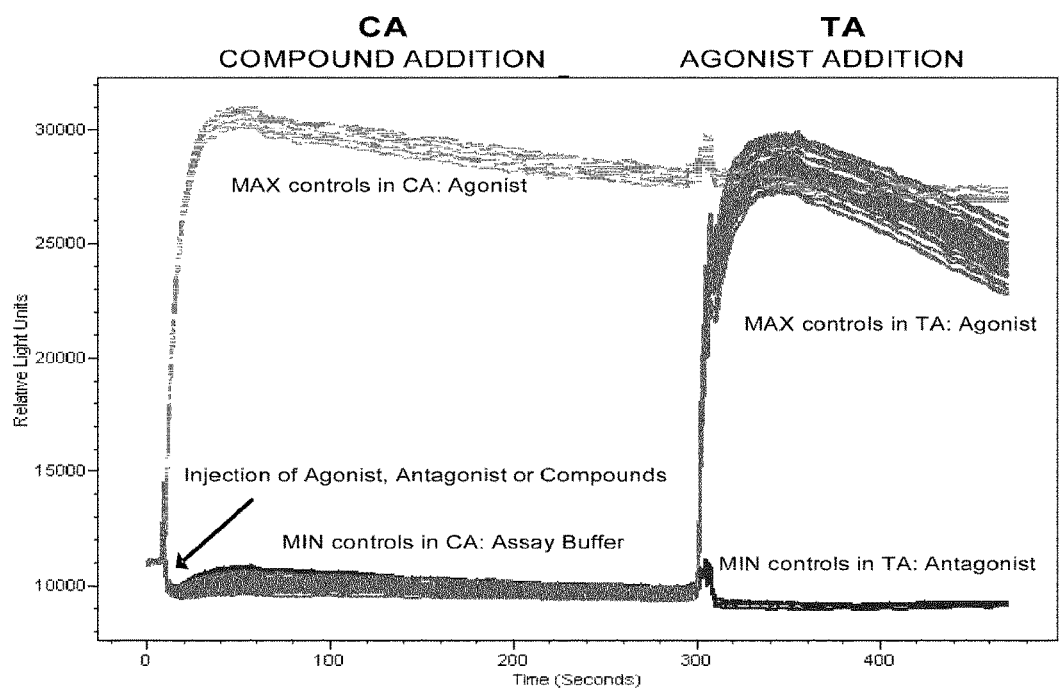

Said compounds are useful in the treatment of diseases associated with activity of TRPM8 such as pain, inflammation, ischaemia, neurodegeneration, stroke, psychiatric disorders, itch, irritable bowel diseases, cold induced and/or exacerbated respiratory disorders and urological disorders.

2 Claims, 3 Drawing Sheets

(56) References Cited

OTHER PUBLICATIONS

De Groat, "A Neurologic Basis for the Overactive Bladder," Urology, Dec. 1997, Issue 50(Supplement 6A), pp. 36-52.
Luciano De Petrocellis et al., "Regulation of transient receptor potential channels of melastatin type 8 (TRPM8): Effect of cAMP, cannabinoid $CB_1$ receptors and endovanilloids," Experimental Cell Research, May 2007 May, 313(9), pp. 1911-1920.
Massimo Lazzeri et al., "TRP family proteins in the lower urinary tract: translating basic science into new clinical prospective," Therapeutic Advances in Urology, Apr. 2009, 1(1), pp. 33-42.
David D. McKemy et al., "Identification of a cold receptor reveals a general role for TRP channels in thermosensation," Nature, vol. 416, Mar. 2002, pp. 52-58.
Bernd Nilius et al., "Gating of TRP channels: a voltage connection?" The Journal of Physiology, vol. 567, Issue 1, Aug. 2005, pp. 35-44.
Bernd Nilius et al., "Transient Receptor Potential Cation Channels in Disease," Physiol Rev., Jan. 2007, 87(1), pp. 165-217.
Bernd Nilius, "TRP Channels in disease," Biochimica et Biophysica Acta (BBA)—Molecular Basis of Disease, Aug. 2007, vol. 1772, Issue 8, pp. 805-1032.
Bernd Nilius et al., "TRP Channels in disease," Sci. STKE, Aug. 2005, vol. 2005, Issue 295, p. re8.
Andrea M. Peier et al., "A TRP Channel that Senses Cold Stimuli and Menthol," Cell, vol. 108, Mar. 2002, pp. 705-715.
Clare J. Proudfoot et al., Analgesia Mediated by the TRPM8 Cold Receptor in Chronic Neuropathic Pain, Current Biology 16, Aug. 22, 2006, pp. 1591-1605.
Tibor Rohacs, et al., "Pi(4,5)$P_2$ regulates the activation and desensitization of TRPM8 channels through the TRP domain," Nature Neuroscience, vol. 8, No. 5, May 2005, pp. 626-634.
Ulrich Wissenbach, "TRP channels as potential drug targets,", 2004.
Fabien Vanden Abeele, "Membrane Transport, Structure, Function and Biogenesis: Ca2+—independent Phospholipase A2—dependent Gating of TRPM8 by Lysophospholipids," The Journal of Biological Chemistry 281, Dec. 29, 2006, pp. 40174-40182.
Thomas Voets, "Sensing with TRP channels," Nature Chemical Biology, vol. 1, No. 2, Jul. 2005, pp. 85-92.
Wouter Everaerts, "On the Origin of Bladder Sensing: Tr(i)ps in Urology," Neurourology and Urodynamics 27, Apr. 2008, pp. 264-273.
Hong Xing et al., "TRPM8 mechanism of autonomic nerve response to cold in respiratory airway," Molecular Pain 2008, 4:22, Jun. 2008, 9 pages.
Roddy et al. Ann. Rheum. Dis. 2007, 66, 1374-1377.
Mayo clinic, Alzheimer's disease, obtained from http://www.mayoclinic.org/diseases-conditions/alzheimers-disease/manage/ptc-20167176 on Jan. 9, 2016.
NIH, National Heart, Lung, and Blood Institute, How Can Asthma be Prevented? Obtained from http://www.nhlbi.nih.gov/health/health-topics/topics/asthma/prevention on Jan. 9, 2016.
Harrison's Principles of Internal Medicine, 14th Edition, vol. 1, Aug. 1997, Chapter 322, pp. 1935-1940, Chapter 323, p. 1941, and Chapter 344, pp. 2161-2163.
Whittaker, "Understanding the difference between gout, osteoarthritis and rheumatoid arthritis," SA Pharmacist's Assistant, Winter 2012, pp. 6 and 7.
Australian Office Action for Application No. 2012357747, dated Sep. 16, 2016, 9 pages.
Hou, R.-S. et al, "Synthesis of 2-Phenylthiazoles from α-Tosyloxyketones and Thiobenzamide in [Bmim][PF6] Ionic Liquid at Ambient Temperature", Journal of the Chinese Chemical Society, 2006, vol. 53, pp. 863-866.
Ried, W. et al, "Thiazolsynthesen mit N-Cyanimidsaureestern oder 3-Cyanisoharnstoffen und Thioglycolsaurederivaten," Liebigs Annalen der Chemie, 1986, pp. 780-784.
CAS RN 1240618-16-9; STN entry date: Sep. 13, 20104-Ethoxy-2-phenyl-5-oxazolol, 1 page.
CAS RN 1240617-55-3; STN entry date: Sep. 13, 20104-Ethoxy-2-phenyl-5-oxazolecarboxamide, 1 page.
CAS RN 1240617-49-5; STN entry date: Sep. 13, 20104-Ethoxy-2-phenyl-5-oxazolecarbonitrile, 1 page.
CAS RN 1240614-78-1; STN entry date: Sep. 13, 20104-Amino-2-phenyl-5-oxazolol, 1 page.
CAS RN 1240614-44-1; STN entry date: Sep. 13, 20104-Amino-2-phenyl-5-oxazolecarboxylic acid, 1 page.
CAS RN 1240614-30-5; STN entry date: Sep. 13, 20104-Amino-2-phenyl-5-oxazolecarbonitrile, 1 page.
CAS RN 1240603-12-6; STN entry date: Sep. 13, 20104-Amino-2-phenyl-5-oxazolecarboxamide, 1 page.
CAS RN 1240597-62-9; STN entry date: Sep. 13, 20104-Ethoxy-2-phenyl-5-oxazolecarboxylic acid, 1 page.
CAS RN 263160-35-6; STN entry date: Apr. 26, 20004-[(2,6-Dichlorophenypmethoxy]-2-phenyl-5-thiazolecarboxylic acid, 1 page.
CAS RN 262856-07-5; STN entry date: Apr. 24, 20002-(2-chlorophenyl)-4-hydroxy-5-thiazolecarboxylic acid ethyl ester, 1 page.

\* cited by examiner

Figure 1

Figure 2

TRPM8 ANTAGONISTS

CROSS-REFERENCE TO RELATED APPLICATIONS

This application is a divisional application of U.S. application Ser. No. 14/366,796, filed Jun. 19, 2014, which is a National Stage under 35 U.S.C. §371 of International Application No. PCT/EP2012/076147, having an International Filing Date of Dec. 19, 2012, which claims the benefit of EP Application No. 11194365.0, filed Dec. 19, 2011 and EP Application No. 12178327.8, filed Jul. 27, 2012. These applications are hereby incorporated by reference in their entirety.

BRIEF DESCRIPTION OF THE INVENTION

The present invention relates to 2-aryl oxazole and thiazole derivatives that are useful for the prevention, reduction of the risk of, amelioration and/or treatment of diseases associated with the activity of the Transient Receptor Potential cation channel subfamily M member 8 (hereinafter TRPM8) also known as Cold Menthol Receptor 1 (CMR-1), and in particular for the prevention, reduction of the risk of, amelioration and/or treatment of itch, irritable bowel diseases, cold induced and/or exhacerbated respiratory disorders, ischaemia, pain, neurodegeneration, psychiatric disorders, stroke and urological disorders. The invention further relates to pharmaceutical compositions containing the above compounds.

BACKGROUND OF THE INVENTION

Transient Receptor Potential (TRP) channels are one of the largest group of ion channels and, based on their sequence homology, are classified into 6 sub-families (TRPV, TRPM; TRPA, TRPC, TRPP and TRPML). TRP channels are cation-selective channels activated by several physical (such as temperature, osmolarity and mechanical stimuli) and chemical stimuli. TRPM8, which was cloned in 2002, is a non-selective cation channel of the TRP family expressed on a subpopulation of somatic sensory nerves on dorsal root ganglion and trigeminal ganglia that causes sensory nerve excitation. It is activated by mild cold temperatures and synthetic cool-mimetic compounds such as menthol, eucalyptol and icilin [McKemy D. D. et al., *Nature* (2002) 416, 52-58; Peier A. M. et al. *Cell* (2002) 108, 705-715]. Like several other TRP channels, TRPM8 is also gated by voltage [Nilius B. et al., *J. Physiol.* (2005) 567, 35-44]. The voltage dependence of TRPM8 is characterized by a strong outward rectification at depolarized transmembrane potential and a rapid and potential-dependent closure at negative membrane potentials. Cooling agents and menthol application shifts the activation curve towards more negative potentials, increasing the possibility for the opening of the channel and boosting inward currents at physiological membrane potentials. Other endogenous factors, such as phospholipase $A_2$ products [Vanden Abeele F. et al., *J. Biol. Chem.* (2006) 281, 40174-40182], endocannabinoids [De Petrocellis L. et al., *Exp. Cell. Res.* (2007) 313, 1911-1920] and PIP2 [Rohacs T. et al., *Nat. Neurosci.* (2005) 8, 626-634] also participate in channel regulation.

There is a lot of direct and indirect evidence of a pivotal role of TRPM8 channel activity in diseases such as pain, ischemia and itch, irritable bowel diseases, cold induced and/or exhacerbated respiratory disorders. Further, it has been demonstrated that TRP channels transduce reflex signals that are involved in the overactive bladder of patients with damaged or abnormal spinal reflex pathways [De Groat W. C. et al., Urology (1997) 50, 36-52]. TRPM8 is activated by temperatures between 8° C. and 28° C. and expressed on the primary nociceptive neurons, including bladder urothelium, dorsal root ganglia, A-delta and C-fibers. The intravesical ice water or menthol also induce C-fiber mediated spinal micturition reflex in patients with urgency and urinary incontinence [Everaerts W. et al., Neurol. Urodyn. (2008) 27, 264-73].

Furthermore, TRPM8 is known to regulate $Ca^{2+}$ concentration influxes in response to cold temperature or pharmacological stimuli. Finally, in a recent paper, the potential role of TRPM8 in cold-induced asthma and in asthma exacerbation has been proposed, suggesting TRPM8 also a relevant target for the management of these pathologies [Xing H. et al., *Molecular Pain* (2008), 4, 22-30].

The expression of the channel in brain, lung, bladder, gastrointestinal tract, blood vessels, prostate and immune cells provide further possibility for therapeutic modulation of the activity of TRPM8 in a wide range of pathologies. In particular, the disorders or diseases that have been proven to be affected by the modulation of TRPM8 are pain such as chronic pain, neuropathic pain including cold allodynia and diabetic neuropathy, postoperative pain, osteoarthritic pain, rheumatoid arthritic pain, cancer pain, neuralgia, neuropathies, algesia, fibromyalgia, nerve injury, migraine, headaches; ischaemia, neurodegeneration, stroke, psychiatric disorders, including anxiety and depression, and itch, irritable bowel diseases, cold induced and/or exhacerbated respiratory disorders such as cold induced and/or exhacerbated pulmonary hypertension, asthma and COPD; urological disorders such as painful bladder syndrome, interstitial cystitis, detrusor overactivity (overactive bladder), urinary incontinence, neurogenic detrusor overactivity (detrusor hyperflexia), idiopathic detrusor overactivity (detrusor instability), benign prostatic hyperplasia, lower urinary tract disorders and lower urinary tract symptoms [Nilius B. et al. *Science STKE* (2005), 295, re8; Voets T. et al., *Nat. Chem. Biol.* (2005), 1, 85-92; Mukerji G. et al., *Urology* (2006), 6, 31-36; Lazzeri M. et al., *Ther. Adv. Urol.* (2009), 1, 33-42; Nilius B. et al., *Biochim. Biophys. Acta* (2007), 1772, 805-12; Wissenbach U. et al., *Biol. Cell.* (2004), 96, 47-54; Nilius B. et al., *Physiol. Rev.* (2007), 87, 165-217; Proudfoot C. J. et al., *Curr. Biol.* (2006), 16, 1591-1605].

Along the last few years, several classes of non peptide TRPM8 antagonists have been disclosed. WO 2006/040136, WO 2007/017092, WO 2007/017093, WO 2007/017094, and WO 2007/080109 describe benzyloxy derivatives as TRPM8 antagonists for the treatment of urological disorders; WO 2007/134107 describes phosphorous-bearing compounds as TRPM8 antagonists for the treatment of TRPM8-related disorders; WO 2009/012430 describes sulfonamides for the treatment of diseases associated with TRPM8; WO 2010/103381 describes the use of spirocyclic piperidine derivatives as TRPM8 modulators in prevention or treatment of TRPM8-related disorders or diseases; and, WO 2010/125831 describes sulfamoyl benzoic acid derivatives as modulators of the TRPM8 receptor and their use in the treatment of inflammatory, pain and urological disorders.

A therapeutic area in which there is a particularly high need for the development of antagonists of TRPM8 is that of urological-related disorders. In fact, traditional drugs and medications currently available for the treatment of urinary incontinence and disorders are characterized by several side effects. For example, at the moment, the therapy of overactive bladder syndrome is based on the use of drugs, especially anticholinergic agents that affect peripheral neural control mechanisms or bladder detrusor smooth muscle contraction. These drugs inhibit parasympathetic nerves exerting a direct spasmolytic effect on the muscle of the bladder. The result of this action is the decrease of intravesicular pressure, an increase in capacity and a reduction in the frequency of bladder contraction. However, the use of anticholinergic agents is associated with serious side effects, such as dry mouth, abnormal visions, constipation and CNS disturbances, that impair the overall patient compliance. The inadequacies of the actual therapies highlight the need for novel, efficacious and safe drugs with fewer side effects.

SUMMARY OF THE INVENTION

The aim of the present invention is to provide novel antagonists of TRPM8 with high selectivity for this specific receptor and an adequate pharmacokinetic profile for use in therapy.

The present inventors have now found a class of 2-aryl oxazole and thiazole compounds acting as selective antagonists of Transient Receptor Potential cation channel subfamily M member 8 (hereinafter referred to as TRPM8) and satisfying the above desiderata.

These compounds are useful in the treatment of pathologies associated with the activity of TRPM8.

DETAILED DESCRIPTION OF THE FIGURES

Figure 1:
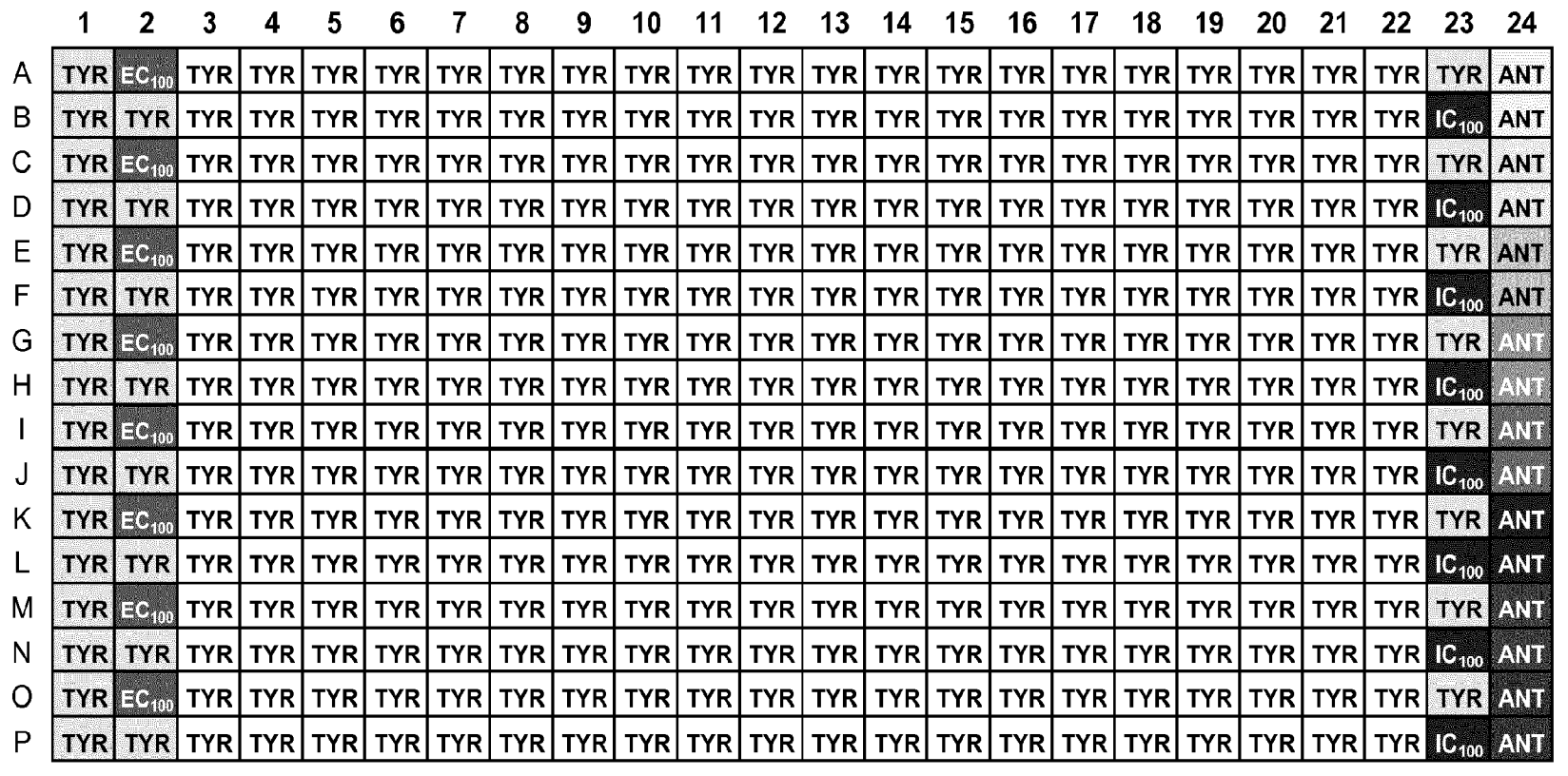

FIG. 1 shows a graphical representation of the 384 wells Compound Dilution Plate Layout used for the biological evaluation of the compounds of the invention as described in Example 119 wherein: in Column 1 wells contain assay buffer plus 0.5% DMSO; in Column 2: wells alternate Max signal control in first injection (Cooling agent 10 at 100 µM, corresponding to $EC_{100}$) and Min signal control in first injection (assay buffer plus 0.5% DMSO final); in columns 3-22: wells contain assay buffer plus 0.5% DMSO final and to each of these wells a compound to be tested is added, at 3× concentrations; in Column 23: wells alternate Max signal control in second injection (Assay Buffer) and Min signal control in second injection (Capsazepine at 50 mm, corresponding to $IC_{100}$); in Column 24: wells contain Capsazepine at 8 different concentrations in duplicate as reported in Example 119.

Figure 2:
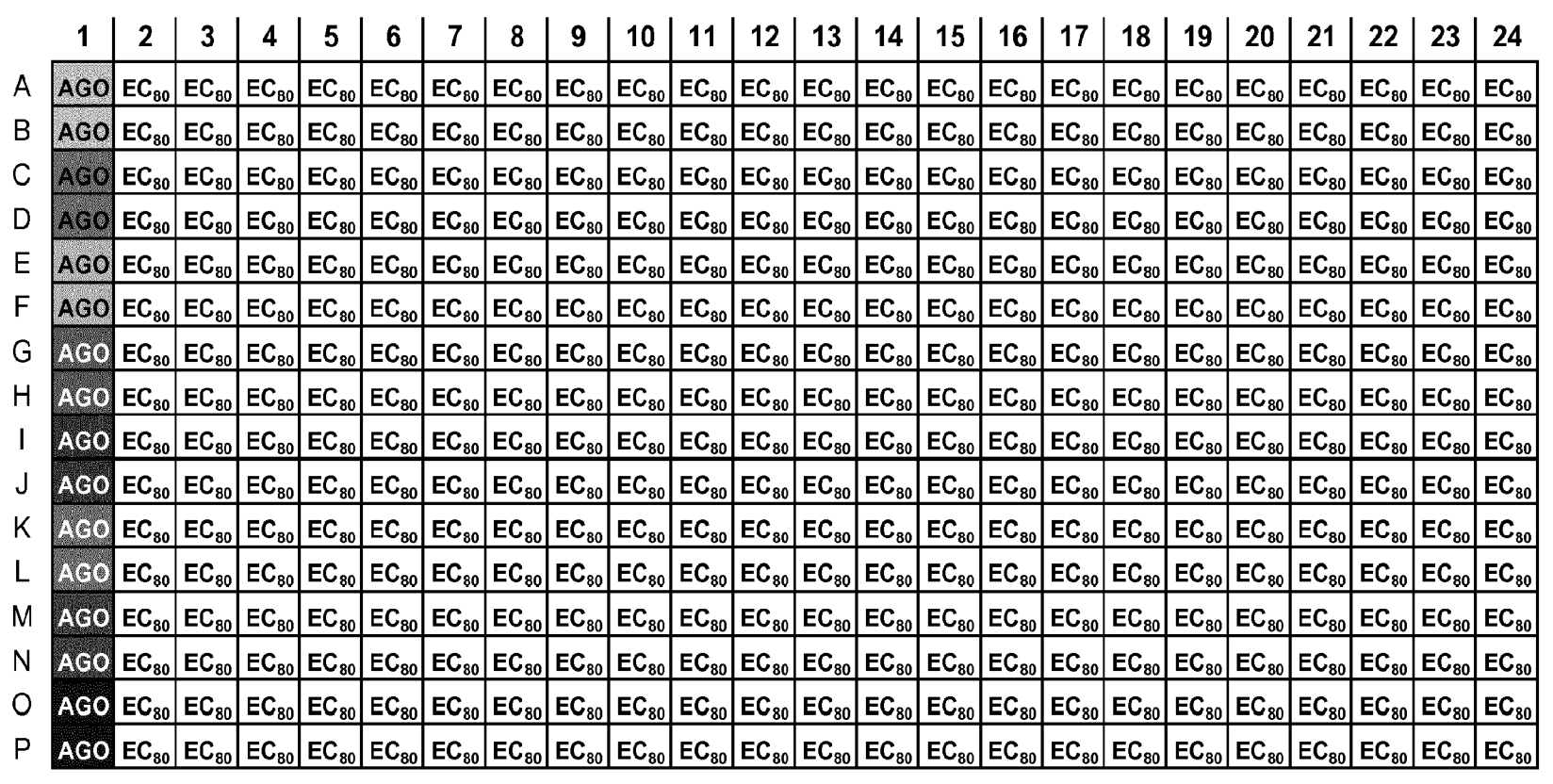

FIG. 2 shows a graphical representation of the 384 wells Activator Plate Layout used for the biological evaluation of the compounds of the invention as described in Example 119 wherein in Column 1 wells contain Cooling Agent 10 at 8 concentrations dose-response in duplicate at different concentrations as reported in Example 119; in Columns 2-24 wells contain Cooling Agent 10 at at $EC_{80}$ (3× concentrations, the highest being 20 µM final).

FIG. 3 shows a graph with a typical kinetic response obtained in the test described in Example 119(b) for the compounds of Table 1. Signal expressed as Relative Light Units (y-axis), is reported vs time (sec. (x-axis) following the injection of a definite amount of control/the test compounds. CA refers to the phase of Compound Addition, while TA to the Target Activation Phase performed in presence of the agonist, to increase the MAX Signal control, followed by the injection of a reference inhibitor for the complete abolition of the signal and the registration of the MIN Signal control.

Figure 4:
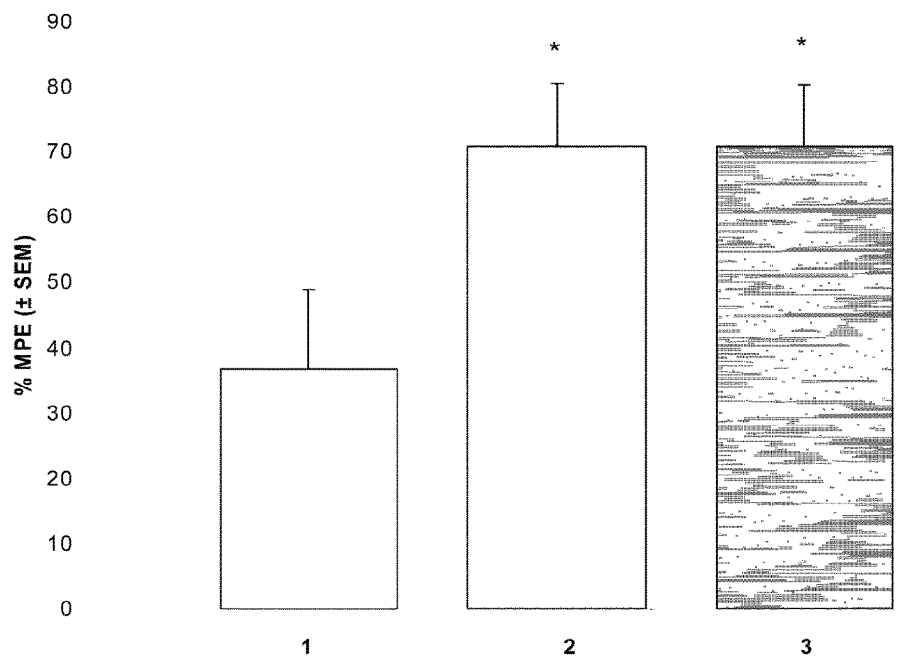

FIG. 4 shows the value of Maximum Possible Effect, measured as described in Example 120(b), observed after 2 hours from treatment with Control (1), Compound 10 (2) or Compound 45 (3).

DETAILED DESCRIPTION OF THE INVENTION

A first object of the present invention are compounds of formula (I):

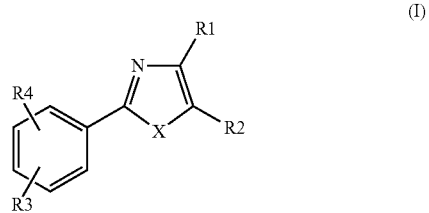

and pharmaceutically acceptable salts thereof,
wherein
X is selected from S or O;
$R_1$ is selected from the group consisting of:
—$OR_5$ wherein $R_5$ is selected from H; $C_1$-$C_4$ alkyl, trifluoromethanesulfonyl, benzyl, (trifluoromethyl)benzyl, (halo)benzyl, (trifluoromethyl)benzoyl, N-benzylcarbamoyl, cyclohexyloxyacetoyl substituted with at least one $C_1$-$C_3$ alkyl group, ($C_1$-$C_3$ alkoxy)methyl, $C_1$-$C_3$ alkanoyl and $CH_2CH_2NHR_6$, wherein
$R_6$ is selected from H and (furan-2-yl)methyl; and
—$NHR_7$ wherein $R_7$ is selected from H, tert-butoxycarbonyl, $C_1$-$C_3$ alkanoyl, (4-trifluoromethyl)benzoyl, N-phenylaminoacarbonyl, $CH_2R_8$, wherein
$R_8$ is selected from phenyl, benzo[d][1,3] dioxole, pyridin-3-yl, (pyrrolidin-1-yl)methyl, —$CH_2NHR_9$ wherein
$R_9$ is selected from H, $C_1$-$C_3$ alkyl and cycloalkyl;
$R_2$ is selected from the group consisting of
—$COOR_{10}$ wherein
$R_{10}$ is selected from H, $C_1$-$C_3$ alkyl and cyclohexyl, optionally substituted with at least one $C_1$-$C_3$ alkyl group;
—OH; —$CONH_2$; CN; -tetrazol-5-yl, 1-($C_1$-$C_3$ alkyl) tetrazol-5-yl, 2-($C_1$-$C_3$ alkyl)tetrazol-5-yl, 5-($C_1$-$C_3$ alkyl)1,2,4 triazol-3-yl, 5-($C_1$-$C_3$ alkyl) 1,2,4-oxadiazol-3yl, 5-($C_1$-$C_3$ alkyl) 1,3,4-oxadiazol-2-yl;
$R_3$ is selected from F or H,
$R_4$ is selected from H; $CH_3$; halogen; dimethylamino; pyridin-4yl; phenyl; 2- or 4-(halo)phenyl; 2- or 4-(trifluoromethyl)phenyl; 2- and/or 4-halobenzyloxy.

According to a preferred embodiment of the invention, in said compounds of formula I, $R_5$ may be selected from H, $C_1$-$C_4$ alkyl, trifluoromethanesulfonyl, benzyl, (trifluoromethyl)benzyl, (chloro)benzyl, (trifluoromethyl)benzoyl, N-benzylcarbamoyl, cyclohexyloxyacetoyl substituted with at least one $C_1$-$C_3$ alkyl group, (methoxy)methyl, propanoyl and $CH_2CH_2NHR_6$ wherein $R_6$ is as above. Particularly preferred among these compounds are compounds wherein $R_5$ is selected from H, methyl, isobutyl, trifluoromethanesulfonyl, benzyl, 4-(trifluoromethyl)benzyl, (chloro)benzyl, 4-(trifluoromethyl)benzoyl, N-benzylcarbamoyl, 2-isopropyl-5-methylcyclohexyloxyacetoyl, (methoxy)methyl, propanoyl and $CH_2CH_2NHR_6$ wherein $R_6$ is as above.

According to a further preferred embodiment of the invention, also in combination with any of the preceding embodiment, in said compounds of formula I $R_7$ may be selected from H, tert-butoxycarbonyl, acetyl, 4-(trifluoromethyl)benzoyl, N-phenylaminoacarbonyl, $CH_2R_8$, wherein R$_8$ is selected from phenyl, benzo[d][1,3] dioxole, pyridin-3-yl, (pyrrolidin-1-yl)methyl, —CH$_2$NHR$_9$
wherein
R$_9$ is selected from H, C$_1$-C$_3$ alkyl and cyclopentyl.

According to a further preferred embodiment of the invention, also in combination with any one of the preceding embodiments, in said compounds of formula I R$_{10}$ may be selected from H, C$_1$-C$_3$ alkyl and 2-isopropyl-5-cyclohexyl.

According to a further preferred embodiment of the invention, also in combination with any one of the preceding embodiments, in said compounds of formula I R$_4$ may be selected from H, CH$_3$, F, Cl, dimethylamino, preferably in position para, pyridin-4yl, phenyl, 2-F-penyl, 2-trifluoromethylphenyl and 2- or 4-halobenzyloxy, wherein said halo is preferably F or Cl.

According to a further preferred embodiment of the invention, in said compounds of formula I X is selected from S or O;
R$_1$ is selected from the group consisting of:
—OR$_5$ wherein R$_5$ is selected from H, C$_1$-C$_4$ alkyl, trifluoromethanesulfonyl, benzyl, (trifluoromethyl)benzyl, (chloro)benzyl, (trifluoromethyl)benzoyl, N-benzylcarbamoyl, cyclohexyloxyacetoyl substituted with at least one C$_1$-C$_3$ alkyl group, (methoxy)methyl, propanoyl and —CH$_2$CH$_2$NHR$_6$, wherein
R$_6$ is selected from H and (furan-2-yl)methyl
—NHR$_7$ wherein R$_7$ is selected from H, tert-butoxycarbonyl, acetyl, (4-trifluoromethyl)benzoyl, N-phenylaminocarbonyl, CH$_2$R$_8$, wherein
R$_8$ is selected from phenyl, benzo[d][1,3] dioxole, pyridin-3-yl, (pyrrolidin-1-yl)methyl, —CH$_2$NHR$_9$ wherein
R$_9$ is selected from H, C$_1$-C$_3$ alkyl and cyclopentyl
R$_2$ is selected from the group consisting of
—COOR$_{10}$ wherein
R$_{10}$ is selected from H, C$_1$-C$_3$ alkyl and 2-isopropyl-5-methylcyclohexyloxycarbonyl, —OH; —CONH$_2$; CN; tetrazol-5-yl or 1-(C$_1$-C$_3$ alkyl)tetrazol-5-yl; 2-(C$_1$-C$_3$ alkyl)tetrazol-5-yl; 5-(C$_1$-C$_3$ alkyl)1,2,4 triazol-3-yl; -5-(C$_1$-C$_3$ alkyl) 1,2,4-oxadiazol-3yl; -5-(C$_1$-C$_3$ alkyl) 1,3,4-oxadiazol-2-yl;
R$_3$ is selected from F or H,
R$_4$ is selected from H, F, CL, dimethylamino, preferably in position para, pyridin-4yl, phenyl, 2-F-penyl, 2-trifluoromethylphenyl, 2- and/or 4-F-benzyloxy.

Particularly preferred compounds of the invention are compounds of formula I wherein R$_1$ is selected from:
—OR$_5$, wherein R$_5$ is selected from H, benzyl, (chloro)benzyl, (trifluoromethyl)benzoyl, CH$_2$—CH$_2$NH$_2$; and
—NHCH$_2$CH$_2$R$_9$ wherein R$_9$ is selected from H and C$_1$-C$_3$ alkyl.

Particularly preferred among the compounds of the invention are also compounds of formula I wherein R$_2$ is selected from COOR$_{10}$ wherein R$_{10}$ is selected from H, C$_1$-C$_3$ alkyl.

Particularly preferred among the compounds of the invention are also compounds of formula I wherein R$_3$ is H.

Particularly preferred among the above compounds are those compounds of formula I wherein:
R$_1$ is selected from:
OR$_5$, wherein R$_5$ is selected from H, benzyl, (chloro)benzyl, (trifluoromethyl)benzoyl; and
CH$_2$—CH$_2$NH$_2$; and
NHCH$_2$CH$_2$R$_9$ wherein R$_9$ is selected from C$_1$-C$_3$ alkyl and H;
R$_2$ is COOR$_{10}$ wherein R$_{10}$ is selected from H, C$_1$-C$_3$ alkyl
R$_3$ is H.

According to a preferred embodiment of the invention, also in combination with any preceding embodiment, when X is S, in the above compounds of formula I when R$_1$ is OH and R$_2$ is COOH, R4 is different from Cl in meta position on the aromatic ring. According to another preferred embodiment of the invention, also in combination with any preceding embodiment, when R$_1$ is OH and R$_2$ is COOH or COOEt, R$_3$ and R$_4$ are not H at the same time. According to a further preferred embodiment of the invention, also in combination with any preceding embodiments, in said compounds of formula I when R$_3$ is F, R$_3$ is in position ortho of the aromatic ring and R$_4$ is F in position para of the aromatic ring, and when R$_3$ is H, R$_4$ is in position para or meta on the aromatic ring.

According to a further preferred embodiment of the invention, the compounds of formula I are selected from:
2-(4-chlorophenyl)-4-hydroxy-1,3-thiazole-5-carboxylic acid (compound n. 1)
4-hydroxy-2-(4-methylphenyl)-1,3-thiazole-5-carboxylic acid (compound n. 2)
2-(3-fluorophenyl)-4-hydroxy-1,3-thiazole-5-carboxylic acid (compound n. 3)
2-(4-fluorophenyl)-4-hydroxy-1,3-thiazole-5-carboxylic acid (compound n. 4)
methyl 4-hydroxy-2-phenyl-1,3-thiazole-5-carboxylate (compound n. 5)
methyl 2-(2,4-difluorophenyl)-4-hydroxy-1,3-thiazole-5-carboxylate (compound n. 6)
ethyl 4-hydroxy-2-phenyl-1,3-thiazole-5-carboxylate (compound n. 7)
ethyl 2-(4-chlorophenyl)-4-hydroxy-1,3-thiazole-5-carboxylate (compound n. 8)
ethyl 4-hydroxy-2-(4-methylphenyl)-1,3-thiazole-5-carboxylate (compound n. 9)
ethyl 2-(3-fluorophenyl)-4-hydroxy-1,3-thiazole-5-carboxylate (compound n. 10)
ethyl 2-(4-fluorophenyl)-4-hydroxy-1,3-thiazole-5-carboxylate (compound n. 11)
ethyl-4-hydroxy-2-(4-pyridin-4-yl)phenyl-1,3-thiazole-5-carboxylate (compound n. 12)
ethyl 2-[4-(dimethylamino)phenyl]-4-hydroxy-1,3-thiazole-5-carboxylate (compound n. 13)
ethyl 2-(3-chlorophenyl)-4-hydroxy-1,3-thiazole-5-carboxylate (compound n. 14)
ethyl 4-hydroxy-2-[2'-(trifluoromethyl)biphenyl-3-yl]-1,3-thiazole-5-carboxylate (compound n. 15)
ethyl 2-(2'-fluorobiphenyl-3-yl)-4-hydroxy-1,3-thiazole-5-carboxylate (compound n. 16)
ethyl 4-hydroxy-2-[2'-(trifluoromethyl)biphenyl-4-yl]-1,3-thiazole-5-carboxylate (compound n. 17)
ethyl 2-(2'-fluorobiphenyl-4-yl)-4-hydroxy-1,3-thiazole-5-carboxylate (compound n. 18)
ethyl 2-{4-[(2-fluorobenzyl)oxy]phenyl}-4-hydroxy-1,3-thiazole-5-carboxylate (compound n. 19)
ethyl 2-{4-[(4-fluorobenzyl)oxy]phenyl}-4-hydroxy-1,3-thiazole-5-carboxylate (compound n. 20)
ethyl 2-(4-fluorophenyl)-4-{[(trifluoromethyl)sulfonyl]oxy}-1,3-thiazole-5-carboxylate (compound n. 21)
ethyl 4-methoxy-2-(4-methylphenyl)-1,3-thiazole-5-carboxylate (compound n. 22)
ethyl 2-(4-methylphenyl)-4-(2-methylpropoxy)-1,3-thiazole-5-carboxylate (compound n. 23)
ethyl 4-(benzyloxy)-2-phenyl-1,3-thiazole-5-carboxylate (compound n. 24)
ethyl 4-[(3-chlorobenzyl)oxy]-2-(4-chlorophenyl)-1,3-thiazole-5-carboxylate (compound n. 25)

ethyl 4-[(3-chlorobenzyl)oxy]-2-(3-fluorophenyl)-1,3-thiazole-5-carboxylate (compound n. 26)
ethyl 4-[(4-chlorobenzyl)oxy]-2-phenyl-1,3-thiazole-5-carboxylate (compound n. 27)
ethyl 4-[(4-chlorobenzyl)oxy]-2-(3-chlorophenyl)-1,3-thiazole-5-carboxylate (compound n. 28)
ethyl 4-[(4-chlorobenzyl)oxy]-2-(4-methylphenyl)-1,3-thiazole-5-carboxylate (compound n. 29)
ethyl 4-[(4-chlorobenzyl)oxy]-2-(3-fluorophenyl)-1,3-thiazole-5-carboxylate (compound n. 30)
ethyl 4-[(2-chlorobenzyl)oxy]-2-phenyl-1,3-thiazole-5-carboxylate (compound n. 31)
ethyl 4-[(2-chlorobenzyl)oxy]-2-(4-fluorophenyl)-1,3-thiazole-5-carboxylate (compound n. 32)
ethyl 4-[(2-chlorobenzyl)oxy]-2-(4-chlorophenyl)-1,3-thiazole-5-carboxylate (compound n. 33)
ethyl 4-[(2-chlorobenzyl)oxy]-2-(3-chlorophenyl)-1,3-thiazole-5-carboxylate (compound n. 34)
ethyl 4-[(2-chlorobenzyl)oxy]-2-(4-methylphenyl)-1,3-thiazole-5-carboxylate (compound n. 35)
ethyl 2-phenyl-4-{[4-(trifluoromethyl)benzoyl]oxy}-1,3-thiazole-5-carboxylate (compound n. 36)
ethyl 2-(3-fluorophenyl)-4-{[4-(trifluoromethyl)benzoyl]oxy}-1,3-thiazole-5-carboxylate (compound n. 37)
ethyl 2-(4-methylphenyl)-4-{[4-(trifluoromethyl)benzoyl]oxy}-1,3-thiazole-5-carboxylate (compound n. 38)
ethyl4-(2-((1R,2S,5R)-2-isopropyl-5-methylcyclohexyloxy)acetoyloxy)-2-(4-methylphenyl)-1,3-thiazole-5-carboxylate (compound n. 39)
ethyl 4-[(benzylcarbamoyl)oxy]-2-(4-chlorophenyl)-1,3-thiazole-5-carboxylate (compound n. 40)
ethyl 4-(2-aminoethoxy)-2-(4-chlorophenyl)-1,3-thiazole-5-carboxylate (compound n. 41)
ethyl 2-(4-chlorophenyl)-4-{2-[(furan-2-ylmethyl)amino]ethoxy}-1,3-thiazole-5-carboxylate (compound n. 42)
4-[(4-chlorobenzyl)oxy]-2-(4-methylphenyl)-1,3-thiazole-5-carboxylic acid (compound n. 43)
4-[(4-chlorobenzyl)oxy]-2-phenyl-1,3-thiazole-5-carboxylic acid (compound n. 44)
4-[(4-chlorobenzyl)oxy]-2-(4-chlorophenyl)-1,3-thiazole-5-carboxylic acid (compound n. 45)
4-[(4-chlorobenzypoxy]-2-(3-chlorophenyl)-1,3-thiazole-5-carboxylic acid (compound n. 46)
4-(benzyloxy)-2-phenyl-1,3-thiazole-5-carboxylic acid (compound n. 47)
4-[(3-chlorobenzyl)oxy]-2-(3-fluorophenyl)-1,3-thiazole-5-carboxylic acid (compound n. 48)
4-[(2-chlorobenzyl)oxy]-2-phenyl-1,3-thiazole-5-carboxylic acid (compound n. 49)
4-[(2-chlorobenzyl)oxy]-2-(4-fluorophenyl)-1,3-thiazole-5-carboxylic acid (compound n. 50)
4-[(2-chlorobenzyl)oxy]-2-(4-chlorophenyl)-1,3-thiazole-5-carboxylic acid (compound n. 51)
4-[(2-chlorobenzyl)oxy]-2-(3-chlorophenyl)-1,3-thiazole-5-carboxylic acid (compound n. 52)
4-[(2-chlorobenzyl)oxy]-2-(4-methylphenyl)-1,3-thiazole-5-carboxylic acid (compound n. 53)
4-[(2-chlorobenzyl)oxy]-2-(3-fluorophenyl)-1,3-thiazole-5-carboxylic acid (compound n. 54)
2-phenyl-4-{[4-(trifluoromethyl)benzyl]oxy}-1,3-thiazole-5-carboxylic acid (compound n. 55)
2-(3-fluorophenyl)-4-{[4-(trifluoromethyl)benzyl]oxy}-1,3-thiazole-5-carboxylic acid (compound n. 56)
2-phenyl-4-{[4-(trifluoromethyl)benzoyl]oxy}-1,3-thiazole-5-carboxylic acid (compound n. 57)
2-(3-fluorophenyl)-4-{[4-(trifluoromethyl)benzoyl]oxy}-1,3-thiazole-5-carboxylic acid (compound n. 58)
2-(4-methylphenyl)-4-{[4-(trifluoromethyl)benzoyl]oxy}-1,3-thiazole-5-carboxylic acid (compound n. 59)
4-methoxy-2-(4-methylphenyl)-1,3-thiazole-5-carboxylic acid (compound n. 60)
2-(4-methylphenyl)-4-(2-methylpropoxy)-1,3-thiazole-5-carboxylic acid (compound n. 61)
ethyl 4-[(tert-butoxycarbonyl)amino]-2-(4-fluorophenyl)-1,3-thiazole-5-carboxylate (compound n. 62)
ethyl 4-amino-2-(4-fluorophenyl)-1,3-thiazole-5-carboxylate hydrochloride (compound n. 63)
ethyl 4-(acetylamino)-2-(4-methylphenyl)-1,3-thiazole-5-carboxylate (compound n. 64)
ethyl 2-(4-methylphenyl)-4-{[4-(trifluoromethyl)benzoyl]amino}-1,3-thiazole-5-carboxylate (compound n. 65)
ethyl 2-(4-methylphenyl)-4-[(phenylcarbamoyl)amino]-1,3-thiazole-5-carboxylate (compound n. 66)
ethyl 4-[(2-aminoethyl)amino]-2-(4-methylphenyl)-1,3-thiazole-5-carboxylate (compound n. 67)
ethyl 2-(4-chlorophenyl)-4-{[2-(methylamino)ethyl]amino}-1,3-thiazole-5-carboxylate (compound n. 68)
ethyl 2-(4-chlorophenyl)-4-{[2-(propylamino)ethyl]amino}-1,3-thiazole-5-carboxylate (compound n. 69)
ethyl 4-[(2-aminoethyl)amino]-2-(4-chlorophenyl)-1,3-thiazole-5-carboxylate (compound n. 70)
ethyl 4-{[2-(methylamino)ethyl]amino}-2-(4-methylphenyl)-1,3-thiazole-5-carboxylate (compound n. 71)
ethyl 4-[(2-aminoethyl)amino]-2-[2'-(trifluoromethyl)biphenyl-4-yl]-1,3-thiazole-5-carboxylate (compound n. 72)
ethyl 4-[(2-aminoethyl)amino]-2-[2'-(trifluoromethyl)biphenyl-3-yl]-1,3-thiazole-5-carboxylate (compound n. 73)
ethyl 2-(4-chlorophenyl)-4-{[2-(cyclopentylamino)ethyl]amino}-1,3-thiazole-5-carboxylate (compound n. 74)
ethyl 2-phenyl-4-{[2-(pyrrolidin-1-yl)ethyl]amino}-1,3-thiazole-5-carboxylate (compound n. 75)
ethyl 4-(benzylamino)-2-(3-fluorophenyl)-1,3-thiazole-5-carboxylate (compound n. 76)
ethyl 4-[(1,3-benzodioxol-5-ylmethyl)amino]-2-(3-fluorophenyl)-1,3-thiazole-5-carboxylate (compound n. 77)
ethyl 2-(3-fluorophenyl)-4-[(pyridin-3-ylmethyl)amino]-1,3-thiazole-5-carboxylate (compound n. 78)
4-[(2-aminoethyl)amino]-2-(4-methylphenyl)-1,3-thiazole-5-carboxylic acid (compound n. 79)
4-{[2-(methylamino)ethyl]amino}-2-(4-methylphenyl)-1,3-thiazole-5-carboxylic acid (compound n. 80)
4-[(2-aminoethyl)amino]-2-(3-fluorophenyl)-1,3-thiazole-5-carboxylic acid (compound n. 81)
sodium 4-[(3-chlorobenzyl)oxy]-2-(3-fluorophenyl)-1,3-thiazole-5-carboxylate (compound n. 82)
sodium 4-[(4-chlorobenzyl)oxy]-2-(4-methylphenyl)-1,3-thiazole-5-carboxylate (compound n. 83)
sodium 4-(4-chlorobenzyloxy)-2-(4-chlorophenyl)-1,3-thiazole-5-carboxylate (compound n. 84)
sodium 4-(2-chlorobenzyloxy)-2-(4-chlorophenyl)-1,3-thiazole-5-carboxylate (compound n. 85)
sodium 4-(2-chlorobenzyloxy)-2-(4-methylphenyl)-1,3-thiazole-5-carboxylate (compound n. 86)
sodium 4-(2-chlorobenzyloxy)-2-(3-fluorophenyl)-1,3-thiazole-5-carboxylate (compound n. 87)
sodium 4-(4-chlorobenzyloxy)-2-(3-fluorophenyl)-1,3-thiazole-5-carboxylate (compound n. 88)
(1R,2S,5R)-2-isopropyl-5-methylcyclohexyl-4-(benzyloxy)-2-(4-methylphenyl)-1,3-thiazole-5-carboxylate (compound n. 89)

(1R,2S,5R)-2-isopropyl-5-methylcyclohexyl-4-hydroxy-2-(4-methylphenyl)-1,3-thiazole-5-carboxylate (compound n. 90)

ethyl 2-(4-chlorophenyl)-4-(methoxymethoxy)-1,3-thiazole-5-carboxylate (compound n. 91)

2-(4-chlorophenyl)-4-(methoxymethoxy)-1,3-thiazole-5-carboxylic acid (compound n. 92)

2-(4-chlorophenyl)-4-(methoxymethoxy)-1,3-thiazole-5-carboxamide (compound n. 93)

2-(4-chlorophenyl)-4-(methoxymethoxy)-1,3-thiazole-5-carbonitrile (compound n. 94)

2-(4-chlorophenyl)-5-(1H-tetrazol-5-yl)-1,3-thiazol-4-ol (compound n. 95)

2-(4-chlorophenyl)-5-(1-methyl-1H-tetrazol-5-yl)-1,3-thiazol-4-ol (compound n. 96)

2-(3-fluorophenyl)-5-(1-methyl-1H-tetrazol-5-yl)-1,3-thiazol-4-ol (compound n. 97)

2-(4-chlorophenyl)-5-(5-methyl-4H-1,2,4-triazol-3-yl)-1,3-thiazol-4-ol (compound n. 98)

2-(3-fluorophenyl)-5-(5-methyl-4H-1,2,4-triazol-3-yl)-1,3-thiazol-4-ol (compound n. 99)

2-(4-chlorophenyl)-5-(5-methyl-1,2,4-oxadiazol-3-yl)-1,3-thiazol-4-ol (compound n. 100)

2-(3-fluorophenyl)-5-(5-methyl-1,2,4-oxadiazol-3-yl)-1,3-thiazol-4-ol (compound n. 101)

3-{4-[(4-chlorobenzyl)oxy]-2-(3-fluorophenyl)-1,3-thiazol-5-yl}-5-methyl-1,2,4-oxadiazole (compound n. 102)

2-(4-chlorophenyl)-5-(5-methyl-1,3,4-oxadiazol-2-yl)-1,3-thiazol-4-ol (compound n. 103)

2-(3-fluorophenyl)-5-(5-methyl-1,3,4-oxadiazol-2-yl)-1,3-thiazol-4-ol (compound n. 104)

ethyl 4-hydroxy-2-phenyl-1,3-oxazole-5-carboxylate (compound n. 105)

ethyl 2-(3-fluorophenyl)-4-hydroxy-1,3-oxazole-5-carboxylate (compound n. 106)

ethyl 4-hydroxy-2-(4-methylphenyl)-1,3-oxazole-5-carboxylate (compound n. 107)

ethyl 4-[(4-chlorobenzyl)oxy]-2-phenyl-1,3-oxazole-5-carboxylate (compound n. 108)

ethyl 4-[(4-chlorobenzyl)oxy]-2-(3-fluorophenyl)-1,3-oxazole-5-carboxylate (compound n. 109)

ethyl 4-[(4-chlorobenzyl)oxy]-2-(4-methylphenyl)-1,3-oxazole-5-carboxylate (compound n. 110)

ethyl 2-phenyl-4-{[4-(trifluoromethyl)benzoyl]oxy}-1,3-oxazole-5-carboxylate (compound n. 111)

4-[(4-chlorobenzyl)oxy]-2-phenyl-1,3-oxazole-5-carboxylic acid (compound n. 112)

4-[(4-chlorobenzyl)oxy]-2-(3-fluorophenyl)-1,3-oxazole-5-carboxylic acid (compound n. 113)

4-[(4-chlorobenzyl)oxy]-2-(4-methylphenyl)-1,3-oxazole-5-carboxylic acid (compound n. 114)

2-(3-fluorophenyl)-5-(5-methyl-1,2,4-oxadiazol-3-yl)-1,3-oxazol-4-ol (compound n. 115)

3-{4-[(4-chlorobenzyl)oxy]-2-(3-fluorophenyl)-1,3-oxazol-5-yl}-5-methyl-1,2,4-oxadiazole (compound n. 116)

ethyl 2-(3-fluorophenyl)-5-hydroxy-1,3-thiazole-4-carboxylate (compound n. 117).

2-(3-fluorophenyl)-5-(2-ethyl-2H-tetrazol-5-yl)-1,3-thiazol-4-ol (compound n. 118)

As it will be described in details in Example 119, the present inventors have found that the above compounds 1-118 are potent antagonists of TRPM8.

In details, all of the above compounds have been tested in a high-throughput screening (HTS) cellular-based assay for the human TRPM8 and have shown an antagonist activity with a $IC_{50}$ below 30 µM. Compounds 10, 45 and 118 have also been tested in a calcium influx assay, which has confirmed the antagonist activity of the tested compounds.

Thus, a second object of the present invention are the above compounds of formula (I) for use as antagonists of TRPM8, preferably of human TRPM8.

In order to obtain confirmation of the data obtained in vitro compounds 10, 45 and 118 have also been tested in two in vivo models.

In details, as will be described in Example 120 and 121 compounds 10 and 45 have been tested in an isovolumetric bladder model, an animal model for the evaluation of drugs active on pain induced by contractions of bladder, and compounds 10, 45 and 118 in a Chronic Constriction Injury of sciatic nerve (CCI), an animal model of neuropathic pain.

In the first model, the compounds showed significant efficacy in inhibiting rhythmic bladder contractions and micturition frequency. Moreover, both the compounds did not change Amplitude of Micturition (AM) when compared to basal values, suggesting that they are selective for the afferent arm of micturition reflex with no effect on the efferent pathway.

In the second model, the tested compounds showed a significant antiallodynic activity both in mechanical and cold allodynia.

As will be demonstrated in Example 122, the compounds of the invention show a high selectivity for TRPM8 and are thus devoid of side effects due to interference with other ion channels and GPCRs. In fact, both 10, 45 and 118 have been demonstrated to be selective in a wide range of ion channel and GPCRs.

Furthermore, as shown in Example 123 the compounds of the invention have an optimal pharmacokinetic profile.

Thus, the compounds of the invention are particularly suitable to be used in therapy.

Accordingly, a third object of the present invention are the above compounds for use as medicaments.

A fourth object of the present invention are the above compounds for use in the prevention, reduction of the risk of, amelioration and/or treatment of a disease associated with activity of TRPM8.

According to the present invention, by "disease that is associated with activity of TRPM8" it is preferably meant a disease selected from pain, itch, irritable bowel diseases, cold induced and/or exhacerbated respiratory disorders, ischaemia, neurodegeneration, stroke, urological disorders, and psychiatric disorders.

Preferably, said pain is selected from chronic pain, cancer pain, neuropathic pain, which is meant to include cold allodynia and diabetic neuropathy, postoperative pain, osteoarthritic pain, rheumatoid arthritic pain, neuralgia, neuropathies, fibromyalgia, algesia, nerve injury, migraine, headaches.

Preferably, said cold-induced and/or exhacerbated respiratory disorder is selected from cold-induced and/or exhacerbated pulmonary hypertension, COPD and asthma.

Preferably, said urological disorders are selected from painful bladder syndrome, interstitial cystitis, detrusor overactivity (also known as overactive bladder), urinary incontinence, neurogenic detrusor overactivity (also known as detrusor hyperflexia), idiopathic detrusor overactivity (also known as detrusor instability), benign prostatic hyperplasia, lower urinary tract disorders and lower urinary tract symptoms.

Preferably, said psychiatric disorders are selected from anxiety and depression.

A fifth object of the present invention are pharmaceutical compositions comprising the at least one of the above said compounds of formula I in combination with pharmaceutically acceptable excipients and/or diluents.

According to a preferred embodiments said pharmaceutical composition is for the prevention, reduction of the risk of, amelioration and/or treatment of a disease associated with activity of TRPM8.

According to an embodiment, said pharmaceutical composition contains at least one of the above compounds of formula I as the sole active principle(s). According to an alternative embodiment, said pharmaceutical composition contains at least one of the above compounds of formula I in association with at least one other active principle.

According to a preferred embodiment of the invention, also in combination with the preceding embodiments, the pharmaceutical compositions may be for intravescical, intravenous, topical or oral administration.

The compounds of the invention of formula (I) are conveniently formulated in pharmaceutical compositions using conventional techniques and excipients such as those described in "Remington's Pharmaceutical Sciences Handbook" MACK Publishing, New York, 18th ed., 1990.

A sixth object of the present invention is a therapeutic method for the prevention, reduction of the risk of, amelioration and/or treatment of said diseases associated with activity of TRPM8 comprising the administration of the above compound of Formula I in a subject in need thereof.

The compounds of the invention can be administered as the sole active principles or in combination with other therapeutically active compounds.

The administration of the compounds of the invention can be effected by intravesical instillation, by intravenous injection, as a bolus, in dermatological preparations (creams, lotions, sprays and ointments), by inhalation as well as orally in the form of capsules, tablets, syrup, controlled-release formulations and the like.

The average daily dose depends on several factors such as the severity of the disease, the condition, age, sex and weight of the patient. The dose will vary generally from 1 to 1500 mg of compounds of formula (I) per day optionally divided in multiple administrations.

The present invention shall be illustrated by means of the following examples which are not construed to be viewed as limiting the scope of the invention.

EXAMPLES

Synthesis of Preferred Compounds

The compounds listed in Table IV have been synthesised following the procedures described in the following examples.
Materials and Methods All reagents were purchased from Sigma-Aldrich, Fluorochem and Alfa Aesar and used without further purification. Nuclear magnetic resonance (NMR) spectra were recorded in the indicated solvent with tetramethylsilane (TMS) as internal standard on a Bruker Avance3 400 MHz instrument. Chemical shifts are reported in parts per million (ppm) relative to the internal standard. Abbreviations are used as follows: s=singlet, d=doublet, t=triplet, q=quartet, m=multiplet, dd=doublets of doublet, br=broad. Coupling constants (J values) are given in hertz (Hz). Analytical HPLC-MS spectra were recorded on a Thermo Finnigan Surveyor coupled with a Thermo Finnigan LCQ DECA XP-PLUS apparatus and equipped with a C18 (10 µM, 4.6 mm×150 mm) Phenomenex Gemini reverse phase column. The eluent mixture consisted of 10 mM (pH 4.2) ammonium formate/formic acid buffer and acetonitrile used according the gradient from 90:10 to 10:90 at a flow rate of 0.200 mL/min. All MS experiments were performed using electrospray ionization (ESI) in positive ion mode.

All reactions were monitored by thin layer chromatography (TLC) carried out on Grace Resolv Davisil silica gel plates 250 µm thick, 60 F254, visualized by using UV (254 nm) or stains such as $KMnO_4$, p-anisaldehyde, and ceric ammonium molybdate (CAM). Chromatographic purifications were carried out on silica gel columns with Grace Resolv Davisil silica 60. All organic solutions were dried over anhydrous $Na_2SO_4$ or $MgSO_4$ and concentrated on a rotary evaporator. All compounds used for biological assays are at least of 98% purity based on HPLC analytical results monitored with 220 and 254 nm wavelengths, unless otherwise noted.
General Procedure A Example 1

Synthesis of 2-(4-chlorophenyl)-4-hydroxy-1,3-thiazole-5-carboxylic acid (1)

Ethyl-2-(4-chlorophenyl)-4-hydroxy-1,3-thiazole-5-carboxylate 8 (0.5 g, 1.8 mmol) (prepared according the general Procedure B, see below) was dissolved in dioxane (3 mL) and aqueous hydrochloric acid (37%) (0.3 mL) was added. The mixture was irradiated by microwave (250 W, 150° C.) for 10 min, whereupon the solvent was removed under vacuum. The crude product was purified by HPLC to yield the acid (0.34 g, 74%) as a white solid.
$^1$H-NMR ($CD_3OD$) δ (ppm): 8.01 (d, 2H, J=8.6), 7.50 (d, 2H, J=8.6).

Example 2

Synthesis of 4-hydroxy-2-(4-methylphenyl)-1,3-thiazole-5-carboxylic acid (2)

Following the procedure A and starting from ethyl 4-hydroxy-2-(4-methylphenyl)-1,3-thiazole-5-carboxylate 9 (0.25 g, 0.94 mmol) (prepared according the general Procedure B, see below), compound 2 was obtained as a white solid following HPLC purification (154 mg, 70%). $^1$H-NMR (Acetone-$d_6$) δ (ppm): 7.94 (d, 2H, J=7.0), 7.33 (d, 2H, J=7.0), 2.42 (s, 3H).

Example 3

Synthesis of 2-(3-fluorophenyl)-4-hydroxy-1,3-thiazole-5-carboxylic acid (3)

Following the general procedure A and starting from ethyl 2-(3-fluorophenyl)-4-hydroxy-1,3-thiazole-5-carboxylate 10 (0.2 g, 0.738 mmol) (prepared according the general Procedure B, see below), compound 3 was obtained as a white solid following HPLC purification (120 mg, 68%). $^1$H-NMR ($CD_3OD$) δ (ppm): 13.29 (br s, 1H), 7.82-7.78 (m, 1H), 7.69-7.64 (m, 1H), 7.71-7.46 (m, 2H).

Example 4

Synthesis of 2-(4-fluorophenyl)-4-hydroxy-1,3-thiazole-5-carboxylic acid (4)

Following the general procedure A and starting from ethyl 2-(4-fluorophenyl)-4-hydroxy-1,3-thiazole-5-carboxylate 11 (123 mg, 0.46 mmol) (prepared according the general Procedure B, see below), compound 4 was obtained as yellow solid following HPLC purification (78 mg, 71%).
$^1$H-NMR (DMSO-$d_6$) δ (ppm): 7.93 (d, 2H, J=7.2), 7.59 (d, 2H, J=7.1), 2.62 (s, 3H).

General Procedure B

Example 5

Synthesis of methyl 4-hydroxy-2-phenyl-1,3-thiazole-5-carboxylate (5)

Benzenecarbothioamide (0.29 g, 2.09 mmol) and dimethyl 2-chloromalonate (447 µL, 3.5 mmol) were dissolved in dioxane (50 mL). The mixture was heated to 80° C. and stirred overnight, whereupon the solvent was removed under vacuum. 5 was obtained as a yellow solid after purification of the crude product by trituration in acetonitrile (345 mg, 70%). $^1$H-NMR (dmso-$d_6$) δ (ppm): 12.3 (br s, 1H), 7.95-7.92 (m, 2H), 7.55-7.53 (m, 3H), 3.75 (s, 3H); MS (ES$^{1+}$) m/z: 236.53 (M+1).

Example 6

Synthesis of methyl 2-(2,4-difluorophenyl)-4-hydroxy-1,3-thiazole-5-carboxylate (6)

Following the general procedure B and starting from commercially available 2,4-difluorobenzenecarbothioamide (80 mg, 0.46 mmol) and dimethyl 2-chloromalonate (0.75 mL, 5.86 mmol), 6 was obtained as a pale yellow solid after purification of the crude product by trituration in acetonitrile (85 mg, 68%). $^1$H-NMR (CDCl$_3$, TMS) δ (ppm): 8.41-8.34 (m, 1H), 7.05-6.93 (m, 2H), 3.94 (s, 3H); MS (ES$^{1+}$) m/z: 272.69 (M+1).

Example 7

Synthesis of ethyl 4-hydroxy-2-phenyl-1,3-thiazole-5-carboxylate (7)

Following the general procedure B and starting from commercially available benzenecarbothioamide (0.2 g, 1.45 mmol) and diethyl chloropropanedioate (0.3 mL, 1.82 mmol), 7 was obtained as a yellow solid after purification of the crude product by trituration in acetonitrile (253 mg, 70%). $^1$H-NMR (dmso-$d_6$) Δ (ppm): 12.3 (br s, 1H), 7.95-7.92 (m, 2H), 7.55-7.53 (m, 3H), 4.43 (q, 2H, J=7.03), 1.42 (t, 3H, J=7.03); MS (ES$^{1+}$) m/z: 250.53 (M+1); 222.42 (M−28).

Example 8

Synthesis of ethyl 2-(4-chlorophenyl)-4-hydroxy-1,3-thiazole-5-carboxylate (8)

Following the general procedure B and starting from commercially available 4-chlorobenzenecarbothioamide (2.04 g, 11.93 mmol) and the corresponding amount of diethyl chloropropanedioate, 8 was obtained as a yellow solid (2.42 g, 71%) by trituration in acetonitrile. $^1$H-NMR (CDCl$_3$, TMS) δ (ppm) 9.96 (brs, 1H), 7.94 (d, 2H, J=8.6), 7.45 (d, 2H, J=8.6), 4.43 (q, 2H, J=7.0), 1.42 (t, 3H, J=7.0); MS (ES$^{1+}$) m/z: 298.36 (M−28+41), 285.42 (M+1), 257.64 (M−28).

Example 9

Synthesis of ethyl 4-hydroxy-2-(4-methylphenyl)-1,3-thiazole-5-carboxylate (9)

Following the general procedure B and starting from commercially available 4-methylbenzenecarbothioamide (123 mg, 0.81 mmol) and the corresponding amount of diethyl chloropropanedioate, 9 was obtained as a yellow solid after purification of the crude product by trituration in acetonitrile (146 mg, 68%). $^1$H-NMR (CDCl$_3$, TMS) δ (ppm): 9.94 (brs, 1H), 7.88 (d, 2H, J=8.1), 7.26 (d, 2H, J=8.1), 4.62 (q, 2H, J=7.0), 2.41 (s, 3H), 1.39 (t, 3H, J=7.0); MS (ES$^{1+}$) m/z: 264.30 (M+1).

Example 10

Synthesis of ethyl 2-(3-fluorophenyl)-4-hydroxy-1,3-thiazole-5-carboxylate (10)

Following the general procedure B and starting from commercially available 3-fluorobenzenecarbothioamide (223 mg, 1.44 mmol) and the corresponding amount of diethyl chloropropanedioate, 10 was obtained as a white solid after purification of the crude product by trituration in acetonitrile (250 mg, 65%). $^1$H-NMR (CDCl$_3$, TMS) δ (ppm): 9.93 (br s), 7.76-7.69 (m, 2H), 7.46-7.39 (m, 1H), 7.22-7.17 (m, 1H), 4.40 (q, 2H, J=7.5), 1.40 (t, 3H, J=7.5); MS (ES$^{1+}$) m/z: 240.13 (M−27), 282.66 (M−27+41).

Example 11

Synthesis of ethyl 2-(4-fluorophenyl)-4-hydroxy-1,3-thiazole-5-carboxylate (11)

Following the general procedure B and starting from commercially available 4-fluorobenzenecarbothioamide (243 mg, 1.57 mmol) and the corresponding amount of diethyl chloropropanedioate, 11 was obtained as a white solid after purification of the crude product by trituration in acetonitrile (280 mg, 67%). $^1$H-NMR (CDCl$_3$, TMS) δ (ppm): 9.94 (s, 1H), 8.01-7.96 (m, 2H), 7.17-7.12 (m, 2H), 4.39 (q, 2H, J=7.0), 1.40 (t, 3H, J=7.0); MS (ES$^{1+}$) m/z: 240.23 (M−27).

Example 12

Synthesis of ethyl-4-hydroxy-2-(4-pyridin-4-yl)phenyl-1,3-thiazole-5-carboxylate (12)

Following the general procedure B and starting from commercially available pyridine-4-carbothioamide (217 mg, 1.57 mmol) and the corresponding amount of diethyl chloropropanedioate, 12 was obtained as a yellow solid after purification of the crude product by trituration in acetonitrile (275 mg, 70%). $^1$H-NMR (MeOD-$d_4$) δ (ppm): 9.91 (br s, 1H), 8.70 (d, 2H, J=5.9), 7.81 (d, 2H, J=5.9), 4.36 (q, 2H, J=7.0), 1.35 (t, 3H, J=7.0); MS (ES$^{1+}$) m/z: 251.81 (M+1).

Example 13

Synthesis of ethyl 2-(4-(dimethylamino)phenyl)-4-hydroxythiazole-5-carboxylate (13)

Following the general procedure B and starting from commercially available 4-(dimethylamino)benzenecarbothioamide (88 mg, 0.48 mmol) and the corresponding amount of diethyl chloropropanedioate, 13 was obtained as a white solid after purification of the crude product by trituration in acetonitrile (117 mg, 82%). $^1$H-NMR (DMSO-d$_6$) δ (ppm): 11.82 (br s, 1H), 7.76 (d, 2H, J=8.6), 6.77 (d, 2H, J=9.2), 4.28 (q, 2H, J=7.03), 3.02 (s, 6H), 1.26 (t, 3H, J=7.03); MS (ES$^{1+}$) m/z: 293.88 (M+1); 265.83 (M−28); 306.83 (M−28+41).

Example 14

Synthesis of ethyl 2-(3-chlorophenyl)-4-hydroxy-1,3-thiazole-5-carboxylate (14)

Following the general procedure B and starting from commercially available 3-chlorobenzenecarbothioamide (1.47 g, 8.54 mmol) and the corresponding amount of diethyl chloropropanedioate, 14 was obtained as a white solid after purification of the crude product by trituration in acetonitrile (1.7 g, 71%). $^1$H-NMR (CDCl$_3$, TMS) δ (ppm): 9.98 (br s, 1H), 8.01 (s, 1H), 7.87 (d, 1H, J=7.57), 7.49-7.33 (m, 2H), 4.43 (q, 2H, J=7.03), 1.42 (t, 3H, J=7.03); MS (ES$^{1+}$) m/z: 297.79 (M−28+41); 284.81 (M+1); 256.76 (M−28).

Example 15

Synthesis of ethyl 4-hydroxy-2-[2'-(trifluoromethyl)biphenyl-3-yl]-1,3-thiazole-5-carboxylate (15)

3-Bromobenzenecarbothioamide (1.00 g, 4.62 mmol) and diethyl chloropropanedioate (1.0 mL, 6.0 mmol) were dissolved in dioxane (35 mL). The mixture was heated at 80° C. and stirred overnight, whereupon the solvent was removed under vacuum. Ethyl 2-(3-bromophenyl)-4-hydroxy-1,3-thiazole-5-carboxylate was obtained as a yellow solid (1.09 g, 72%) by trituration in acetonitrile. An oven-dried Schlenk tube equipped with a magnetic stir bar was charged with 1.5 mL of an aqueous solution of K$_2$CO$_3$ (2M, 3.0 mmol), tetrakis(triphenylphosphine)palladium(0) (140 mg, 0.121 mmol) and toluene (3 mL). The tube was capped with a rubber septum and immersed in an oil bath at 80° C. for 30 min. Ethyl 2-(3'-bromophenyl)-4-hydroxy-1,3-thiazole-5-carboxylate (188 mg, 0.575 mmol) and 2-trifluoromethyl-phenylboronic acid (218 mg, 1.15 mmol) were then added, and the reaction mixture stirred at 80° C. Upon complete consumption of the starting material (12 h), as judged by thin-layer chromatography analysis, the reaction mixture was filtered on a celite pad. The filtrate was diluted with ethyl acetate, and extracted with water. The organic layers were further washed with brine and dried over sodium sulfate. The product was isolated by column chromatography (hexanes/EtOAc) as a yellow solid (56 mg, 25%). $^1$H-NMR (DMSO-d$_6$) δ (ppm): 10.82 (brs, 1H), 7.96 (d, 2H, J=8.11), 7.86 (d, 2H, J=7.57), 7.78-7.73 (m, 1H), 7.67-7.62 (m, 1H), 7.47-7.41 (m, 2H), 4.16 (q, 2H, J=7.03), 1.24 (t, 3H, J=7.03).

Example 16

Synthesis of ethyl 2-(2'-fluorobiphenyl-3-yl)-4-hydroxy-1,3-thiazole-5-carboxylate (16)

The compound was prepared according to the experimental procedure described for compound 15 and starting from ethyl 2-(3'-bromophenyl)-4-hydroxy-1,3-thiazole-5-carboxylate (0.14 g, 0.43 mmol) and 2 fluorophenylboronic acid (0.12 g, 0.86 mmol). Compound 16 was obtained as a yellow oil after HPLC purification (106 mg, 72%). $^1$H-NMR (CDCl$_3$, TMS) δ (ppm): 10.98 (brs, 1H), 8.00 (d, 2H, J=7.58), 7.71 (d, 2H, J=7.58), 7.57-7.47 (m, 2H), 7.39-7.35 (m, 1H), 7.28-7.17 (m, 1H), 4.41 (q, 2H, J=6.49), 1.41 (t, 3H, J=6.49).

Example 17

Synthesis of ethyl 4-hydroxy-2-[2'-(trifluoromethyl)biphenyl-4-yl]-1,3-thiazole-5-carboxylate (17)

The compound was prepared according to the experimental procedure described for compound 15 and starting from ethyl 2-(4-bromophenyl)-4-hydroxy-1,3-thiazole-5-carboxylate (0.12 g, 0.36 mmol) and 2-trifluoromethylphenylboronic acid (136 mg, 0.72 mmol). Compound 17 was obtained as a yellow solid after purification of the crude product by trituration with acetonitrile (106 mg, 75%). $^1$H-NMR (DMSO-d$_6$) δ (ppm): 10.23 (br s, 1H), 7.96 (d, 2H, J=8.11), 7.86 (d, 2H, J=7.57), 7.78-7.73 (m, 1H), 7.67-7.62 (m, 1H), 7.47-7.41 (m, 2H), 4.16 (q, 2H, J=7.03), 1.24 (t, 3H, J=7.03).

Example 18

Synthesis of ethyl 2-(2'-fluorobiphenyl-4-yl)-4-hydroxy-1,3-thiazole-5-carboxylate (18)

The compound was prepared according to the experimental procedure described for compound 15 and starting from ethyl 2-(4-bromophenyl)-4-hydroxy-1,3-thiazole-5-carboxylate (0.12 mg, 0.36 mmol) and 2-fluorophenylboronic acid (0.1 mg, 0.72 mmol). Compound 18 was obtained as a white solid after purification of the crude product by trituration with acetonitrile (105 mg, 85%). $^1$H-NMR (DMSO-d$_6$) δ (ppm): 12.27 (brs, 1H), 8.06 (d, 2H, J=7.57), 7.74 (d, 2H, J=7.57), 7.66-7.60 (m, 1H), 7.52-7.46 (m, 1H), 7.40-7.33 (m, 2H), 4.25 (q, 2H, J=7.03), 1.28 (t, 3H, J=7.03).

Example 19

Synthesis of ethyl 2-{4-[(2-fluorobenzyl)oxy]phenyl}-4-hydroxy-1,3-thiazole-5-carboxylate (19)

Following the general procedure B and starting from 4-(2'-fluorobenzyloxy)phenyl)-benzenecarbothioamide (0.4 g, 1.53 mmol) and diethyl chloropropanedioate (0.45 g, 2.29 mmol), compound 19 was obtained as a white solid after purification of the crude product by trituration in acetonitrile (446 mg, 78%). $^1$H-NMR (DMSO-d$_6$) δ (ppm): 12.10 (br s, 1H), 7.94 (d, 2H, J=8.70), 7.63-7.55 (m, 1H), 7.51-7.43 (m, 1H), 7.33-7.15 (m, 4H), 5.26 (s, 2H), 4.24 (q, 2H, J=7.05), 1.29 (t, 3H, J=7.05).

Example 20

Synthesis of ethyl 2-{4-[(4-fluorobenzyl)oxy]phenyl}-4-hydroxy-1,3-thiazole-5-carboxylate (20)

Following the general procedure B and starting from 4-(4'-fluorobenzyloxy)phenyl)-benzenecarbothioamide (0.31 g, 1.19 mmol) and diethyl chloropropanedioate (0.35 g, 1.78 mmol), compound 20 was obtained as a white solid after purification of the crude product by trituration in acetonitrile (359 mg, 81%). $^1$H-NMR (DMSO-d$_6$) δ (ppm): 12.06 (br s, 1H), 7.90 (d, 2H, J=8.65), 7.55-7.49 (m, 2H), 7.27-7.20 (m, 2H), 7.14 (d, 2H, J=8.65), 5.18 (s, 2H), 4.22 (q, 2H, J=7.03), 1.25 (t, 3H, J=7.03).

Example 21

Synthesis of ethyl 2-(4-fluorophenyl)-4-{[(trifluoromethyl)sulfonyl]oxy}-1,3-thiazole-5-carboxylate (21)

To a solution of ethyl 2-(4-fluorophenyl)-4-hydroxy-1,3-thiazole-5-carboxylate 11 (2.3 g, 8.6 mmol) in dry $CH_2Cl_2$ (50 mL), $Et_3N$ (1.4 mL, 10.1 mmol) was added and the mixture was stirred for 40 min at room temperature. The reaction mixture was then cooled to −10° C. and trifluomethanesulfonic anhydride (1.7 mL, 10.1 mmol) was added dropwise, keeping the temperature under −5° C. The reaction mixture was stirred for 12 h at room temperature. Upon complete consumption of starting compound, the mixture was washed with a satured solution of $NH_4Cl$ (80 mL). The aqueous layer was then extracted with ethyl acetate (2×50 mL). The organic layers further washed with brine and dried over dry $Na_2SO_4$. Compound 21 was isolated by chromatography (hexane/EtOAc) as pale yellow solid (3.0 g, 87%). $^1$H-NMR ($CDCl_3$, TMS) δ (ppm): 7.97-7.92 (m, 2H), 7.21-7.15 (m, 2H), 4.43 (q, 2H, J=7.0), 1.41 (t, 3H, J=7.0).

Example 22

Synthesis of ethyl 4-methoxy-2-(4-methylphenyl)-1,3-thiazole-5-carboxylate (22)

Ethyl 4-hydroxy-2-(4-methylphenyl)-1,3-thiazole-5-carboxylate 9, (0.1 g, 0.379 mmol) was dissolved in DMF (4 mL). $K_2CO_3$ (0.11 g, 0.802 mmol) was added and the mixture heated to 60° C. while stirring. After 15 min. iodomethane (59 µL, 0.95 mmol) was added and the mixture was stirred overnight at the same temperature. After cooling at room temperature, ethyl acetate (15 mL) was added and the mixture washed with water (2×15 mL). The organic phase was dried over dry $Na_2SO_4$ and evaporated to dryness. The crude product was purified by HPLC to yield compound 22 as a white solid (0.080 g, 76%). $^1$H-NMR (acetone-d6) δ (ppm): 7.90 (d, 2H, J=7.6), 7.35 (d, 2H, J=7.6), 4.30-4.19 (m, 2H), 3.89 (s, 3H), 2.40 (s, 3H), 1.36-1.24 (m, 3H); MS ($ES^{1+}$) m/z: 278.55 (M+1).

Example 23

Synthesis of ethyl 2-(4-methylphenyl)-4-(2-methylpropoxy)-1,3-thiazole-5-carboxylate (23)

Compound 23 was prepared according to the experimental procedure described for 22 and starting from ethyl 4-hydroxy-2-(4-methylphenyl)-1,3-thiazole-5-carboxylate 9 (85 mg, 0.32 mmol) and 1-iodo-2-methylpropane (147 mg, 0.80 mmol). Compound 23 was obtained as a white solid after HPLC purification (89 mg, 87%). $^1$H-NMR (CDCl3, TMS) δ (ppm): 7.87 (d, 2H, J=8.1), 7.29 (d, 2H, J=8.1), 4.35 (m, 4H), 2.42 (s, 3H), 2.20 (m, 1H), 1.80 (d, 6H, J=6.5), 1.38 (t, 3H, J=7.0); MS ($ES^{1+}$) m/z: 320.96 (M+1), 264.79 (M−57), 236.77 (M−57-28).

General Procedure C

Example 24

Synthesis of ethyl 4-(benzyloxy)-2-phenyl-1,3-thiazole-5-carboxylate (24)

Ethyl 4-hydroxy-2-phenyl-1,3-thiazole-5-carboxylate 7, (0.2 g, 0.80 mmol) was dissolved in DMF (2 mL). $K_2CO_3$ (0.22 g, 1.604 mmol) was added and the mixture was heated at 60° C. while stirring. After 15 min 1-(bromomethyl)benzene (164 mg, 0.96 mmol) was added and the mixture was stirred overnight at the same temperature. After cooling to room temperature, ethyl acetate (10 mL) was added and the mixture washed with water (2×15 mL). The organic phase was dried over dry $Na_2SO_4$ and evaporated to dryness. The crude product was purified by HPLC to yield compound 24 as a white solid (241 mg, 89%). $^1$H-NMR ($CDCl_3$, TMS) δ (ppm): 8.0-7.9 (m, 4H), 7.87 (d, 1H, J=7.0), 7.48-7.28 (m, 5H), 5.37 (s, 2H), 4.37 (q, 2H, J=7.0), 1.42 (t, 3H, J=7.0); MS ($ES^{1+}$) m/z: 340.19 (M+1).

Example 25

Synthesis of ethyl 4-[(3-chlorobenzyl)oxy]-2-(4-chlorophenyl)-1,3-thiazole-5-carboxylate (25)

The title compound was prepared according to the general procedure C. starting from ethyl 2-(4-chlorophenyl)-4-hydroxy-1,3-thiazole-5-carboxylate 8 (111 mg, 0.39 mmol) and 1-(bromomethyl)-3-chlorobenzene (96 mg, 0.47 mmol). Compound 25 was obtained as pale yellow solid after HPLC purification (138 mg, 87%). $^1$H-NMR ($CDCl_3$, TMS) δ (ppm): 7.79 (d, 2H, J=7.1), 7.71 (d, 1H, J=7.0), 7.42-7.27 (m, 5H), 5.73 (s, 2H), 4.29 (q, 2H), 1.38 (t, 3H); MS ($ES^{1+}$) m/z: 409.03 (M+1).

Example 26

Synthesis of ethyl 4-[(3-chlorobenzyl)oxy]-2-(3-fluorophenyl)-1,3-thiazole-5-carboxylate (26)

The title compound was prepared according to the general procedure C and starting from ethyl 2-(3-fluorophenyl)-4-hydroxy-1,3-thiazole-5-carboxylate 10 (0.1 g, 0.37 mmol) and 1-(bromomethyl)-3-chlorobenzene (91 mg, 0.44 mmol). Compound 26 was obtained as white solid after HPLC purification (113 mg, 78%). $^1$H-NMR ($CDCl_3$, TMS) δ (ppm): 7.97 (m, 1H), 7.84-7.71 (m, 3H), 7.58-7.27 (m, 4H), 5.69 (s, 2H), 4.38 (q, 2H), 1.41 (t, 3H); MS ($ES^{1+}$) m/z: 392.71 (M+1).

Example 27

Synthesis of ethyl 4-(4-chlorobenzyloxy)-2-phenyl-1,3-thiazole-5-carboxylate (27)

Following the general procedure C and starting from ethyl 4-hydroxy-2-phenyl-1,3-thiazole-5-carboxylate 7, (58 mg, 0.23 mmol), 1-chloro-4-(chloromethyl)benzene (92.6 mg, 0.57 mmol), compound 27 was obtained as a white solid after HPLC purification (75 mg, 86%). $^1$H-NMR ($CDCl_3$, TMS) δ (ppm): 7.94-7.92 (m, 2H), 7.50-7.45 (m, 5H), 7.35-7.33 (m, 2H), 5.60 (s, 2H), 4.33 (q, 2H, J=7.0), 1.36 (t, 2H, J=7.0); MS ($ES^{1+}$) m/z: 374.89 (M+1).

Example 28

Synthesis of ethyl 4-(4-chlorobenzyloxy)-2-(3-chlorophenyl)-1,3-thiazole-5-carboxylate (28)

Following the general procedure C and starting from ethyl 2-(3-chlorophenyl)-4-hydroxy-1,3-thiazole-5-carboxylate 14 (0.3 g, 1.06 mmol) and 1-chloro-4-(chloromethyl)benzene (426.7 mg, 2.65 mmol), compound 28 was obtained as white solid after HPLC purification of the crude product (302 mg, 70%). $^1$H-NMR (CDCl$_3$, TMS) δ (ppm): 7.96 (s, 1H), 7.79 (d, 1H, J=7.5), 7.51-7.36 (m, 6H), 5.62 (s, 2H), 4.35 (q, 2H, J=5.6), 1.39 (t, 3H, J=5.6); MS (ES$^{1+}$) m/z: 409.03 (M+1).

Example 29

Synthesis of ethyl 4-[(4-chlorobenzyl)oxy]-2-(4-methylphenyl)-1,3-thiazole-5-carboxylate (29)

Following the general procedure C and starting from ethyl 4-hydroxy-2-(4-methylphenyl)-1,3-thiazole-5-carboxylate 9, (0.1 g, 0.401 mmol) and 1-chloro-4-(chloromethyl)benzene (0.161 g, 1.00 mmol), compound 29 was isolated as a white solid (0.112 g, 72%). $^1$H-NMR (CDCl$_3$, TMS) δ (ppm): 7.85 (d, 2H, J=8.1), 7.51 (d, 2H, J=8.6), 7.36 (d, 2H, J=8.1), 7.27 (d, 2H, J=7.6), 5.62 (s, 2H), 4.35 (q, 2H, J=7.03), 2.42 (s, 3H), 1.38 (t, 3H, J=7.03); MS (ES$^{1+}$) m/z: 389.02 (M+1).

Example 30

Synthesis of ethyl 4-[(4-chlorobenzyl)oxy]-2-(3-fluorophenyl)-1,3-thiazole-5-carboxylate (30)

The title compound was prepared according to the general procedure C and starting from ethyl 2-(3-fluorophenyl)-4-hydroxy-1,3-thiazole-5-carboxylate 10 (0.105 g, 0.39 mmol) and 1-(bromomethyl)-4-chlorobenzene (96 mg, 0.47 mmol. Compound 30 was obtained as yellow solid after HPLC purification (119 mg, 78%). $^1$H-NMR (CDCl$_3$, TMS) δ (ppm): 7.89 (s, 1H), 7.78 (d, 1H, J=7.8), 7.62-7.59 (m, 3H), 7.55-7.41 (m, 3H), 5.62 (s, 2H), 4.35 (q, 2H, J=5.6), 1.39 (t, 3H, J=5.6); MS (ES$^{1+}$) m/z: 392.6 (M+1).

Example 31

Synthesis of ethyl 4-(2-chlorobenzyloxy)-2-phenyl-1,3-thiazole-5-carboxylate (31)

Following the general procedure C and starting from ethyl 2-phenyl-4-hydroxy-1,3-thiazole-5-carboxylate 7, (0.12 g, 0.48 mmol) and 1-chloro-2-(chloromethyl)benzene (0.2 g, 1.2 mmol), compound 31 was obtained as white solid after HPLC purification of the crude product (117 mg, 65%). $^1$H-NMR (CDCl$_3$, TMS) δ (ppm): 8.0-7.9 (m, 3H), 7.87 (d, 1H, J=7.0), 7.48-7.28 (m, 5H), 5.77 (s, 2H), 4.37 (q, 2H, J=7.0), 1.42 (t, 3H, J=7.0); MS (ES$^{1+}$) m/z: 374.99 (M+1).

Example 32

Synthesis of ethyl 4-(2-chlorobenzyloxy)-2-(4-fluorophenyl)-1,3-thiazole-5-carboxylate (32)

Following the general procedure C and starting from ethyl 2-(4-fluorophenyl)-4-hydroxy-1,3-thiazole-5-carboxylate 11, (0.27 g, 1.01 mmol) and 1-chloro-2-(chloromethyl)benzene (0.41 g, 2.52 mmol), compound 32 was obtained as white solid after HPLC purification of the crude product (261 mg, 66%). $^1$H-NMR (CDCl$_3$, TMS) δ (ppm): 7.99-7.95 (m, 2H), 7.78 (d, 1H, J=7.5), 7.41 (d, 1H, J=9.0), 7.35-7.25 (m, 2H), 7.20-7.12 (m, 2H), 5.74 (s, 2H), 4.37 (q, 2H, J=7.3), 1.42 (t, 3H, J=7.0); MS (ES$^{1+}$) m/z: 392.97 (M+1).

Example 33

Synthesis of ethyl 4-(2-chlorobenzyloxy)-2-(4-chlorophenyl)-1,3-thiazole-5-carboxylate (33)

Following the general procedure C and starting from ethyl 2-(4-chlorophenyl)-4-hydroxy-1,3-thiazole-5-carboxylate 8 (37 mg, 0.13 mmol) and 1-chloro-2-(chloromethyl)benzene (52 mg, 0.32 mmol), compound 33 was obtained as a white solid after HPLC purification (40 mg, 75%). $^1$H-NMR (CDCl$_3$, TMS) δ (ppm): 7.91 (d, 2H, J=8.6), 7.76 (d, 1H, J=7.0), 7.46-7.29 (m, 5H), 5.75 (s, 2H), 4.37 (q, 2H, J=5.6), 1.40 (t, 3H, J=5.6); MS (ES$^{1+}$) m/z: 409.03 (M+1).

Example 34

Synthesis of ethyl 4-(2-chlorobenzyloxy)-2-(3-chlorophenyl)-1,3-thiazole-5-carboxylate (34)

Following the general procedure C and starting from ethyl 2-(3-chlorophenyl)-4-hydroxy-1,3-thiazole-5-carboxylate 14, (0.18 g, 0.63 mmol) and 1-chloro-2-(chloromethyl)benzene (254 mg, 1.57 mmol), compound 34 was obtained as white solid after HPLC purification of the crude product (167 mg, 65%). $^1$H-NMR (CDCl$_3$, TMS) δ (ppm): 7.99 (s, 1H), 7.85-7.76 (m, 2H), 7.48-7.28 (m, 5H), 5.76 (s, 2H), 4.38 (q, 2H, J=5.6), 1.41 (t, 3H, J=5.6); MS (ES$^{1+}$) m/z: 409.31 (M+1).

Example 35

Synthesis of ethyl 4-[(2-chlorobenzyl)oxy]-2-(4-methylphenyl)-1,3-thiazole-5-carboxylate (35)

Following the general procedure C and starting from ethyl 2-p-tolyl-4-hydroxy-1,3-thiazole-5-carboxylate 9, (0.18 g, 0.68 mmol) and 1-chloro-2-(chloromethyl)benzene (273 mg, 1.69 mmol), compound 35 was obtained as white solid after HPLC purification of the crude product (181 mg, 74%). $^1$H-NMR (CDCl$_3$, TMS) δ (ppm): 7.87 (d, 2H, J=8.6), 7.78 (d, 1H, J=7.0), 7.45-7.32 (m, 5H), 5.75 (s, 2H), 4.37 (q, 2H, J=7.3), 2.42 (s, 3H), 1.42 (t, 3H, J=7.0); MS (ES$^{1+}$) m/z: 389.00 (M+H).

Example 36

Synthesis of ethyl 2-phenyl-4-{[4-(trifluoromethyl)benzoyl]oxy}-1,3-thiazole-5-carboxylate (36)

Ethyl 4-hydroxy-2-phenyl-1,3-thiazole-5-carboxylate 7 (0.1 g, 0.401 mmol) and pyridine (0.036 mL, 0.48 mmol) were dissolved in CH$_2$Cl$_2$ (5 mL). 4-(Trifluoromethyl)benzoyl chloride (0.154 g, 0.802 mmol) was slowly added, and the mixture was stirred overnight at room temperature. After solvent removal under reduced pressure, the crude product was purified by HPLC yielding the title compound as a white solid (0.126 g, 74%). $^1$H-NMR (CDCl$_3$, TMS) δ (ppm): 8.37 (d, 2H, J=8.1), 7.99-7.96 (m, 2H), 7.81 (d, 2H, J=8.1), 7.52-7.45 (m, 3H), 4.26 (q, 2H, J=7.6), 1.21 (t, 3H, J=7.6); MS (ES$^{1+}$) m/z: 422.99 (M+1).

Example 37

Synthesis of ethyl 2-(3-fluorophenyl)-4-{[4-(trifluoromethyl)benzoyl]oxy}-1,3-thiazole-5-carboxylate (37)

The title compound was prepared according to the procedure described for compound 36 and starting from ethyl 2-(3-fluorophenyl)-4-hydroxy-1,3-thiazole-5-carboxylate 10 (83 mg, 0.31 mmol). Compound 37 was obtained as yellow solid after HPLC purification (110 mg, 81%).

$^1$H-NMR (CDCl$_3$, TMS) δ (ppm): 7.96-7.79 (m, 2H), 7.51-7.36 (m, 6H), 4.35 (q, 2H, J=6.8), 1.39 (t, 3H, J=6.6); MS (ES$^{1+}$) m/z: 440.33 (M+1).

Example 38

Synthesis of ethyl 2-(4-methylphenyl)-4-{[4-(trifluoromethyl)benzoyl]oxy}-1,3-thiazole-5-carboxylate (38)

The title compound was prepared according to the procedure described for compound 36 and stating from ethyl 4-hydroxy-2-(4-methylphenyl)-1,3-thiazole-5-carboxylate 9 (72 mg, 0.27 mmol). Compound 38 was obtained as red solid after HPLC purification (99 mg, 83%). $^1$H-NMR (CDCl$_3$, TMS) δ (ppm): 7.83 (d, 2H, J=8.1), 7.50 (d, 2H, J=8.1), 7.36 (d, 2H, J=8.1), 7.30 (d, 2H, J=7.6), 4.31 (q, 2H, J=7.03), 2.39 (s, 3H), 1.38 (t, 3H, J=7.03); MS (ES$^{1+}$) m/z: 436.4 (M+1).

Example 39

Synthesis of ethyl 4-(2-((1R,2S,5R)-2-isopropyl-5-methylcyclohexyloxy)acetoyloxy)-2-(4-methylphenyl)-1,3-thiazole-5-carboxylate (39)

Following the procedure adopted for the preparation of compound 36 and starting from ethyl 4-hydroxy-2-p-tolyl-1,3-thiazole-5-carboxylate 9 (0.15 g, 0.57 mmol) and 2-((1R,2S,5R)-2-isopropyl-5-methylcyclohexyloxy)acetyl chloride (265 mg, 1.14 mmol), compound 39 was obtained as white solid after purification by HPLC of the crude product (196 mg, 75%). $^1$H-NMR (CDCl$_3$, TMS) δ (ppm): 7.85 (d, 2H, J=8.1), 7.27 (d, 2H, J=7.0), 4.53 (s, 2H), 4.35 (q, 2H, J=7.0), 3.38 (m, 1H), 2.43 (s, 3H), 2.20-1.97 (m, 1H), 1.90-1.81 (m, 2H), 1.75 (m, 3H), 1.67-1.57 (m, 2H), 1.43 (m, 1H) 1.40 (m, 3H), 1.38 (t, 3H, J=7.0), 1.09-1.07 (m, 6H); MS (ES$^{1+}$) m/z: 461.28 (M+1), 433.22 (M−28), 264.79 (M−196).

Example 40

Synthesis of ethyl 4-[(benzylcarbamoyl)oxy]-2-(4-chlorophenyl)-1,3-thiazole-5-carboxylate (40)

1-(isocyanatomethyl)benzene (28.7 mg, 0.21 mmol) was added to a solution of ethyl 2-(4-chlorophenyl)-4-hydroxy-1,3-thiazole-5-carboxylate 8 (50 mg, 0.18 mmol) in toluene. The resulting mixture was stirred at 80° C. for 12 h and then concentrated under reduced pressure. The crude was triturated in ethyl acetate to give compound 40 as white solid (57 mg, 65%). $^1$H-NMR (CDCl$_3$, TMS) δ (ppm): 8.00-7.90 (m, 2H), 7.54-7.30 (m, 6H), 5.65 (br s, 1H), 4.53 (m, 2H), 4.36 (m, 2H), 1.38 (t, 3H, J=7.03 Hz); MS (ES$^{1+}$) m/z: 418.09 (M+1), 325.91 (M−92); 284.75 (M−134).

Example 41

Synthesis of ethyl 4-(2-aminoethoxy)-2-(4-chlorophenyl)-1,3-thiazole-5-carboxylate (41)

Following the procedure adopted for the preparation of compound 36 and starting from ethyl 2-(4-chlorophenyl)-4-hydroxy-1,3-thiazole-5-carboxylate 8, (0.2 g, 0.704 mmol) and 2-bromoethanamine (218 mg, 1.76 mmol), compound 41 was obtained as a brownish solid (178 mg, 77%). $^1$H-NMR (MeOD-d$_4$) δ (ppm): 7.98 (d, 2H, J=8.1 Hz), 7.54 (d, 2H, J=8.1 Hz), 4.82 (m, 2H), 4.38 (q, 2H, J=7.0 Hz), 3.48 (m, 2H), 1.38 (t, 3H, J=7.0 Hz); MS (ES$^{1+}$) m/z: 327.90 (M+1), 368.96 (M+41); 297.78 (M−43); 284.77 (M−44); 256.73 (M−44-27).

Example 42

Synthesis of ethyl 2-(4-chlorophenyl)-4-{2-[(furan-2-ylmethyl)amino]ethoxy}-1,3-thiazole-5-carboxylate (42)

Ethyl 4-(2-aminoethoxy)-2-(4-chlorophenyl)-1,3-thiazole-5-carboxylate 41 (0.15 g, 0.46 mmol) and furan-2-carbaldehyde (48 mg, 0.51 mmol) were mixed in dry MeOH (15 mL) at room temperature under nitrogen atmosphere. The mixture was stirred at room temperature for 1 h, until the aldimine formation was completed (determined by analytic HPLC). The aldimine solution in MeOH was carefully treated with solid NaBH$_4$ (0.6 g, 16 mmol). The reaction mixture was stirred for further 2 h and quenched with a saturated aqueous solution of NH$_4$Cl. The pH of the aqueous layer was adjusted to 7 with saturated aqueous NaHCO$_3$. The reaction mixture was then diluted with ethyl acetate (20 mL) and extracted with diethyl ether. The organic extracts were washed with saturated aqueous NaCl and dried (MgSO$_4$). The solvent was evaporated to give compound 42 as a white solid (175 mg, 98%). $^1$H-NMR (CDCl$_3$, TMS) δ (ppm): 7.84 (d, 2H, J=8.6), 7.39 (d, 2H, J=8.6), 7.35 (s, 1H), 6.29-6.31 (m, 1H), 6.21-6.22 (m, 1H), 4.66 (t, 2H, J=5.4), 4.31 (q, 2H, J=7.0), 3.89 (s, 2H), 3.07 (t, 2H, J=5.4), 1.34 (t, 3H, J=7.0); MS (ES$^{1+}$) m/z: 407.96 (M+1).

General Procedure D

Example 43

Synthesis of 4-[(4-chlorobenzyl)oxy]-2-(4-methylphenyl)-1,3-thiazole-5-carboxylic acid (43)

Ethyl 4-[(4-chlorobenzyl)oxy]-2-(4-methylphenyl)-1,3-thiazole-5-carboxylate 29 (0.50 g, 1.3 mmol) was dissolved in dioxane (3 mL) and 1M NaOH (1.3 mL, 1.0 eq.) was added. The mixture was stirred at room temperature overnight. Upon complete consumption of starting material, as judged by thin-layer chromatography analysis, H$_2$O (5 mL) was added to the reaction mixture. After extraction by CH$_2$Cl$_2$ (3×5 mL), the aqueous phase was acidified with diluted HCl to pH 3-4, and extracted with EtOAc (3×5 mL). The organic layers were further washed with brine and dried over dry Na$_2$SO$_4$. The solvent was removed under vacuum to yield the acid 43 (0.43 g, 92%) as a white solid. $^1$H-NMR (CD$_3$OD) δ (ppm): 7.87 (d, 2H, J=7.0), 7.55 (d, 2H, J=7.6), 7.38 (d, 2H, J=7.0), 7.32 (d, 2H, J=7.6), 5.61 (s, 2H), 2.42 (s, 3H); MS (ES$^{1+}$) m/z: 360.90 (M+1).

Example 44

Synthesis of 4-(4-chlorobenzyloxy)-2-phenyl-1,3-thiazole-5-carboxylic acid (44)

Following the general procedure D and starting from ethyl 4-(4-chlorobenzyloxy)-2-phenyl-1,3-thiazole-5-carboxylate 27 (0.15 g, 0.40 mmol), compound 44 was obtained as a white solid (135 mg, 98%). $^1$H-NMR (DMSO-d$_6$) δ (ppm):

12.95 (br s, 1H), 8.00-7.98 (m, 2H), 7.57-7.53 (m, 5H), 7.49-7.46 (m, 2H), 5.59 (s, 2H); MS (ES$^{1+}$) m/z: 346.59 (M+1), 302.66 (M−44).

Example 45

Synthesis of 4-(4-chlorobenzyloxy)-2-(4-chlorophenyl)-1,3-thiazole-5-carboxylic acid (45)

Following the general procedure D and starting from ethyl 4-(4-chlorobenzyloxy)-2-(4-chlorophenyl)-1,3-thiazole-5-carboxylate (0.11 g, 0.27 mmol), compound 45 was obtained as a white solid (99 mg, 96%). $^1$H-NMR (DMSO-d$_6$) δ (ppm): 13.02 (br s, 1H), 8.06-8.00 (m, 2H), 7.67-7.47 (m, 6H), 5.60 (s, 2H); MS (ES$^{1+}$) m/z: absent.

Example 46

Synthesis of 4-(4-chlorobenzyloxy)-2-(3-chlorophenyl)-1,3-thiazole-5-carboxylic acid (46)

Following the general procedure D and starting from ethyl 4-(4-chlorobenzyloxy)-2-(3-chlorophenyl)-1,3-thiazole-5-carboxylate 28 (0.1 g, 0.24 mmol), compound 46 was obtained as a white solid (87 mg, 94%). $^1$H-NMR (DMSO-d$_6$) δ (ppm): 13.04 (br s, 1H), 8.03 (s, 1H), 7.95 (d, 2H, J=7.57), 7.66-7.54 (m, 3H), 7.47 (d, 2H, J=7.57), 5.60 (s, 2H); MS (ES$^{1+}$) m/z: absent.

Example 47

Synthesis of 4-(benzyloxy)-2-phenyl-1,3-thiazole-5-carboxylic acid (47)

Following the procedure D and starting from ethyl 4-(benzyloxy)-2-phenyl-1,3-thiazole-5-carboxylate 24 (0.15 g, 048 mmol), compound 47 was obtained as a white solid (134 mg, 90%). $^1$H-NMR (CDCl$_3$, TMS) δ (ppm): 7.99-7·94 (m, 3H), 7.55-7.37 (m, 6H), 6.96 (brs, 1H), 5.65 (s, 2H); MS (ES$^{1+}$) m/z: 312.86 (M+1).

Example 48

Synthesis of 4-[(3-chlorobenzyl)oxy]-2-(3-fluorophenyl)-1,3-thiazole-5-carboxylic acid (48)

The title compound was prepared according to the general procedure D and starting from ethyl 4-[(3-chlorobenzyl)oxy]-2-(3-fluorophenyl)-1,3-thiazole-5-carboxylate 26 (58 mg, 0.14 mmol). Compound 48 was obtained as a whitish solid (46 mg, 91%). $^1$H-NMR (DMSO-d$_6$) δ (ppm): 13.12 (br s, 1H), 8.02 (s, 1H), 7.96-7.93 (m, 1H), 7.68-7.49 (m, 4H), 7.41-7.38 (m, 2H), 5.66 (s, 2H); MS (ES$^{1+}$) m/z: 364.7 (M+1).

Example 49

Synthesis of 4-(2-chlorobenzyloxy)-2-phenyl-1,3-thiazole-5-carboxylic acid (49)

Following the general procedure D and starting from ethyl 4-(2-chlorobenzyloxy)-2-phenyl-1,3-thiazole-5-carboxylate 31 (90 mg, 0.24 mmol), compound 49 was obtained as a white solid (81 mg, 98%). $^1$H-NMR (DMSO-d$_6$) δ (ppm): 12.97 (br s, 1H), 8.00-7.97 (m, 2H), 7.70-7.68 (m, 1H), 7.57-7.51 (m, 4H), 7.41-7.38 (m, 2H), 5.67 (s, 2H); MS (ES$^{1+}$) m/z: 346.6 (M+1), 263.5 (M−125+1+41), 222.5 (M−125+1).

Example 50

Synthesis of 4-(2-chlorobenzyloxy)-2-(4-fluorophenyl)-1,3-thiazole-5-carboxylic acid (50)

Following the general procedure D and starting from ethyl 4-(2-chlorobenzyloxy)-2-(4-fluorophenyl)-1,3-thiazole-5-carboxylate 32 (0.11 g, 0.28 mmol), compound 50 was obtained as a white solid (97 mg, 95%). $^1$H-NMR (DMSO-d$_6$) δ (ppm): 12.97 (brs, 1H), 8.07-8.02 (m, 2H), 7.70-7.67 (m, 1H), 7.54-7.51 (m, 1H), 7.41-7.36 (m, 4H), 5.66 (s, 2H); MS (ES$^{1+}$) m/z: absent.

Example 51

Synthesis of 4-(2-chlorobenzyloxy)-2-(4-chlorophenyl)-1,3-thiazole-5-carboxylic acid (51)

Following the general procedure D and starting from ethyl 4-(2-chlorobenzyloxy)-2-(4-chlorophenyl)-1,3-thiazole-5-carboxylate 33 (50 mg, 0.12 mmol), compound 51 was obtained as a yellow solid (43 mg, 92%). $^1$H-NMR (DMSO-d$_6$) δ (ppm): 13.00 (br s, 1H), 8.01 (d, 2H, J=8.1), 7.74-7.66 (m, 1H), 7.62 (d, 2H, J=8.1), 7.54-7.51 (m, 1H), 7.41-7.39 (m, 2H), 5.66 (s, 2H); MS (ES$^{1+}$) m/z: absent.

Example 52

Synthesis of 4-(2-chlorobenzyloxy)-2-(3-chlorophenyl)-1,3-thiazole-5-carboxylic acid (52)

Following the general procedure D and starting from ethyl 4-(2-chlorobenzyloxy)-2-(3-chlorophenyl)-1,3-thiazole-5-carboxylate 34 (105 mg, 0.26 mmol), compound 52 was obtained as a white solid (96 mg, 98%). $^1$H-NMR (DMSO-d$_6$) δ (ppm): 13.02 (br s, 1H), 8.02 (s, 1H), 7.96-7.93 (m, 1H), 7.70-7.50 (m, 4H), 7.42-7.39 (m, 2H), 5.67 (s, 2H); MS (ES$^{1+}$) m/z: absent.

Example 53

Synthesis of 4-(2-chlorobenzyloxy)-2-(4-methylphenyl)-1,3-thiazole-5-carboxylic acid (53)

Following the general procedure D and starting from ethyl 4-(2-chlorobenzyloxy)-2-(4-methylphenyl)-1,3-thiazole-5-carboxylate 35 (80 mg, 0.21 mmol), compound 53 was obtained as a white solid (72 mg, 97%). $^1$H-NMR (DMSO-d$_6$) δ (ppm): 12.92 (br s, 1H), 7.90-7.87 (m, 2H), 7.72-7.68 (m, 1H), 7.55-7.51 (m, 1H), 7.43-7.34 (m, 4H), 5.67 (s, 2H), 2.38 (s, 3H); MS (ES$^{1+}$) m/z: 360.73 (M+1).

Example 54

Synthesis of 4-[(2-chlorobenzyl)oxy]-2-(3-fluorophenyl)-1,3-thiazole-5-carboxylic acid (54)

Following the general procedure D and starting from ethyl 4-[(2-chlorobenzyl)oxy]-2-(3-fluorophenyl)-1,3-thiazole-5-carboxylate (89 mg, 0.22 mmol), compound 54 was obtained as a white solid (76 mg, 92%). $^1$H-NMR (DMSO-

Example 55

Synthesis of 2-phenyl-4-{[4-(trifluoromethyl)benzyl]oxy}-1,3-thiazole-5-carboxylic acid (55)

Following the general procedure D and starting from ethyl 2-phenyl-4-{[4-(trifluoromethyl)benzyl]oxy}-1,3-thiazole-5-carboxylate (91 mg, 0.22 mmol), compound 55 was obtained as brown solid (77 mg, 93%). $^1$H-NMR (DMSO-$d_6$) δ (ppm): 12.93 (br s, 1H), 8.05-7.96 (m, 2H), 7.57-7.53 (m, 5H), 7.49-7.46 (m, 2H), 5.59 (s, 2H); MS (ES$^{1+}$) m/z: 380.49 (M+1).

Example 56

Synthesis of 2-(3-fluorophenyl)-4-{[4-(trifluoromethyl)benzyl]oxy}-1,3-thiazole-5-carboxylic acid (56)

Following the general procedure D and starting from ethyl 2-(3-fluorophenyl)-4-{[4-(trifluoromethyl)benzyl]oxy}-1,3-thiazole-5-carboxylate (101 mg, 0.23 mmol), compound 56 was obtained as pale yellow solid (82 mg, 90%). $^1$H-NMR (DMSO-$d_6$) δ (ppm): 12.83 (br s, 1H), 8.05-7.96 (d, 2H, J=8.0), 7.76 (m, 1H), 7.57-7.53 (m, 3H), 7.49-7.46 (d, 2H, J=8.1), 5.59 (s, 2H); MS (ES$^{1+}$) m/z: 398.4 (M+1).

Example 57

Synthesis of 2-phenyl-4-{[4-(trifluoromethyl)benzoyl]oxy}-1,3-thiazole-5-carboxylic acid (57)

Following the general procedure described for compound 36 and starting from 4-hydroxy-2-phenyl-1,3-thiazole-5-carboxylic acid (89 mg, 0.40 mmol) and 4-(trifluoromethyl)benzoyl chloride (158 mg, 0.76 mmol), compound 57 was obtained as a white solid after HPLC purification (124 mg, 79%). $^1$H-NMR (CDCl$_3$, TMS) δ (ppm): 8.36 (d, 2H, J=8.1), 7.99-7.96 (m, 2H), 7.81 (d, 2H, J=8.1), 7.52-7.45 (m, 3H), MS (ES$^{1+}$) m/z: 394.11 (M+1).

Example 58

Synthesis of 2-(3-fluorophenyl)-4-{[4-(trifluoromethyl)benzoyl]oxy}-1,3-thiazole-5-carboxylic acid (58)

Following the procedure described for compound 57 and starting from 2-(3-fluorophenyl)-4-hydroxy-1,3-thiazole-5-carboxylic acid 3 (91 mg, 0.38 mmol), compound 58 was obtained as yellow solid after HPLC purification (136 mg, 87%). $^1$H-NMR (CDCl$_3$, TMS) δ (ppm): 8.29 (d, 2H, J=8.1), 7.91 (d, 2H, J=8.1), 7.88-7.96 (m, 3H), 7.52-7.45 (m, 1H), MS (ES$^{1+}$) m/z: 412.3 (M+1).

Example 59

Synthesis of 2-(4-methylphenyl)-4-{[4-(trifluoromethyl)benzoyl]oxy}-1,3-thiazole-5-carboxylic acid (59)

Following the general procedure described for compound 57 and starting from ethyl 4-hydroxy-2-(4-methylphenyl)-1,3-thiazole-5-carboxylate 2 (0.1 g, 0.42 mmol) and 4-(trifluoromethyl)benzoyl chloride (158 mg, 0.76 mmol), compound 59 was obtained as white solid after purification by HPLC of the crude product (110 mg, 71%). $^1$H-NMR (CDCl$_3$, TMS) δ (ppm): 8.28 (d, 2H, J=7.6), 8.03 (d, 2H, J=8.1), 7.80 (d, 2H, J=8.1), 7.34 (d, 2H, J=7.6), 2.47 (s, 3H); MS (ES$^{1+}$) m/z: absent.

Example 60

Synthesis of 4-methoxy-2-(4-methylphenyl)-1,3-thiazole-5-carboxylic acid (60)

Following the general procedure D and starting from ethyl 4-methoxy-2-(4-methylphenyl)-1,3-thiazole-5-carboxylate 22 (47 mg, 0.17 mmol), compound 60 was obtained as a white solid (40 mg, 94%). $^1$H-NMR (DMSO-$d_6$): δ (ppm): 12.81 (br s, 1H), 7.88 (d, 2H, J=7.8), 7.35 (d, 2H, J=7.8), 4.11 (s, 3H), 2.38 (s, 3H); MS (ES$^{1+}$) m/z: 250.71 (M+1), 291.84 (M+41), 232.76 (M−18).

Example 61

Synthesis of 2-(4-methylphenyl)-4-(2-methylpropoxy)-1,3-thiazole-5-carboxylic acid (61)

Following the general procedure D and starting from ethyl 2-(4-methylphenyl)-4-(2-methylpropoxy)-1,3-thiazole-5-carboxylate 23 (0.85 g, 2.67 mmol), compound 61 was obtained as a white solid (731 mg, 94%). $^1$H-NMR (CDCl$_3$, TMS) δ (ppm): 7.86 (d, 2H, J=7.6), 7.28 (d, 2H, J=7.6), 4.46 (d, 2H, J=6.5), 2.43 (s, 3H), 2.15-2.30 (m, 1H), 1.09 (d, 6H, J=6.5); MS (ES$^{1+}$) m/z: 292.86 (M+1), 277.83 (M−15), 236.76 (M−56).

General Procedure E

Example 62

Synthesis of ethyl 4-[(tert-butoxycarbonyl)amino]-2-(4-fluorophenyl)-1,3-thiazole-5-carboxylate (62)

Pd$_2$(dba)$_3$ (15 mg, 0.015 mmol) and Xantphos (27 mg, 0.046 mmol) were dissolved in dry THF (6 mL) under N$_2$ atmosphere. The mixture was stirred at room temperature for 20 min. 0.100 g (0.240 mmol) of ethyl 2-(4-fluorophenyl)-4-{[(trifluoromethyl)sulfonyl]oxy}-1,3-thiazole-5-carboxylate 21 (0.2 g, 0.5 mmol) was then added, and after 5 minutes, tert-butyl carbamate (70.4 mg, 0.6 mmol) was added. The mixture was irradiated by microwave (250 W, 135° C.) for 1 h, whereupon the mixture was filtered on a celite pad and the solvent was removed under vacuum. The crude product was purified by flash column chromatography (eluent hexane/ethyl acetate mixture of increasing polarity) to yield the compound 62 as a yellow solid (157 mg, 86%).

$^1$H-NMR (CDCl$_3$, TMS) δ (ppm): 9.26 (br s, 1H), 8.06-8.01 (m, 2H), 7.16-7.10 (m, 2H), 4.36 (q, 2H, J=7.0), 1.56 (s, 9H), 1.39 (t, 3H, J=7.0); MS (ES$^{1+}$) m/z: 311 (M−55).

Example 63

Synthesis of ethyl 4-amino-2-(4-fluorophenyl)-1,3-thiazole-5-carboxylate hydrochloride (63)

Ethyl 4-[(tert-butoxycarbonyl)amino]-2-(4-fluorophenyl)-1,3-thiazole-5-carboxylate 62 (157 mg, 0.43 mmol) was dissolved in a solution of 1.25 M HCl in CH$_3$OH and stirred for 1 h at room temperature. The solvent was

Example 64

Synthesis of ethyl 4-acetamido-2-(4-methylphenyl)-1,3-thiazole-5-carboxylate (64)

Following the general procedure E and starting from ethyl 2-(4-methylphenyl)-4-{[(trifluoromethyl)sulfonyl]oxy}-1,3-thiazole-5-carboxylate (0.1 g, 0.25 mmol) and acetamide (18 mg, 0.30 mmol), compound 64 was obtained as white solid after purification by HPLC of the crude product (56 mg, 73%). $^1$H-NMR (CDCl$_3$, TMS) δ (ppm): 7.86 (d, 2H, J=8.1), 7.28 (d, 2H, J=8.1), 4.39 (q, 2H, J=7.0), 2.55 (br s, 3H), 2.43 (s, 3H), 1.40 (t, 3H, J=7.0); MS (ES$^{1+}$) m/z: 305.4 (M+1), 263.8 (M−42).

Example 65

Synthesis of ethyl 2-(4-methylphenyl)-4-{[4-(trifluoromethyl)benzoyl]amino}-1,3-thiazole-5-carboxylate (65)

Following the procedure described for compound 36 and starting from ethyl 4-amino-2-(4-methylphenyl)-1,3-thiazole-5-carboxylate (0.1 g, 0.38 mmol) and 4-(trifluoromethyl)benzoyl chloride (158 mg, 0.76 mmol), compound 65 was obtained as white solid after HPLC purification of the crude product (117 mg, 71%). $^1$H-NMR (CDCl$_3$, TMS) δ (ppm): 11.03 (br s, 1H), 8.19 (d, 2H, J=8.11 Hz), 8.03 (d, 2H, J=8.11 Hz), 7.84 (d, 2H, J=8.11 Hz), 7.28 (d, 2H, J=8.11 Hz), 4.39 (q, 1H, J=7.03 Hz), 2.44 (s, 3H), 1.40 (t, 3H, J=7.03 Hz); MS (ES$^{1+}$) m/z: 435.10 (M+1).

Example 66

Synthesis of ethyl 2-(4-methylphenyl)-4-[(phenylcarbamoyl)amino]-1,3-thiazole-5-carboxylate (66)

Following the procedure described for compound 40 and starting from ethyl 4-amino-2-(4-methylphenyl)-1,3-thiazole-5-carboxylate (1.23 g, 4.68 mmol) and phenylisocyanate (557 mg, 4.68 mmol), compound 66 was obtained as a white solid (1.63 g, 88%). $^1$H-NMR (CDCl$_3$, TMS) δ (ppm): 10.97 (br s, 1H), 9.11 (br s, 1H), 7.86 (d, 2H, J=8.1), 7.63 (d, 2H, J=8.1), 7.41-7.34 (m, 4H), 7.13 (t, 1H, J=7.0), 4.41 (q, 2H, J=7.0), 2.47 (s, 3H), 1.42 (t, 3H, J=7.0); MS (ES$^{1+}$) m/z: 382.44 (M+1).

Example 67

Synthesis of ethyl 4-[(2-aminoethyl)amino]-2-(4-methylphenyl)-1,3-thiazole-5-carboxylate (67)

Following the general procedure E and starting from ethyl 2-(4-methylphenyl)-4-{[(trifluoromethyl)sulfonyl]oxy}-1,3-thiazole-5-carboxylate (150 mg, 0.38 mmol) and ethane-1,2-diamine (27.4 mg, 0.45 mmol), compound 67 was obtained as pale yellow solid after purification by flash column cromatography (eluent hexane/ethyl acetate mixture of increasing polarity) of the crude product (84.7 mg, 73%). $^1$H-NMR (CDCl$_3$, TMS) δ (ppm): 7.83-7.78 (d, 2H, J=8.1), 7.25-7.19 (d, 2H, J=8.1), 4.25 (q, 2H, J=7.0), 3.70 (t, 2H, J=5.9), 2.39 (s, 3H), 1.90 (brs, 2H), 1.38 (t, 3H, J=7.0); MS (ES$^{1+}$) m/z: =306.2 (M+1).

Example 68

Synthesis of ethyl 2-(4-chlorophenyl)-4-{[2-(methylamino)ethyl]amino}-1,3-thiazole-5-carboxylate (68)

Following the general procedure E and starting from ethyl 2-(4-chlorophenyl)-4-{[(trifluoromethyl)sulfonyl]oxy}-1,3-thiazole-5-carboxylate (0.1 g, 0.240 mmol) and N-methylethane-1,2-diamine, compound 68 was obtained as a yellow powder (60 mg, 74%). $^1$H-NMR (CDCl$_3$, TMS) δ (ppm): 7.90 (d, 2H, J=8.6), 7.41 (d, 2H, J=8.6), 4.30 (q, 2H, J=7.3), 3.84 (q, 2H, J=5.9), 2.99 (t, 2H, J=2.9), 2.57 (s, 3H), 1.36 (t, 3H, J=7.0); MS (ES$^{1+}$) m/z: 381.96 (M+41), 340.92 (M+1), 309.81 (M−30), 294.73 (M−45).

Example 69

Synthesis of ethyl 2-(4-chlorophenyl)-4-{[2-(propylamino)ethyl]amino}-1,3-thiazole-5-carboxylate (69)

Following the general procedure E and starting from ethyl 2-(4-chlorobenzen)-4-{[(trifluoromethyl)sulfonyl]oxy}-1,3-thiazole-5-carboxylate, (0.12 g, 0.29 mmol) and N-ethylethane-1,2-diamine (25.4 mg, 0.35 mmol), compound 69 was obtained as pale yellow solid after purification by flash column cromatography (eluent hexane/ethyl acetate mixture of increasing polarity) of the crude product (75 mg, 70%).

$^1$H-NMR (CDCl$_3$, TMS) δ (ppm): 7.90 (d, 2H, J=8.6), 7.41 (d, 2H, J=8.6), 5.08 (brs, 1H), 4.30 (q, 2H, J=7.0), 3.93 (q, 2H, J=5.9), 3.02 (t, 2H, J=5.9), 2.89 (t, 2H, J=7.3), 1.78-1.66 (m, 2H), 1.34 (t, 3H, J=7.0), 0.96 (t, 3H, J=7.0); MS (ES$^{1+}$) m/z: 368.95 (M+1).

Example 70

Synthesis of ethyl 4-[(2-aminoethyl)amino]-2-(4-chlorophenyl)-1,3-thiazole-5-carboxylate (70)

The title compound was prepared according to the general procedure E and starting from ethyl 2-(4-chlorophenyl)-4-{[(trifluoromethyl)sulfonyl]oxy}-1,3-thiazole-5-carboxylate (220 mg, 0.53 mmol). Compound 70 was obtained as a pale yellow oil after HPLC purification (124 mg, 72%). MS (ES$^{1+}$) m/z: 326.78 (M+1).

Example 71

Synthesis of ethyl 4-{[2-(methylamino)ethyl]amino}-2-(4-methylphenyl)-1,3-thiazole-5-carboxylate (71)

The title compound was prepared according to the general procedure E and starting from ethyl 2-(4-methylphenyl)-4-{[(trifluoromethyl)sulfonyl]oxy}-1,3-thiazole-5-carboxylate (203 mg, 0.51 mmol). Compound 71 was obtained as whitish solid after HPLC purification in 81% yield (132 mg). MS (ES$^{1+}$) m/z: 320.55 (M+1).

Example 72

Synthesis of ethyl 4-[(2-aminoethyl)amino]-2-[2'-(trifluoromethyl)biphenyl-4-yl]-1,3-thiazole-5-carboxylate (72)

The title compound was prepared according to the general procedure E and starting from ethyl 2-[2'-(trifluoromethyl)biphenyl-4-yl]-4-{[(trifluoromethyl)sulfonyl]oxy}-1,3-thiazole-5-carboxylate (188 mg, 0.35 mmol). Compound 72 was obtained as a white solid after HPLC purification in 61% yield (95 mg). MS (ES$^{1+}$) m/z: 436.41 (M+1).

Example 73

Synthesis of ethyl 4-[(2-aminoethyl)amino]-2-[2'-(trifluoromethyl)biphenyl-3-yl]-1,3-thiazole-5-carboxylate (73)

The title compound was prepared according to the general procedure E and starting from ethyl 2-[2'-(trifluoromethyl)biphenyl-3-yl]-4-{[(trifluoromethyl)sulfonyl]oxy}-1,3-thiazole-5-carboxylate (156 mg, 0.29 mmol). Compound 73 was obtained as dark yellow oil after HPLC purification (72 mg, 56%). MS (ES$^{1+}$) m/z: 436.37 (M+1).

Example 74

Synthesis of ethyl 2-(4-chlorophenyl)-4-{[2-(cyclopentylamino)ethyl]amino}-1,3-thiazole-5-carboxylate (74)

Following the general procedure described for compound 42 and starting from ethyl 4-(2-aminoethylamino)-2-(4-chlorophenyl)-1,3-thiazole-5-carboxylate (0.5 g, 1.53 mmol) and cyclopentanecarbaldehyde (166 mg, 1.69 mmol), compound 74 was obtained as a yellow oil (447 mg, 74%). $^1$H-NMR (CDCl$_3$, TMS) δ (ppm): 7.91 (d, 2H, J=8.12), 7.42 (d, 2H, J=8.12), 6.99 (br s, 1H), 4.31 (q, 2H, J=7.03), 3.84-3.79 (m, 2H), 3.25-3.17 (m, 2H), 3.01-2.97 (m, 2H), 2.70 (br s, 1H), 1.93-1.86 (m, 2H), 1.76-1.66 (m, 2H), 1.61-1.31 (m, 2H), 1.37 (t, 3H, J=7.03); MS (ES$^{1+}$) m/z 394.95 (M+1).

Example 75

Synthesis of ethyl 2-phenyl-4-{[2-(pyrrolidin-1-yl)ethyl]amino}-1,3-thiazole-5-carboxylate (75)

Following the general procedure E and starting from 5-(ethoxycarbonyl)-2-phenylthiazol-4-yl trifluoromethanesulfonate (145 mg, 0.38 mmol) and 2-(pyrrolidin-1-yl)ethanamine (51.4 mg, 0.45 mmol), compound 75 was obtained as a yellow solid after purification by flash column cromatography (eluent hexane/ethyl acetate mixture of increasing polarity) of the crude product (83 mg, 63%). $^1$H-NMR (CDCl$_3$, TMS) δ (ppm): 7.72-7.64 (m, 2H), 7.45-7.38 (m, 1H), 7.20-7.13 (m, 1H), 6.98 (br s, 1H), 4.31 (q, 2H, J=7.03), 3.97-3.90 (m, 2H), 3.16-3.12 (m, 2H), 3.12-3.01 (m, 4H), 2.05-1.96 (m, 4H), 1.35 (t, 3H, J=7.03); MS (ES$^{1+}$) m/z: 346.41 (M+1).

Example 76

Synthesis of ethyl 4-(benzylamino)-2-(3-fluorophenyl)-1,3-thiazole-5-carboxylate (76)

Following the general procedure E and starting from 5-(ethoxycarbonyl)-2-(3-fluorophenyl)thiazol-4-yl trifluoromethanesulfonate (0.15 g, 0.33 mmol) and phenylmethanamine (43 mg, 0.40 mmol), compound 76 was obtained as a yellow solid after purification by flash column cromatography (eluent hexane/ethyl acetate mixture of increasing polarity) of the crude product (96 mg, 76%). $^1$H-NMR (CDCl$_3$, TMS) δ (ppm): 7.74-7.64 (m, 2H), 7.43-7.25 (m, 6H), 7.19-7.12 (m, 1H), 4.86 (s, 2H), 4.29 (q, 2H, J=7.03), 1.34 (t, 3H, J=7.03); MS (ES$^{1+}$) m/z: 357.41 (M+1).

Example 77

Synthesis of ethyl 4-[(1,3-benzodioxol-5-ylmethyl)amino]-2-(3-fluorophenyl)-1,3-thiazole-5-carboxylate (77)

Following the general procedure E and starting from 5-(ethoxycarbonyl)-2-(3-fluorophenyl)thiazol-4-yl trifluoromethanesulfonate (0.15 g, 0.33 mmol) and (benzo[d][1,3]dioxol-5-yl)methanamine (60 mg, 0.40 mmol), compound 77 was obtained as a yellow solid after purification by flash column cromatography (eluent hexane/ethyl acetate mixture of increasing polarity) of the crude product (82 mg, 62%). $^1$H-NMR (CDCl$_3$, TMS) δ (ppm): 7.75-7.70 (m, 2H), 7.46-7.39 (m, 1H), 7.21-7.11 (m, 2H), 6.91-6.78 (m, 2H), 5.96 (s, 2H), 4.77 (s, 2H), 4.31 (q, 2H, J=7.03), 1.46 (s, 1H), 1.38 (t, 3H, J=7.03); MS (ES$^{1+}$) m/z: 401.61 (M+1).

Example 78

Synthesis of ethyl 2-(3-fluorophenyl)-4-[(pyridin-3-ylmethyl)amino]-1,3-thiazole-5-carboxylate (78)

Following the general procedure E and starting from 5-(ethoxycarbonyl)-2-(3-fluorophenyl)thiazol-4-yl trifluoromethanesulfonate (0.15 g, 0.33 mmol) and (pyridin-3-yl)methanamine (43 mg, 0.40 mmol), compound 78 was obtained as a yellow solid after purification by flash column cromatography (eluent hexane/ethyl acetate mixture of increasing polarity) of the crude product (81 mg, 69%). $^1$H-NMR (CDCl$_3$, TMS) δ (ppm): 8.67 (s, 1H), 8.52 (s, 1H), 7.74-7.65 (m, 2H), 7.48-7.36 (m, 1H), 7.32-7.12 (m, 4H), 4.85 (s, 2H), 4.30 (q, 2H, J=7.03), 1.36 (t, 3H, J=7.03); MS (ES$^{1+}$) m/z: 358.53 (M+1).

Example 79

Synthesis of 4-[(2-aminoethyl)amino]-2-(4-methylphenyl)-1,3-thiazole-5-carboxylic acid (79)

The title compound was prepared following the general procedure D and starting from ethyl 4-[(2-aminoethyl)amino]-2-(4-methylphenyl)-1,3-thiazole-5-carboxylate 67 (93 mg, 0.30 mmol). Compound 79 was obtained as a white solid (68 mg, 81%). $^1$H-NMR (CDCl$_3$, TMS) δ (ppm): 7.83 (d, 2H, J=8.1), 7.22 (d, 2H, J=8.1), 3.20 (t, 2H, J=6.9), 2.80 (t, 2H, J=6.9), 2.39 (s, 3H). MS (ES$^{1+}$) m/z: 277.8 (M+1).

Example 80

Synthesis of 4-{[2-(methylamino)ethyl]amino}-2-(4-methylphenyl)-1,3-thiazole-5-carboxylic acid (80)

Following the general procedure D and starting from ethyl 4-{[2-(methylamino)ethyl]amino}-2-(4-methylphenyl)-1,3- thiazole-5-carboxylate 71 (89 mg, 0.27 mmol), compound 80 was obtained as white solid (74 mg, 91%). MS (ES$^{1+}$) m/z: 292.8 (M+1).

Example 81

Synthesis of 4-[(2-aminoethyl)amino]-2-(3-fluorophenyl)-1,3-thiazole-5-carboxylic acid (81)

Following the general procedure D and starting from ethyl 4-[(2-aminoethyl)amino]-2-(3-fluorophenyl)-1,3-thiazole-5-carboxylate (100 mg, 0.32 mmol), compound 81 was obtained as white solid (80 mg, 88%). MS (ES$^{1+}$) m/z: 282.4 (M+1).

General Procedure F

Example 82

Synthesis of sodium 4-[(3-chlorobenzyl)oxy]-2-(3-fluorophenyl)-1,3-thiazole-5-carboxylate (82)

1 eq of NaOH was added to a 30 mM solution of 5-[(3-chlorobenzyl)oxy]-2-(3-fluorophenyl)-1,3-thiazole-4-carboxylic acid 48 and the mixture stirred for 30 min at room temperature. After evaporation under reduced pressure the compound 82 was isolated in form of sodium salt (19 mg, 95%). $^1$H-NMR (DMSO-d$_6$) δ (ppm): 7.89-7.82 (m, 2H), 7.70-7.61 (m, 2H), 7.57-7.53 (m, 4H), 7.42 (m, 2H), 5.42 (s, 2H).

Example 83

Synthesis of sodium 4-[(4-chlorobenzyl)oxy]-2-(4-methylphenyl)-1,3-thiazole-5-carboxylate (83)

Following the procedure F and starting from 4-[(4-chlorobenzyl)oxy]-2-(4-methylphenyl)-1,3-thiazole-5-carboxylic acid 43, compound 83 was obtained as a white solid (54 mg, 95%). $^1$H-NMR (CD$_3$OD) δ (ppm): 7.83 (d, 2H, J=7.0), 7.52 (d, 2H, J=7.6), 7.41 (d, 2H, J=7.0), 7.33 (d, 2H, J=7.6), 5.59 (s, 2H), 2.31 (s, 3H).

Example 84

Synthesis of sodium 4-(4-chlorobenzyloxy)-2-(4-chlorophenyl)-1,3-thiazole-5-carboxylate (84)

Following the general procedure F and starting from 4-(4-chlorobenzyloxy)-2-(4-chlorophenyl)-1,3-thiazole-5-carboxylic acid 45 (0.2 g, 0.526 mmol), compound 84 was obtained as a yellow solid (212 mg, 95%). $^1$H-NMR (DMSO-d$_6$) δ (ppm): 7.89 (d, 2H, J=8.65), 7.57-7.53 (m, 4H), 7.42 (d, 2H, J=8.65), 5.47 (s, 2H).

Example 85

Synthesis of sodium 4-(2-chlorobenzyloxy)-2-(4-chlorophenyl)-1,3-thiazole-5-carboxylate (85)

Following the general procedure F and starting from 4-(2-chlorobenzyloxy)-2-(4-chlorophenyl)-1,3-thiazole-5-carboxylic acid 51 (0.16 g, 0.421 mmol), compound 85 was obtained as a yellow solid (170 mg, 96%). $^1$H-NMR (DMSO-d$_6$) δ (ppm): 7.89-7.78 (m, 3H, J=8.65), 7.61 (d, 2H), 7.47-7.43 (m, 1H), 7.42 (d, 2H, J=8.65), 5.47 (s, 2H).

Example 86

Synthesis of sodium 4-(2-chlorobenzyloxy)-2-(4-methylphenyl)-1,3-thiazole-5-carboxylate (86)

Following the general procedure F and starting from 4-(2-chlorobenzyloxy)-2-(4-methylphenyl)-1,3-thiazole-5-carboxylic acid 53 (0.4 g, 1.11 mmol), compound 86 was obtained as a white solid (421 mg, 89%). $^1$H-NMR (DMSO-d$_6$) δ (ppm): 7.85-7.82 (m, 1H), 7.74 (d, 2H, J=8.11), 7.49-7.46 (m, 1H), 7.37-7.33 (m, 2H), 7.28 (d, 2H, J=8.11), 5.55 (s, 2H), 2.34 (s, 3H).

Example 87

Synthesis of sodium 4-(2-chlorobenzyloxy)-2-(3-fluorophenyl)-1,3-thiazole-5-carboxylate (87)

Following the general procedure F and starting from ethyl 4-(2-chlorobenzyloxy)-2-(3-fluorophenyl)-1,3-thiazole-5-carboxylate 54 (70 mg, 0.179 mmol), compound 87 was obtained as a white solid (69 mg, 92%). $^1$H-NMR (DMSO-d$_6$) δ (ppm): 7.80-7.67 (m, 3H), 7.58-7.47 (m, 2H), 7.41-7.30 (m, 3H), 5.59 (s, 2H).

Example 88

Synthesis of sodium 4-(4-chlorobenzyloxy)-2-(3-fluorophenyl)-1,3-thiazole-5-carboxylate (88)

Following the general procedure F and starting from ethyl 4-(4-chlorobenzyloxy)-2-(3-fluorophenyl)-1,3-thiazole-5-carboxylate (0.1 g, 0.255 mmol), compound 88 was obtained as a yellow solid (100 mg, 98%). $^1$H-NMR (DMSO-d$_6$) δ (ppm): 7.69-7.40 (m, 7H), 7.31-7.24 (m, 1H), 5.44 (s, 2H).

Example 89

Synthesis of (1R,2S,5R)-2-isopropyl-5-methylcyclohexyl-4-(benzyloxy)-2-(4-methylphenyl)-1,3-thiazole-5-carboxylate (89)

Following the general procedure described for compound 36 and starting from (1R,2S,5R)-2-isopropyl-5-methylcyclohexanol (91 mg, 0.58 mmol) and 4-(benzyloxy)-2-(4-methylphenyl)-1,3-thiazole-5-carbonyl chloride (0.1 g, 0.29 mmol) (obtained by treatment of the corresponding acid with SOCl$_2$, 3.0 eq., in toluene), compound 89 was obtained as transparent oil after purification by HPLC (116 mg, 87%). $^1$H-NMR (acetone-d$_6$) δ (ppm): 7.94-7.91 (d, 2H, J=7.8), 7.61-7.58 (m, 2H), 7.44-7.31 (m, 5H), 5.69-5.58 (s, 2H), 4.84 (dt, 1H, J$^1$=10.8, J$^2$=4.3), 2.41 (s, 3H), 2.11-1.99 (m, 2H), 1.77-1.69 (m, 2H), 1.56-1.47 (m, 2H), 1.31-1.27 (m, 1H), 1.17-1.07 (m, 1H), 0.95-0.89 (m, 7H), 0.80 (d, 3H, J=7.0); MS (ES$^{1+}$) m/z: 465.34 (M+1).

Example 90

Synthesis of (1R,2S,5R)-2-isopropyl-5-methylcyclohexyl-4-hydroxy-2-(4-methylphenyl)-1,3-thiazole-5-carboxylate (90)

A solution of (1R,2S,5R)-2-isopropyl-5-methylcyclohexyl 4-(benzyloxy)-2-(4-methylphenyl)-1,3-thiazole-5-carboxylate 89 (0.1 g, 0.21 mmol) in dry THF was hydrogenated at atmospheric pressure in the presence of Pd/C for 1 h. The mixture was then filtered through celite and the filtrate concentrated under reduced pressure to give compound 90 as transparent oil (75 mg, 95%). $^1$H-NMR (CDCl$_3$, TMS) δ (ppm): 10.02 (bs, 1H), 7.90 (d, 2H, J=8.1), 7.34-7.26 (m, 2H), 5.02-4.87 (m, 1H), 2.42 (s, 3H), 1.95-1.87 (m, 2H), 1.78-1.69 (m, 2H), 1.65-1.44 (m, 2H), 1.31-1.28 (m, 1H), 1.22-1.09 (m, 1H), 0.97-0.82 (m, 10H); MS (ES$^{1+}$) m/z: 375.09 (M+1); 236.76 (M−136).

Example 91

Synthesis of ethyl 2-(4-chlorophenyl)-4-(methoxymethoxy)-1,3-thiazole-5-carboxylate (91)

Following the general procedure C and starting from ethyl 4-hydroxy-2-(4-chlorophenyl)-1,3-thiazole-5-carboxylate 8 (0.1 g, 0.35 mmol), and chloro(methoxy)methane (56 mg, 0.70 mmol), compound 91 was obtained as a white solid (110 mg, 96%). $^1$H-NMR (CDCl$_3$, TMS) δ (ppm): 7.94 (d, 2H, J=8.6), 7.45 (d, 2H, J=8.6), 5.67 (s, 2H), 4.43 (q, 2H, J=7.0), 3.6 (s, 3H), 1.42 (t, 3H, J=7.0); MS (ES$^{1+}$) m/z: 328.85 (M+1), 256.67 (M−72), 297.74 (M−72+41).

Example 92

Synthesis of 2-(4-chlorophenyl)-4-(methoxymethoxy)-1,3-thiazole-5-carboxylic acid (92)

Following the general procedure D starting from ethyl 2-(4-chlorophenyl)-4-(methoxymethoxy)-1,3-thiazole-5-carboxylate 91 (0.1 g, 0.3 mmol), compound 92 was obtained as a white solid (86 mg, 95%). $^1$H-NMR (CDCl$_3$, TMS) δ (ppm): 7.92 (d, 2H, J=8.6), 7.43 (d, 2H, J=8.6), 5.42 (s, 2H), 3.71 (s, 3H); MS (ES$^{1+}$) m/z: 299.74 (M+1).

Example 93

Synthesis of 2-(4-chlorophenyl)-4-(methoxymethoxy)-1,3-thiazole-5-carboxamide (93)

2-(4-chlorophenyl)-4-(methoxymethoxy)-1,3-thiazole-5-carboxylic acid 92 (80 mg, 0.28 mmol) was dissolved in dry CH$_2$Cl$_2$ (10 mL) at 0° C., under N$_2$ atmosphere, 1,1'-carbonyldiimidazole (0.41 mmol, 68 mg) was added at the same temperature. The mixture was warmed to room temperature and stirred for 40 min. Gaseous NH$_3$ was bubbled into the mixture and the course of the reaction was monitored by LC-MS analysis. At the end of the reaction the mixture was concentrated under reducer pressure and the crude product triturated with acetone. The resulting precipitate was collected by filtration, washed with diethyl ether and purified by flash column chromatography (eluent: dichloromethane/methanol mixture of increasing polarity). Compound 93 was obtained as white solid (77 mg, 78%). $^1$H-NMR (CDCl$_3$, TMS) δ (ppm): 7.86 (d, 2H, J=8.1), 7.41 (d, 2H, J=8.6), 6.98 (br s, 1H), 5.85 (br s, 1H), 5.70 (s, 2H), 3.59 (s, 3H); MS (ES$^{1+}$) m/z: (ESI+)=300 (M+1), 282 (M−18), 252 (M−48).

Example 94

Synthesis of 2-(4-chlorophenyl)-4-(methoxymethoxy)-1,3-thiazole-5-carbonitrile (94)

A 250 mL three-necked round bottom flask was equipped with a thermometer, flame dried, and charged with N$_2$ and a solution 2-(4-chlorophenyl)-4-(methoxymethoxy)-1,3-thiazole-5-carboxamide 93 (450 mg, 1.5 mmol) in dry CH$_2$Cl$_2$ (8 mL). To this solution DMSO (284 μL, 4.0 mmol) was added and the resulting pale yellow solution cooled to −78° C. A solution of (COCl)$_2$ (270 μL, 3.2 mmol) in dry CH$_2$Cl$_2$ (2 mL) was then added dropwise. After 15 min. stirring at −78° C., Et$_3$N (892 μL, 6.4 mmol) was added dropwise to the mixture. The following addition of DMSO (284 μL, 4.0 mmol), (COCl)$_2$ (270 μL, 3.2 mmol) and Et$_3$N (500 μL, 3.5 mmol) at intervals of 1 h were necessary in order to complete the starting material consumption. The reaction was quenched by addition of water (20 mL), warming of the mixture to room temperature, and extraction of the aqueous layer with ethyl acetate (3×10 mL). The combined organic phases were washed with brine (30 mL), dried over dry Na$_2$SO$_4$ and concentrated in vacuo. Purification by silica gel column chromatography (hexane/acetate 9/1 to 1/1) gave 94 as a pale yellow solid (270 mg, 74%). $^1$H-NMR (CDCl$_3$, TMS) δ (ppm): 7.86 (d, 2H, J=7.6), 7.45 (d, 2H, J=7.6), 5.59 (s, 2H), 3.58 (s, 3H).

Example 95

Synthesis of 2-(4-chlorophenyl)-5-(1H-tetrazol-5-yl)thiazol-4-ol (95)

2-(4-chlorophenyl)-4-(methoxymethoxy)-1,3-thiazole-5-carbonitrile 94 (55 mg, 0.14 mmol), sodium azide (10 mg, 0.16 mmol), zinc chloride (19 mg, 0.14 mmol), and 8 mL of water were mixed in a 25 mL round-bottomed flask. The reaction mixture was vigorously stirred at 100° C. for 72 h. After consumption of the starting material, 6 N HCl (100 μL) and ethyl acetate (7 mL) were added, and stirring was continued until no solid was present and the aqueous layer reached pH 1. Additional ethyl acetate was added; the organic layer was separated and the aqueous one extracted again with ethyl acetate (2×10 mL). The combined organic layers were dried over dry Na$_2$SO$_4$ and concentrated in vacuo. Compound 95 was obtained as pale yellow solid (28 mg, 75%) after preparative HPLC purification. $^1$H-NMR (dmso-d$_6$) δ (ppm): 16.2 (br s, 1H), 13.0 (br s, 1H), 7.99 (d, 2H, J=8.6), 7.62 (d, 2H, J=8.6); MS (ES$^{1+}$) m/z: 278.8 (M+1), 231.8 (M+41), 235.6 (M−28).

Example 96

Synthesis of 2-(4-chlorophenyl)-5-(1-methyl-1H-tetrazol-5-yl)thiazol-4-ol (96)

A 25 mL three-necked round bottom flask was equipped with a thermometer, flame dried, and charged with N$_2$ and a solution of 2-(4-chlorophenyl)-5-(1H-tetrazol-5-yl)thiazol-4-ol 95 (40 mg, 0.14 mmol) in THF (10 mL). To this solution pyridine (12 μL, 0.14 mmol) were added by syringe. The resulting mixture was cooled to 0° C. and stirred for 30 min. Methyl iodide (34 μL, 0.17 mmol) was added dropwise by a syringe, while keeping the temperature below 5° C. After the addition, the ice bath was removed, and the solution stirred at room temperature until all starting material was consumed. The reaction mixture was diluted with ethyl acetate (15 mL) and the reaction was cautiously quenched with HCl 0.5 N (10 mL) at 0° C. The solution was allowed to warm to room temperature, the organic layer separated and the aqueous one extracted again with ethyl acetate (2×10 mL). The combined organic layers were dried over dry Mg$_2$SO$_4$ and concentrated in vacuo. The resulting yellow solid was purified by preparative HPLC to afford the compound 96 as pale yellow solid (27 mg, 65%). $^1$H-NMR (dmso-d$_6$) δ (ppm): 11.98 (br s, 1H), 7.99 (d, 2H, J=8.6), 7.62 (d, 2H, J=8.6), 3.91 (s, 3H); MS (ES$^{1+}$) m/z: 294.75 (M+1).

Example 97

Synthesis of 2-(3-fluorophenyl)-5-(1-methyl-1H-tetrazol-5-yl)-1,3-thiazol-4-ol (97)

Following the procedure described for compound 96 and starting from 2-(3-fluorophenyl)-5-(1H-tetrazol-5-yl)-1,3-thiazol-4-ol, the compound 97 was isolated as dark-yellow oil (73 mg, 47%). $^1$H-NMR (dmso-d$_6$) δ (ppm): 11.79 (br s, 1H), 7.73-7.68 (m, 2H), 7.46-7.39 (m, 1H), 3.82 (s, 3H); MS (ES$^{1+}$) m/z: 278.18 (M+1).

Example 98

Synthesis of 2-(4-chlorophenyl)-5-(5-methyl-4H-1,2,4-triazol-3-yl)-1,3-thiazol-4-ol (98)

To a solution of 2-(4-chlorophenyl)-4-(methoxymethoxy)-1,3-thiazole-5-carbonitrile 94 (0.25 g, 0.890 mmol) in dry toluene (10 mL), a solution of Et$_3$Al (122 μL, 0.89 mmol) in dry toluene was added dropwise and the resulting mixture stirred for 20 min at room temperature. Acetohydrazide (0.165 g, 2.22 mmol) was added and the mixture heated at 90° C. for 6 h until the starting materials had been completely consumed (as checked by TLC and LC-MS analysis). The mixture was diluted with toluene (10 mL) and transferred to a separatory funnel; the organic layer was washed with water, dried over Na$_2$SO$_4$, filtered, and concentrated in vacuo to afford a brown oil which was used in the next step without further purification. The oil was dissolved in toluene (10 mL), added to a microwave vial and irradiated by MW at 170° C. for 20 min. After consumption of the starting material, 2 mL of 6 N HCl were added and vigorous stirring continued for 1 h. The organic layer was isolated and the aqueous layer extracted with ethyl acetate (2×10 mL). The combined organic layers were evaporated and the crude product was purified by flash chromatography on silica gel (petroleum ether/ethyl acetate 90:10 to 70:30) to afford 98 as transparent oil (125 mg, 48%). $^1$H-NMR (dmso-d$_6$) δ (ppm): 12.11 (br s, 1H), 12.98 (br s, 1H), 7.99 (d, 2H, J=7.6), 7.62 (d, 2H, J=7.6), 2.25 (s, 3H); MS (ES$^{1+}$) m/z: 293.74 (M+1).

Example 99

Synthesis of 2-(3-fluorophenyl)-5-(5-methyl-4H-1,2,4-triazol-3-yl)-1,3-thiazol-4-ol (99)

Following the procedure described for compound 98 and starting from 2-(3-fluorophenyl)-4-(methoxymethoxy)-1,3-thiazole-5-carbonitrile, the compound 99 was isolated following flash chromatography on silica gel (CH$_2$Cl$_2$/CH$_3$OH 90:10) as slightly red oil (97 mg, 31%). $^1$H-NMR (dmso-d$_6$) δ (ppm): 11.93 (br s, 1H), 12.80 (br s, 1H), 7.76-7.69 (m, 2H), 7.46-7.39 (m, 1H), 7.22-7.17 (m, 1H), 2.21 (s, 3H); MS (ES$^{1+}$) m/z: 277.27 (M+1).

Example 100

Synthesis of 2-(4-chlorophenyl)-5-(5-methyl-1,2,4-oxadiazol-3-yl)-1,3-thiazol-4-ol (100)

A microwave vial was charged with 2-(4-chlorophenyl)-4-(methoxymethoxy)-1,3-thiazole-5-carbonitrile 94 (250 mg, 0.89 mmol), acetic acid (5 mL), hydroxylamine (117 mg, 3.56 mmol) and 2,2-dimethyl-1,3-dioxane-4,6-dione (Meldrum's acid) (131 mg, 0.91 mmol). The mixture was irradiated by MW for 10 min at 130° C., then quenched with 10 mL of water and the precipitate was filtered and dried under vacuum at 50° C. The solid obtained was dissolved in a mixture of HCl 6N (5 mL) and ethyl acetate (10 mL) and stirred for 1 h. The two phases were separated into a separatory funnel; the organic layer was washed with water, dried over Na$_2$SO$_4$, filtered, and concentrated in vacuo to afford compound 100 as a dark yellow solid (107 mg, 41%). $^1$H-NMR (dmso-d$_6$) δ (ppm): 11.98 (br s, 1H), 7.89 (d, 2H, J=7.5), 7.51 (d, 2H, J=7.6), 2.55 (s, 3H); MS (ES$^{1+}$) m/z: 294.50 (M+1), 316.7 (M+Na).

Example 101

Synthesis of 2-(3-fluorophenyl)-5-(5-methyl-1,2,4-oxadiazol-3-yl)-1,3-thiazol-4-ol (101)

Following the experimental procedure described for compound 100 and starting from 2-(3-fluorophenyl)-4-(methoxymethoxy)-1,3-thiazole-5-carbonitrile compound 101 was isolated as white solid (177 mg, 52%). $^1$H-NMR (dmso-d$_6$) δ (ppm): 11.81 (br s, 1H), 7.76-7.69 (m, 3H), 7.22-7.17 (m, 1H), 2.33 (s, 3H); MS (ES$^{1+}$) m/z: 278.27 (M+1).

Example 102

Synthesis of 3-{4-[(4-chlorobenzyl)oxy]-2-(3-fluorophenyl)-1,3-thiazol-5-yl}-5-methyl-1,2,4-oxadiazole (102)

The title compound was prepared according to the general procedure C and starting from 2-(3-fluorophenyl)-5-(5-methyl-1,2,4-oxadiazol-3-yl)-1,3-thiazol-4-ol 101 (221 mg, 0.8 mmol) and 1-chloro-4-(chloromethyl)benzene (0.16 g, 1.00 mmol). Compound 102 was obtained as dark red oil (234 mg, 73%). $^1$H-NMR (dmso-d$_6$) δ (ppm): 7.83-7.79 (d, 2H, J=7.6), 7.76-7.69 (m, 2H), 7.63-7.59 (m, 1H), 7.51 (d, 2H, J=7.4), 7.22-7.17 (m, 1H), 5.23 (s, 2H), 2.33 (s, 3H); MS (ES$^{1+}$) m/z: 402.8 (M+1).

Example 103

Synthesis of 2-(4-chlorophenyl)-5-(5-methyl-1,3,4-oxadiazol-2-yl)-1,3-thiazol-4-ol (103)

To a cooled solution (0° C.) of 2-(4-chlorophenyl)-4-hydroxy-1,3-thiazole-5-carboxylic acid 1 (0.43 g, 1.68 mmol) in CH$_2$Cl$_2$ (15 mL), 1,1-carbonyldiimidazole (CDI, 275 mg, 1.70 mmol) was added. After stirring 1 h at 0° C., acetohydrazide (124 mg, 1.68 mmol) and diazobicyclo[5.4.0]undec-7-ene (DBU, 260 μL, 1.68 mmol) were added, and the mixture was allowed stirring at room temperature for 4 h. Glacial AcOH (200 μL, 3.5 mmol) was added and the reaction mixture diluted with CH$_2$Cl$_2$ (10 mL). The organic layer washed with saturated NH$_4$Cl (2×10 mL) and water (2×10 mL), dried over Na$_2$SO$_4$, filtered and concentrated under reduced pressure to give a crude residue that, after purification by flash chromatography (CH$_2$Cl$_2$/CH$_3$OH 95:5) afforded N'-acetyl-2-(4-chlorophenyl)-4-hydroxy-1,3-thiazole-5-carbohydrazide as pale yellow oil. The compound was dissolved in polyphosphoric acid (5 mL) in a microwave vial and irradiated by MW for 40 min at 150° C. The solution was added to an ice/water mixture and the precipitate filtered and washed with water. The solid precipitated was dried under vacuum at 50° C. to afford compound 103 as a whitish solid (182 mg, 37%).

$^1$H-NMR (dmso-d$_6$) δ (ppm): 11.89 (br s, 1H), 7.89 (d, 2H, J=7.6), 7.51 (d, 2H, J=7.4), 2.65 (s, 3H); MS (ES$^{1+}$) m/z: 294.50 (M+1), 316.7 (M+Na).

Example 104

Synthesis of 2-(3-fluorophenyl)-5-(5-methyl-1,3,4-oxadiazol-2-yl)-1,3-thiazol-4-ol (104)

The title compound was prepared according to the experimental procedure described for compound 103 and starting from 2-(3-fluorophenyl)-4-hydroxy-1,3-thiazole-5-carboxylic acid 3. Compound 104 was isolated as a yellow oil (109 mg, 59%). $^1$H-NMR (dmso-d$_6$) δ (ppm): 11.79 (br s, 1H), 7.63-7.79 (m, 3H), 7.11-7.18 (m, 1H), 2.61 (s, 3H); MS (ES$^{1+}$) m/z: 278.27 (M+1).

Example 105

Synthesis of ethyl 4-hydroxy-2-phenyl-1,3-oxazole-5-carboxylate (105)

An oven-dried microwave vial was evacuated, backfilled with argon and finally charged with benzamide (0.3 g, 2.48 mmol), diethyl bromopropanedioate (1.27 μL, 7.44 mmol) and dry DMSO (3 mL). The reaction vial was sealed and placed in the microwave reactor and irradiated for 2 h at 250° C. until the complete consumption of the starting materials (as checked by TLC and GC analysis). The crude was diluted with ethyl acetate (20 mL) and washed with water (3×10 mL). The combined organic layers were dried over Na$_2$SO$_4$, filtered and the solvent was removed under reduced pressure. The residue was purified by flash chromatography on silica gel (CH$_2$Cl$_2$/CH$_3$OH 95:5) to afford the compound 105 as colourless oil (83%). $^1$H-NMR (dmso-d$_6$) δ (ppm): 12.3 (br s, 1H), 7.95-7.92 (m, 2H), 7.55-7.53 (m, 3H), 4.43 (q, 2H, J=7.03), 1.42 (t, 3H, J=7.03); MS (ES$^{1+}$) m/z: 234.33 (M+1).

Example 106

Synthesis of ethyl 2-(3-fluorophenyl)-4-hydroxy-1,3-oxazole-5-carboxylate (106)

The title compound was prepared according to the experimental procedure described for compound 105 and starting from 3-fluorobenzamide. Compound 106 was isolated as a yellow oil (99 mg, 59%). $^1$H-NMR (CDCl$_3$, TMS) δ (ppm): 11.98 (br s, 1H), 8.01 (s, 1H), 7.77 (d, 1H, J=7.57), 7.49-7.30 (m, 2H), 4.40 (q, 2H, J=7.03), 1.52 (t, 3H, J=7.03); MS (ES$^{1+}$) m/z: 252.18 (M+1).

Example 107

Synthesis of ethyl 4-hydroxy-2-(4-methylphenyl)-1,3-oxazole-5-carboxylate (107)

The title compound was prepared according to the experimental procedure described for compound 105 and starting from p-tolylbenzamide. Compound 107 was isolated as a whitish oil (39 mg, 79%). $^1$H-NMR (CDCl$_3$, TMS) δ (ppm): 11.94 (br s, 1H), 7.88 (d, 2H, J=7.6), 7.26 (d, 2H, J=7.6), 4.62 (q, 2H, J=7.0), 2.41 (s, 3H), 1.39 (t, 3H, J=7.0); MS (ES$^{1+}$) m/z: 248.25.

Example 108

Synthesis of ethyl 4-[(4-chlorobenzyl)oxy]-2-phenyl-1,3-oxazole-5-carboxylate (108)

Following the general procedure C and starting from ethyl 4-hydroxy-2-phenyl-1,3-oxazole-5-carboxylate 105 (055 g, 2.67 mmol) and 1-chloro-4-(chloromethyl)benzene (1.074 g, 6.67 mmol), compound 108 was obtained as a white solid (0.8 g, 81%). $^1$H-NMR (CDCl$_3$, TMS) δ (ppm): 7.83-7.48 (m, 5H), 7.35 (d, 2H, J=7.5), 7.27 (d, 2H, J=7.6), 5.31 (s, 2H), 4.35 (q, 2H, J=7.03), 1.38 (t, 3H, J=7.03); MS (ES$^{1+}$) m/z: 358.80 (M+1), 380.77 (M+Na).

Example 109

Synthesis of ethyl 4-[(4-chlorobenzyl)oxy]-2-(3-fluorophenyl)-1,3-oxazole-5-carboxylate (109)

Following the general procedure C and starting from ethyl 2-(3-fluorophenyl)-4-hydroxy-1,3-oxazole-5-carboxylate 106 (110 mg, 0.43 mmol), compound 109 was obtained as a white powder (114 mg, 71%). $^1$H-NMR (CDCl$_3$, TMS) δ (ppm): 7.85-7.51 (m, 3H), 7.47 (m, 1H), 7.36 (d, 2H, J=7.6), 7.26 (d, 2H, J=7.6), 5.53 (s, 2H), 4.33 (q, 2H, J=7.03), 1.38 (t, 3H, J=7.03); MS (ES$^{1+}$) m/z: 376.66 (M+1).

Example 110

Synthesis of ethyl 4-[(4-chlorobenzyl)oxy]-2-(4-methylphenyl)-1,3-oxazole-5-carboxylate (110)

Following the general procedure C and starting from ethyl 4-hydroxy-2-(4-methylphenyl)-1,3-oxazole-5-carboxylate 107 (98 mg, 0.39 mmol) compound 110 was obtained as a white powder (114 mg, 79%). $^1$H-NMR (CDCl$_3$, TMS) δ (ppm): 7.82 (d, 2H, J=7.6), 7.49 (d, 2H, J=7.6), 7.23 (d, 2H, J=7.6), 7.19 (d, 2H, J=7.6), 5.32 (s, 2H), 4.30 (q, 2H, J=7.03), 2.39 (s, 3H), 1.28 (t, 3H, J=7.03); MS (ES$^{1+}$) m/z: 372.72 (M+1).

Example 111

Synthesis of ethyl 2-phenyl-4-{[4-(trifluoromethyl)benzoyl]oxy}-1,3-oxazole-5-carboxylate (111)

Following the procedure described for compound 36 and starting from ethyl 4-hydroxy-2-phenyl-1,3-oxazole-5-carboxylate 105 (67 mg, 0.28 mmol) compound 111 was obtained as colorless oil (77 mg, 67%). $^1$H-NMR (CDCl$_3$, TMS) δ (ppm): 7.73-7.51 (m, 5H), 7.47 (d, 2H, J=7.5), 7.35 (d, 2H, J=7.6), 4.37 (q, 2H, J=7.13), 1.48 (t, 3H, J=7.11); MS (ES$^{1+}$) m/z: 406.28 (M+1).

Example 112

Synthesis of 4-[(4-chlorobenzyl)oxy]-2-phenyl-1,3-oxazole-5-carboxylic acid (112)

The title compound was prepared according to the general procedure D and starting from ethyl 4-[(4-chlorobenzyl)oxy]-2-phenyl-1,3-oxazole-5-carboxylate 108 (123 mg, 0.34 mmol). Compound 112 was obtained as slightly dark oil (99 mg, 88%). ¹H-NMR (dmso-d₆) δ (ppm): 12.12 (br s, 1H), 7.71-7.49 (m, 5H), 7.41 (d, 2H, J=8), 7.34 (d, 2H, J=7.6), 5.61 (s, 2H); MS (ES¹⁺) m/z: 330.68 (M+1).

Example 113

Synthesis of 4-[(4-chlorobenzyl)oxy]-2-(3-fluorophenyl)-1,3-oxazole-5-carboxylic acid (113)

The title compound was prepared according to the general procedure D and starting from ethyl 4-[(4-chlorobenzyl) oxy]-2-(3-fluorophenyl)-1,3-oxazole-5-carboxylate 109 (88 mg, 0.23 mmol). Compound 113 was obtained as white solid (70 mg, 86%). ¹H-NMR (dmso-d₆) δ (ppm): 11.91 (br s, 1H), 7.81-7.50 (m, 3H), 7.45 (m, 1H), 7.31 (d, 2H, J=7.6), 7.26 (d, 2H, J=7.6), 5.63 (s, 2H); MS (ES¹⁺) m/z: 348.62 (M+1).

Example 114

Synthesis of 4-[(4-chlorobenzyl)oxy]-2-(4-methylphenyl)-1,3-oxazole-5-carboxylic acid (114)

The title compound was prepared according to the general procedure D and starting from ethyl 4-[(4-chlorobenzyl) oxy]-2-(4-methylphenyl)-1,3-oxazole-5-carboxylate 110 (0.12 g, 0.32 mmol). Compound 114 was obtained as whitish solid (98 mg, 89%). ¹H-NMR (CD₃OD) δ (ppm): 7.89 (d, 2H, J=7.6), 7.53 (d, 2H, J=7.6), 7.41 (d, 2H, J=7.5), 7.33 (d, 2H, J=7.6), 5.43 (s, 2H), 2.39 (s, 3H); MS (ES¹⁺) m/z: 344.66 (M+1).

Example 115

Synthesis of 2-(3-fluorophenyl)-5-(5-methyl-1,2,4-oxadiazol-3-yl)-1,3-oxazol-4-ol (115)

The title compound was prepared according to the experimental procedure described for compound 100 and starting from 2-(3-fluorophenyl)-4-hydroxy-1,3-oxazole-5-carbonitrile (76 mg, 0.25 mmol). Compound 115 was obtained as pale yellow oil (54 mg, 79%). ¹H-NMR (dmso-d₆) δ (ppm): 12.1 (br s, 1H), 7.83-7.74 (m, 3H), 7.11-7.18 (m, 1H), 2.51 (s, 3H); MS (ES¹⁺) m/z: 262.21 (M+1).

Example 116

Synthesis of 3-{4-[(4-chlorobenzyl)oxy]-2-(3-fluorophenyl)-1,3-oxazol-5-yl}-5-methyl-1,2,4-oxadiazole (116)

The title compound was prepared according to the experimental procedure B and starting from 2-(3-fluorophenyl)-5-(5-methyl-1,2,4-oxadiazol-3-yl)-1,3-oxazol-4-ol 115 (98 mg, 0.37 mmol). Compound 116 was obtained as yellow oil (88 mg, 61%). ¹H-NMR (CDCl₃, TMS) δ (ppm): 7.77 (m, 1H), 7.61 (m, 1H), 7.60-7.55 (m, 3H), 7.50 (m, 1H), 7.35-7.29 (m, 2H), 5.40 (s, 2H), 2.45 (s, 3H); MS (ES¹⁺) m/z 386.78 (M+1).

Example 117

Synthesis of ethyl 2-(3-fluorophenyl)-5-hydroxy-1,3-thiazole-4-carboxylate (117)

Triethylamine (3.4 mL, 24 mmol) and 4-methylbenzoyl chloride (1.59 mL, 12.0 mmol) were added to a solution of diethyl 2-aminomalonate hydrochloride (2.28 g, 10.8 mmol in CH₂Cl₂ (40 mL). and the resulting mixture was stirred overnight at room temperature. The mixture was washed with aqueous NaHCO₃ (20 mL), 1M HCl (20 mL), and water (20 mL); the organic layer was dried over anhydrous Na₂SO₄, filtered, and the solvent was evaporated under vacuum to yield the intermediate diethyl [(4-methylbenzoyl) amino]propanedioate as a yellow solid (96%).

Diethyl [(4-methylbenzoyl)amino]propanedioate (3.08 g, 10.5 mmol) was dissolved in THF (50 mL). Lawesson reagent (3.0 g, 7.4 mmol) was added and the mixture stirred overnight at room temperature. After solvent removal under reduced pressure, the crude product was purified by flash column chromatography (eluent:hexane/ethyl acetate mixture of increasing polarity) to give the intermediate diethyl {[(4-methyl phenyl)carbonothioyl]amino}propanedioate (85%).

Diethyl {[(4-methyl phenyl)carbonothioyl] amino}propanedioate (2.47 g, 8.00 mmol) was dissolved in dioxane (35 mL) and phosphoryl chloride (0.5 mL, 5 mmol) was added. The mixture was irradiated by microwave (250 W, 100° C.) for 15 min, whereupon the solvent was removed under vacuum. The compound 117 was obtained by trituration with acetonitrile (1.67 g, 84%). ¹H-NMR (CDCl₃, TMS) δ (ppm): 9.93 (br s, 1H), 7.81 (d, 2H, J=7.3), 7.21 (d, 2H, J=7.3), 4.58 (q, 2H, J=7.0), 2.37 (s, 3H), 1.39 (t, 3H, J=7.0); MS (ES¹⁺) m/z: 264.30 (M+1).

Example 118

Synthesis of 2-(3-fluorophenyl)-5-(2-ethyl-2H-tetrazol-5-yl)-1,3-thiazol-4-ol (compound n. 118)

The compound was synthesized following the procedures described hereinbelow:

1. Preparation of Ethyl 2-(3-fluorophenyl)-4-hydroxy-1,3-thiazole-5-carboxylate (intermediate 1)

Commercial 3-fluorobenzenecarbothioamide (395 mg, 2.55 mmol) and diethyl bromopropanedioate (435 μL, 2.55 mmol) were dissolved in ethanol (8 mL) in a microwave vial. The mixture was irradiated at 100° C. for 30 min. The solvent was removed under reduce pressure ethyl 2-(3-fluorophenyl)-4-hydroxy-1,3-thiazole-5-carboxylate was obtained as a yellow solid after trituration in acetonitrile (476 mg, 70%). ¹H-NMR (CDCl₃) δ (ppm): 9.93 (br s), 7.76-7.69 (m, 2H), 7.46-7.39 (m, 1H), 7.22-7.17 (m, 1H), 4.40 (q, 2H, J=7.5), 1.40 (t, 3H, J=7.5); MS (ES¹⁺) m/z: 268 (M+1).

2. Preparation of 2-(3-fluorophenyl)-4-hydroxy-1,3-thiazole-5-carboxylic acid (intermediate 2)

The intermediate 1 (476 mg, 1.78 mmol) was dissolved in dioxane (5 mL) and 2 mL of aqueous hydrochloric acid (37%) were added. The mixture was heated at 80° C. for 16 h. After solvent removal under vacuum and the crude product was purified by HPLC to yield 2-(3-fluorophenyl)-4-hydroxy-1,3-thiazole-5-carboxylic acid as a white solid (0.315 g, 74%). ¹H-NMR (DMSO-d₆) δ (ppm): 12.2 (br s, 1H), 7.82-7.78 (m, 1H), 7.75-7.71 (m, 1H), 7.71-7.58 (m, 1H), 7.45-7.39 (m, 1H); MS (ES¹⁺) m/z: 238 (M−1).

3. Preparation of 2-(3-fluorophenyl)-4-hydroxy-1,3-thiazole-5-carboxamide (intermediate 3)

The intermediate 2 (130 mg, 0.54 mmol) was dissolved in dry CH₂Cl₂ (10 mL) and 1,1'-carbonyldiimidazole (135 mg, 0.81 mmol) was added at 0° C. The mixture was stirred at room temperature and stirred for 30 min. Gaseous NH$_3$ was bubbled into the mixture and the course of the reaction was monitored by LC-MS analysis. At the end of the reaction the mixture was concentrated under reducer pressure and the crude product triturated with acetone. The resulting solid was purified by flash column chromatography (CH$_2$Cl$_2$/MeOH 95:5 as eluent). 2-(3-fluorophenyl)-4-hydroxy-1,3-thiazole-5-carboxamide was obtained as white solid (101 mg, 78%). $^1$H-NMR (DMSO-d$_6$) δ (ppm): 12.25 (br s, 1H), 9.15 (br s, 2H), 7.80-7.78 (m, 1H), 7.73-7.70 (m, 1H), 7.69-7.60 (m, 1H), 7.45-7.41 (m, 1H); MS (ES$^{1+}$) m/z: 239 (M+1).

4. Preparation of 2-(3-fluorophenyl)-4-hydroxy-1,3-thiazole-5-carbonitrile (intermediate 4)

A 50 mL one-necked round bottom flask was charged with a solution of the intermediate 3 (101 mg, 0.42 mmol) in dry CH$_2$Cl$_2$ (8 mL) and trichloroacetyl chloride (94 μL, 0.84 mmol) was added. After stirring 1 h at room temperature the reaction was quenched by water addition (8 mL) and extracted with CH$_2$Cl$_2$ (3×10 mL). The collected organic phases were washed with brine (10 mL), dried over dry Na$_2$SO$_4$ and concentrated in vacuo. Purification by silica gel chromatography (hexane/ethyl acetate 90:10 as eluent) gave intermediate 4 as a pale yellow solid (60 mg, 65%). $^1$H-NMR (CDCl$_3$, TMS) δ (ppm): 1H-NMR (CDC$_3$) δ (ppm): 10.05 (br s), 7.74-7.64 (m, 2H), 7.42-7.36 (m, 1H), 7.20-7.16 (m, 1H); MS (ES$^{1+}$) m/z: 221 (M+1).

5. Preparation of 2-(3-fluorophenyl)-5-(1H-tetrazol-5-yl)-1,3-thiazol-4-ol (intermediate 5)

A microwave vial was charged with intermediate 4 (60 mg, 0.27 mmol) and 2 mL of a solution of N-methyl pyrrolidone/AcOH 5:2 v/v. Then a 5.2 M solution of sodium azide (130 μL, 0.68 mmol) was added and the resulting mixture irradiated at 220° C. for 5 minutes. The reaction was quenched with 10 mL of water and extracted with ethyl acetate. The organic layer was separated and the aqueous one extracted again twice with ethyl acetate. The combined organic layers were dried over dry Na$_2$SO$_4$ and concentrated in vacuo. 2-(3-fluorophenyl)-5-(1H-tetrazol-5-yl)-1,3-thiazol-4-ol was obtained as white solid (61 mg, 86%) after preparative HPLC purification. $^1$H-NMR (DMSO-d$_6$) δ (ppm): 13.30 (br s, 1H), 12.10 (br s, 1H), 7.84-7.80 (m, 1H), 7.76-7.72 (m, 1H), 7.66-7.58 (m, 1H), 7.45-7.36 (m, 1H); MS (ES$^{1+}$) m/z: 264 (M+1).

6. Preparation of 5-(2-ethyl-2H-tetrazol-5-yl)-2-(3-fluorophenyl)-1,3-thiazol-4-ol (compound 118)

A 25 mL one-necked round bottom flask was charged with intermediate 5 (150 mg, 0.57 mmol) dissolved in 10 mL of acetonitrile. Triethylamine (79 μL, 0.56 mmol) and ethyl iodide (91 μL, 1.14 mmol) were added to the solution and the mixture was allowed to stir at room temperature overnight. The acetonitrile was evaporated and the crude diluted with water and washed with ethyl acetate (2×15 mL). The combined organic layers were dried over dry Mg$_2$SO$_4$ and concentrated in vacuo. The two resulting N-ethyl regioisomers were separated by preparative HPLC. Compound 1 was obtained as pale yellow solid (66 mg, 40%). $^1$H-NMR (DMSO-d$_6$) δ (ppm): 12.00 (br s, 1H), 7.84-7.78 (m, 1H), 7.76-7.72 (m, 1H), 7.66-7.58 (m, 1H), 7.45-7.36 (m, 1H), 4.75 (q, 2H, J=7.5), 1.50 (t, 3H, J=7.5); MS (ES$^{1+}$) m/z: 292 (M+1).

Example 119

Evaluation of In Vitro Activity
a. Cloning, Sequencing, Transfection and Selection of Positive Clones Expressing Human TRPM8

A functional cell-based assay for the identification of TRPM8 receptor antagonists, optimised to allow high throughput screening at FLIPR$^{TETRA}$, was developed in HEK293 cells by stable pure clone selection and functional characterization with a fluorescent calcium sensitive dye.

TRPM8 was cloned into the multiple clonig site of pcDNA3 mammalian expression vector; the obtained construct pcDNA3/hTRPM8 was fully sequence verified and used for the transfection of HEK293 cell line. HEK293 cells stably transfected with TRPM8 gene were maintained in Minimum essential medium. The cells were transfected with the pcDNA3/hTRPM8 vector by electroporation and then selected with medium containing 0.8 mg/ml G418 for 10-15 days.

The following commercial compounds were used as TRPM8 channel reference compound to test HEK293/hTRPM8 cell line for both agonist and antagonist activity:
Activators: Menthol (SIGMA cat. # M2772) WS-3, (N-Ethyl-5-methyl-2-(1-methylethyl) cyclohexanecarboxamide) (SIGMA cat. # W345501)
Blocker: Capsazepine (SIGMA cat. # C191)

The experimental activities were performed using FLIPR instruments.

The functional clones were selected at FLIPR$^{384}$ on the basis of 1 mM menthol response. Two best responder clones were selected, diluted at a cell density of 1 cell/well and analysed at FLIPR$^{384}$ with 1 mM menthol.

The TRPM8 receptor was analysed for the response to reference agonist, menthol, using a calcium-dependent fluorescence signal.

Patch clamp recordings were also obtained in voltage-clamp configuration on HEK/TRPM8 clones in order to verify the receptor pharmacology and to determine the agonist dose-response curve and EC$_{50}$ value. HEK293 cells were maintained at room temperature on an fire-polished borosilicate glass pipettes having 1.5-2.5 MΩ resistance were used to record currents following drug application. Menthol application induced a dose-dependent inward current in a selected HEK/hTRPM8 clone (calculated EC$_{50}$ value=58 μM). No menthol-induced currents were recorded in not transfected HEK293 cells.

In order to determine the capsazepine antagonist activity on menthol agonist response and to verify the antagonist response stability throughout different days of experiments, the selected clone of TRPM8 was analysed after 24 h at FLIPR$^{384}$ in presence of variable concentrations of antagonist (from 100 nM to 316 μM).

The selected clone showed very good stability and reproducibility of the antagonist activity (calculated IC$_{50}$ value=20 μM).

Summarizing, the best clone was characterized for:
1—pharmacology: agonist EC$_{50}$ and antagonist IC$_{50}$ determination over different experiments;
2—optimal cell density and seeding time;
3—DMSO sensitivity;
4—ligand stability;
5—patch clamp analysis.

b. Screening Set Up for the Identification of TRPM8 Antagonists

The following commercial compounds were used as ligands:
Activator: Cooling Agent 10 (Takasago CAS N. 87061-04-9)
Blocker: Capsazepine (SIGMA cat # D_5879)

The experimental activities were performed using FLIPR$^{TETRA}$ instruments.

HEK293 cells stably transfected with TRPM8 gene were maintained in Minimum essential medium.

The TRPM8 cell line was analysed for the response to a library of compounds using a $Ca^{2+}$ mobilization-dependent fluorescence signal in 384 wells microtiter plate format. The analysis was performed using the FLIPR$^{TETRA}$ (MDC) with the ICCD Camera.

The execution of the assay involved the use of three microtiter plates:
1. Assay plate, containing cells loaded with dye and prepared as follows:

Cells were seeded at 15000 c/well in Poly-D-Lysine coated 384 wells Microtiter Plates in complete medium (25 µl/well).

24 h after seeding, the cell plates were washed with Tyrode assay buffer by the Microplate Washer and 10 µL of Tyrode assay buffer was left in each well.

Cells were then loaded with 10 µL/well of the Fluo-4 NW dye solution by CyBi®-Well pipettor. Each bottle of Fluo4-NW dye (Molecular Probes cat. #F36206, component A) was re-suspended in 8 mL of Tyrode assay buffer and supplemented with 100 µL of water-soluble probenecid (MolecularProbes cat. #F36206, component B).

Dye loaded cell plates were incubated for 1 h at room temperature.
2. Compound Dilution Plate (FIG. 1), containing diluted test compounds, formulated as follows:

Column 1: wells containing Assay Buffer plus DMSO 0.5% final

Column 2: wells alternating Max Signal Control in first injection (Maximum Response: Cooling Agent 10 at $EC_{100}$, 100 µM) and Min Signal Control in first injection (Assay buffer plus 0.5% DMSO final);

Columns 3-22: wells containing Assay Buffer plus 0.5% DMSO final. To these wells the compounds to be tested were added at 3× concentration.

Column 23: alternating wells of Max Signal Control in second injection (Assay buffer) and Min Signal Control in second injection (Antagonist Capsazepine $IC_{100}$, 50 µM) in Assay buffer plus 0.5% DMSO final;

Column 24: wells containing Capsazepine (Antagonist) at 8 concentrations in duplicate at final concentrations of 50 µM, 25 µM, 6.25 µM, 3.15 µM, 1.56 µM, 780 nM, 309 nM in Assay buffer plus 0.5% DMSO final.
3. Activator Plate (FIG. 2), containing agonist Cooling Agent 10 at EC80, formulated as follows:

Column 1: Cooling Agent 10 (Agonist) at 8 concentrations dose response in duplicate at final concentrations of 100 µM, 31.6 µM, 10 µM, 3.16 µM, 1 µM, 316 nM, 100 nM, 31.6 nM in Assay buffer;

Columns 2-24: Cooling Agent 10 (Agonist) at $EC_{80}$ (3 fold concentrated, 20 µM final) in Assay buffer.

The test was carried out according to a procedure comprising the following steps:
1. The samples contained in the wells of the Compound Plate were added to the corresponding wells of the Assay Plate by the FLIPR$^{TETRA}$, thus resulting in the addition in Columns 3-22 of the test compounds at 3× concentration to the cells of the assay plates. No mixing was performed in the assay wells and the signal of the emitted fluorescence was recorded for 300 seconds.
2. The samples contained in the wells of the Activator Plate were added to the corresponding wells of the Assay Plate by the FLIPR$^{TETRA}$, thus resulting in the addition in Columns 3-22 of the Assay Plate of the agonist compound in addition to the test compounds. The signal of the emitted fluorescence was recorded for 180 seconds.

Columns 1, 2, 23 and 24 were used as control. In particular: the "Max Signal Control in first injection" indicates the Cooling Agent 10 agonist response at $EC_{100}$, "Max Signal Control in the second injection" indicates the agonist at $EC_{80}$ (10 µM) in presence of pre-injected Assay buffer, the "Min Signal Control in first injection" corresponds to Assay buffer injection and "Min Signal Control in the second injection" indicates the agonist at $EC_{80}$ (20 µM) in presence of pre-injected reference antagonist Capazepine at $IC_{100}$ (50 µM).

FIG. 3 represents a typical kinetic response graph obtained with all the compounds of Table IV.

During the Target Activation (TA) phase, the injection of the reference agonist at $EC_{80}$ gave an increase of fluorescent signal in MAX Signal control wells in which the assay buffer in CA was preinjected, while the response was completely inhibited in MIN Signal control wells due to the preinjection of the reference inhibitor Capsazepine.

The goal of the assay was to find antagonists of TRPM8 activity; to this aim the change of fluorescent signal during TA phase was measured.

Several parameters were computed and analyzed (Z' factor, Interplate variability, Intraplate variability, Day to Day variability, Antagonist Dose response and $IC_{50}$ determination, Agonist Dose response and $EC_{50}$ determination).

As for the antagonist Dose response and $IC_{50}$ determination, capsazepine (reference antagonist) was included as control and the $IC_{50}$ values of all the assayed compounds were calculated.

Compounds 1-118 were tested and all showed an $IC_{50}$ value<30 µM; in particular, compounds n. 1, 2, 5, 8, 9, 27, 36, 41, 43, 67, 68, 70, 83, 84 were characterized by an $IC_{50}$ value<10 µM; compounds n. 10 and 45 showed an $IC_{50}$ value=1 µM and 0.0002 µM, respectively.

c. Calcium Influx Assay

The ability of compounds n. 10 and 45 to act as TRPM8 antagonists was also evaluated with a calcium influx assay. The effects of 7 concentrations (0.00001, 0.0001, 0.001, 0.01, 0.1, 1, and 10 µM) of compounds 10, 45 and 118 were evaluated on TRPM8 using the following experimental procedure.

Channels were activated with menthol, as the positive control agonist, and the ability of test compound to inhibit this signal was examined and compared to the positive control antagonist, 2-APB (inserire dettagli composto). The signal elicited in the presence of the positive control agonist (10 µM menthol) was set to 100% and the signal in the presence of the positive control antagonist (200 µM 2-APB) was set to 0. The $pIC_{50}$ values of the compound 10 45 and 118 were 9.7, 6 and 7.7 respectively. Values were considered significant if the test compound mean was three or more standard deviations away from the positive control agonist mean.

Example 120

Evaluation of In Vivo Activity
a. Isovolumetric Bladder Model

Female rats were anesthetized with urethane. Ureters were ligated and sectioned. A catheter was inserted through the urinary meatus into the bladder before urethral ligature. The bladder was filled first 3 times every 5 min with 100 μL of a solution of solutol/NMP (2:1 w/w) containing 0.1 mg of compounds n. 10 or 45 or with 100 μL of vehicle, then with 100 μL of saline every 5 min until the occurrence of rhythmic bladder contraction (RBC). A maximal volume of 3 mL was infused. The intravesical pressure was followed during 1 h30 after RBC appearance. For each group, Threshold Volume (TV), Micturition Frequency (MF) and Amplitude of Micturition (AM) were measured during the whole period. In the group treated with compound 10 the threshold volume (TV) was significantly increased compared to the group treated with the solvent reaching 1.5 mL of volume whereas, in the vehicle group, RBC occurred in all rats with a mean volume of 0.7±0.09 mL. Compound 10 did not change AM. No effect on the total MF (measured during 90 min) was observed.

Both the molecules showed significant efficacy in the isovolumetric model in inhibiting rhythmic bladder contractions and micturition frequency. In particular, the systemic treatment with compound 10 (10 mg/kg i.v.) significantly reduced Micturition Frequency (MF) of about 36% in the first 30 min of the experiment. On the other hand, when administered by intravesical route at 2.3 mg/rat, compound 10 completely abolished the continuous RBC induced by the filling of the bladder with saline. In addition, compound 10 (2.3 mg/rat) and compound 45 (0.3 mg/rat) significantly increased the threshold volume (equivalent to the bladder capacity), reaching a higher volume of 1.5-3.0 mL if compared to that of 0.7±0.9 mL of the vehicle group. Both the compounds did not change Amplitude of Micturition (AM) when compared to basal values, suggesting that they are selective for the afferent arm of micturition reflex with no effect on the efferent pathway.

b. Chronic Constriction Model of Pain-Compounds 10 and 45

Male Sprague-Dawley rats were used. Under pentobarbital anesthesia, the sciatic nerve was exposed at mid-thigh level (Bennett G J et al Pain. 33: 87-107, 1988). Four ligatures were loosely tied around the sciatic nerve of the left hind limb to induce enhancement of pain caused by nerve injury. Mechanical allodynia was evaluated by using a set of 8 manual von Frey monofilaments (0.4, 0.6, 1, 2, 4, 6, 8 and 15 g) 18 days after surgery and basal response was recorded.

On day 19 body weight was recorded and compounds 10 and 45 were administered by i.v. route at the dose of 10 mg/kg. 60, 120 and 180 min post dose, mechanical allodynia was tested by evaluation of the Paw Withdrawl Threshold (PWT) and % Maximum Possible Effect (MPE) was calculated according to the following formula:

$$\% \, MPE = \frac{(\text{Log } PWT \text{ of test-Avg Log } PWT \text{ of baseline predrug})}{(\text{Log } (15)\text{-Avg log } PWT \text{ of baseline predrug})} * 100$$

The mechanical allodynia was tested 1 day before treatment and at 2 hours post-dosing. One-way ANOVA followed by Dunnett's test was applied for comparison between vehicle control and test compound treated groups. *p<0.05 is considered significant.

Compounds 10 and 45 showed a significant anti-allodynic activity at 2 hours post-dosing in CCI rats (see FIG. 4).

Example 121

Evaluation of In Vivo Activity for Compound 118
Chronic Constriction Model of Pain
Animals Male Wistar rats (220-250 g, Harlan Italy) were used (n=60). Animals were housed in a room with controlled temperature (22±1° C.), humidity (60±10%) and light (12 h per day) for at least a week before being used. Rats were randomly divided into sham, control and treatment groups; ten animals per group were used. All animal experiments were complied with the Italian (D. L. no. 116 of Jan. 27, 1992) and associated guidelines in the European Communities Council (Directive of Nov. 24, 1986, 86/609/ECC).

Drug Treatment

Compound 118 (10 mg/kg; 5 mg/ml; 0.5 ml/iv/rat) was dissolved in 10% solutol-HS15 and N-Methylpyrrolidone (NMP) (SOLUTOL:NMP 2:1 w/v) and 90% Phosphate Buffered Saline (PBS) 1×, and was administered at day $3^{rd}$, $7^{th}$ and $14^{th}$ following sciatic nerve ligation. Antiallodynic effects were assessed at 1 and 3 h post dose. Control animals received vehicle alone (0.5 ml/iv/rat; 10% solutol-NMP and 90% PBS).

Chronic Constriction Injury (CCI) Model of Neuropathic Pain

Neuropathic pain behavior was induced by ligation of the sciatic nerve according to the method described by Bennett and Xie [Bennett G. J. and Xie Y. K. A peripheral mononeuropathy in rat that produces disorders of pain sensation like those seen in man, Pain, (1988) 33:87-107]. Briefly, rats were anaesthetized (100 mg/kg ketamine and 10 mg/kg xylazine i.p.) and the left sciatic nerve was exposed at the level of the thigh by blunt dissection through the biceps femoris. Proximal to the sciatic's trifurcation, about 12 mm of nerve was freed of adhering tissue and four ligatures were loosely tied around it with about 1 mm spacing so that the epineural circulation was preserved. The length of nerve thus affected was 6-8 mm long. The animals were allowed to recover and used the day after the surgery. Sham animals represent rats operated but not ligated.

Mechanical Allodynia

To assess for changes in sensation or in the development of mechanical allodynia, sensitivity to tactile stimulation was measured using the Dynamic Plantar Aesthesiometer (DPA, Ugo Basile, Italy). Ligated animals were placed in a chamber with a mesh metal floor covered by a plastic dome that enabled the animal to walk freely, but not to jump. The mechanical stimulus was then delivered in the mid-plantar skin of the hind paw. The cut-off was fixed at 50 g, while the increasing force rate (ramp duration) was settled at 20 sec. The DPA automatically records the force at which the foot was withdrawn and the withdrawal latency. Each paw was tested twice per session. This test did not require any special pre-training, just an acclimation period to the environment and testing procedure. Testing was performed on both the ispsilateral (ligated) and contralateral (unligated) paw before ligation (day 0) and then on $3^{rd}$, $7^{th}$ and $14^{th}$ days after ligation.

Cold Allodynia

Cold sensitivity was measured as the number of foot withdrawal responses after application of acetone to the dorsal surface of the paw. A drop of acetone (15-20° C.) was applied to the dorsal surface of the ligated paw with a syringe connected to a thin polyethylene tube while the rats were standing on a metal mesh. A brisk foot withdrawal response, after the spread of acetone over the dorsal surface of the paw, was considered as a sign of cold allodynia. Basal response was measured on the days before treatment ($2^{nd}$, $6^{th}$ and $13^{th}$). Data represents mean±SEM of 3 measurements performed at an interval of approximately 5 min.

Statistical Analysis

All data was presented as the mean±SEM. Analysis of data was conducted using GraphPad Prism 4.01. Statistical analysis was performed by two-way ANOVA followed by Bonferroni's test for multiple comparisons, as appropriate. Statistical significance was set at p<0.05.

Results

Intravenous administration of Compound 118 (10 mg/kg) on day 7 after nerve-induced injury significantly attenuated cold and mechanical allodynia at 1 hour post-dose. The results obtained reflected, as expected, a higher activity of Compound 1 to cold stimulus compared to mechanical stimulus (39% of inhibition and 26% of inhibition, respectively).

On day 14 after surgery, the inhibitory activity of Compound 118 was still statistically significant at 1 h post-dose on cold stimulus (52% of inhibition), even if no inhibition on mechanical stimulus could be observed; on the contrary, the reference compound maintained a statistically significant inhibitory effect both on cold and mechanical allodynia (51% and 26% respectively at 1 h after administration).

Example 122

Selectivity Analysis

The objective of this study was to evaluate the in vitro effects of compounds 10 and 45 on cloned human GPCRs (G-protein coupled receptors) expressed in HEK293 or CHO cells using radioligand binding assays (compound concentration=10 μM).

Three replicates were performed for each experiment.

For each assay a concentration-response curve of the appropriate reference compound was performed in each experiment. The sample radioactivity content was measured after the addition of the scintillation cocktail Microscint 20 (PerkinElmer), by a microplate scintillation Beta-counter TopCount NXT (PerkinElmer). The atomic disintegrations per minutes evaluated with the beta counter were about 15 times higher than those found using the gamma counter. Data are expressed as percentage of control binding value (% B) and test compound inhibition was considered significant when % AB was <75% at 10 μM.

TABLE I

| Receptor | Cmpd 10 (% B) | Cmpd 45 (% B) |
|---|---|---|
| human Muscarinic $M_2$ Receptor | 90 | 96 |
| human Muscarinic $M_3$ Receptor | 98 | 95 |
| human Adrenergic $\beta_1$ Receptor | 82 | 90.53 |
| human Adrenergic $\beta_2$ Receptor | 88 | 93 |
| human Adrenergic $\alpha_{1A}$ Receptor | 100 | 96 |
| human Adrenergic $\alpha_{2A}$ Receptor | 100 | 100 |
| human Serotoninergic 5-$HT_{1A}$ Receptor | 100 | 100 |
| human Histamine $H_1$ Receptor | 99.3 | 100 |
| human Histamine $H_2$ Receptor | 90 | 93.2 |
| human Cannabinoid $CB_2$ Receptor | 102 | 86.7 |
| human Bradykinin $B_1$ Receptor | 91 | 99.6 |
| human Dopamine $D_{2S}$ Receptor | 100 | 100 |
| human Dopamine $D_3$ Receptor | 87 | 97.2 |

As it is possible to note from Tab I, both compounds show no binding versus a wide range of selected GPCRs (including muscarinic M3, CB2, BK1, alpha e beta adrenergic) that are well know to be involved in the pain control. These data support that the observed in vivo efficacy of compounds 10, 45 and 118 and in general of all the compounds of the invention is strongly dependent on the TRPM8 blockage.

In order to address more specifically the potential selectivity issues, a counterassay was carried out for 10, 45 and 118 against TRPV1 and TRPV4 ion channels, both involved in the nociception (Jhaveri M D, et al 2005. *Eur. J. Neurosci.* 22 (2): 361-70, Brierley S M et al, 2008, *Gastroenterology.* 2008 June; 134(7):2059-69.).

The ability of each test compound to act as an antagonist of TRPV1 was evaluated with a calcium influx assay. The signal elicited in the presence of the positive control agonist (0.1 μM capsaicin) was set to 100% and the signal in the presence of the antagonist (5 μM ruthenium red) was set to 0. The normalized % inhibition of the test articles is shown in Table below. Values were considered significant if the test article mean was three or more standard deviations away from the positive control agonist mean.

In parallel, the ability of each test compound to act as an antagonist of TRPV4 was evaluated with a calcium influx assay. The signal elicited in the presence of the positive control agonist (10 μM GSK1016790A) was set to 100% and the signal in the presence of the antagonist (5 μM ruthenium red) was set to 0. The normalized % inhibition of the test articles is shown in Table below. Values were considered significant if the test compound mean was three or more standard deviations away from the positive control agonist mean (i.e., greater than 31.70% inhibition for plate 1 and 24.60% inhibition for plate 2).

TABLE II

| Cmpd (10 and 1 uM) | Test Conc. | Normalized % inhibition (TRPV1) | Normalized % inhibition (TRPV4) |
|---|---|---|---|
| 10 | 1 | 1.2 | 2.0 |
|  | 10 | 2.3 | 8.9 |
| 45 | 1 | 3.1 | 5.1 |
|  | 10 | 6.3 | 3.1 |
| 118 | 1 | 1.2 | 2.0 |
|  | 10 | 2.3 | 8.9 |

The data strongly highlight the great selectivity of molecules 10, 45 and 118 towards both TRPV1 and TRPV4, thus confirming their selective mechanism of action.

Example 123

ADME Evaluation

The pharmacokinetic profiles of compounds 10 and 45 were evaluated. The result are summarised in Table III:

TABLE III

| Compound 10 | | | | | | | |
|---|---|---|---|---|---|---|---|
| Log D | CYP (% inhibition) @10 μM | | hERG binding @10 μM | Microsome stability (% remaining) @1 μM | $t_{1/2}$ i.v. rat (min) | Plasma Protein Binding (% @10 μM) | |
| 1.59 | 1A2 | <5 | No effect | rat 45 | 50 | rat 98 | |
|  | 2C9 | <5 |  |  |  |  | |
|  | 2C19 | <5 |  | human 55 |  | human 97 | |
|  | 2D6 | <5 |  |  |  |  | |
|  | 3A4 | <5 |  |  |  |  | |

TABLE III-continued

Compound 45

| Log D | CYP (% inhibition) @10 μM | hERG binding @10 μM | Plasma stability (% remaining) @10 μM | $t_{1/2}$ i.v. rat (min), F(%) | Plasma Protein Binding (% @10 μM) |
|---|---|---|---|---|---|
| 2.7 | 1A2 <5<br>2C9 <5<br>2C19 <5<br>2D6 <5<br>3A4 <5 | No effect | rat 95<br>human 100 | 240, 60 | rat 99<br>human 99 |

All three molecules show no effect towards any human cytochrome isoform at the maximal concentration of 10 μM thus excluding potential drug drug interaction.

In addition, no effect was observed towards hERG channel thus excluding potential cardiotoxic effect during the clinical development.

The low log D values of compounds 10 and 118 make them particularly suitable when ip, iv and i ves applications are required, especially in the treatment of urological disorders. At the same time, the relatively high plasma half-life (4 h) and the high oral bioavailability (F=60%) could makes it the ideal candidate for the treatment of chronic diseases, like inflammatory and neuropathic pain.

TABLE IV

| Compound | X | R¹ | R² | R³ | R⁴ |
|---|---|---|---|---|---|
| 1 | S | OH | COOH | H | p-Cl |
| 2 | S | OH | COOH | H | p-CH₃ |
| 3 | S | OH | COOH | H | m-F |
| 4 | S | OH | COOH | H | p-F |
| 5 | S | OH | COOCH₃ | H | H |
| 6 | S | OH | COOCH₃ | 2-F | 4-F |
| 7 | S | OH | COOCH₂CH₃ | H | H |
| 8 | S | OH | COOCH₂CH₃ | H | p-Cl |
| 9 | S | OH | COOCH₂CH₃ | H | p-CH₃ |
| 10 | S | OH | COOCH₂CH₃ | H | m-F |
| 11 | S | OH | COOCH₂CH₃ | H | p-F |
| 12 | S | OH | COOCH₂CH₃ | H | 4-pyridyl |
| 13 | S | OH | COOCH₂CH₃ | H | p-N(CH₃)₂ |
| 14 | S | OH | COOCH₂CH₃ | H | m-Cl |
| 15 | S | OH | COOCH₂CH₃ | H | m-(2-CF₃—C₆H₅) |
| 16 | S | OH | COOCH₂CH₃ | H | m-(2-F—C₆H₅) |
| 17 | S | OH | COOCH₂CH₃ | H | p-(2-CF₃—C₆H₅) |
| 18 | S | OH | COOCH₂CH₃ | H | p-(2-F—C₆H₅) |
| 19 | S | OH | COOCH₂CH₃ | H | p-(2-F—OCH₂C₆H₅) |
| 20 | S | OH | COOCH₂CH₃ | H | p-(4-F—OCH₂C₆H₅) |
| 21 | S | F₃CSO₂O | COOCH₂CH₃ | H | p-F |
| 22 | S | OCH₃ | COOCH₂CH₃ | H | p-CH₃ |
| 23 | S | isobutyl-O- | COOCH₂CH₃ | H | p-CH₃ |
| 24 | S | benzyl-O- | COOCH₂CH₃ | H | H |
| 25 | S | (3-Cl-benzyl)-O- | COOCH₂CH₃ | H | p-Cl |
| 26 | S | (3-Cl-benzyl)-O- | COOCH₂CH₃ | H | m-F |

TABLE IV-continued
| Compound | X | R¹ | R² | R³ | R⁴ |
|---|---|---|---|---|---|
| 27 | S | 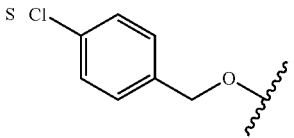 | COOCH$_2$CH$_3$ | H | H |
| 28 | S | 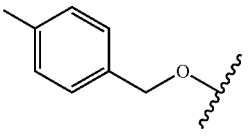 | COOCH$_2$CH$_3$ | H | m-Cl |
| 29 | S | 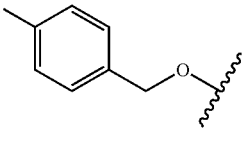 | COOCH$_2$CH$_3$ | H | p-CH$_3$ |
| 30 | S | 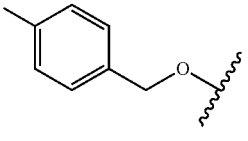 | COOCH$_2$CH$_3$ | H | m-F |
| 31 | S | 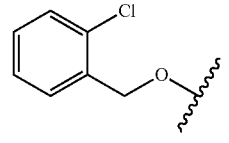 [SMILES: *OCc1ccccc1Cl] | COOCH$_2$CH$_3$ | H | H |
| 32 | S | 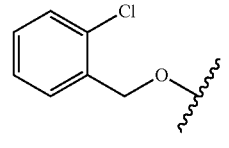 [SMILES: *OCc1ccccc1Cl] | COOCH$_2$CH$_3$ | H | p-F |
| 33 | S | 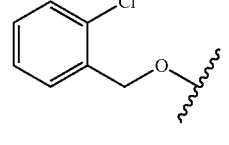 | COOCH$_2$CH$_3$ | H | p-Cl |
| 34 | S | 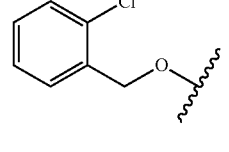 | COOCH$_2$CH$_3$ | H | m-Cl |
| 35 | S | 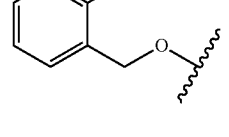 | COOCH$_2$CH$_3$ | H | p-CH$_3$ |
| 36 | S | 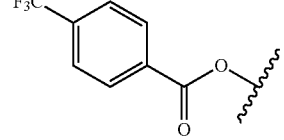 | COOCH$_2$CH$_3$ | H | H |

TABLE IV-continued

| Compound | X | R¹ | R² | R³ | R⁴ |
|---|---|---|---|---|---|
| 37 | S | 4-(F₃C)-C₆H₄-C(O)O- | COOCH₂CH₃ | H | m-F |
| 38 | S | 4-(F₃C)-C₆H₄-C(O)O- | COOCH₂CH₃ | H | p-CH₃ |
| 39 | S | menthyl-O-CH₂-C(O)O- | COOCH₂CH₃ | H | p-CH₃ |
| 40 | S | PhCH₂-NH-C(O)O- | COOCH₂CH₃ | H | p-Cl |
| 41 | S | H₂N-CH₂CH₂-O- | COOCH₂CH₃ | H | p-Cl |
| 42 | S | furan-2-yl-CH₂-NH-CH₂CH₂-O- | COOCH₂CH₃ | H | p-Cl |
| 43 | S | 4-Cl-C₆H₄-CH₂-O- | COOH | H | p-CH₃ |
| 44 | S | 4-Cl-C₆H₄-CH₂-O- | COOH | H | H |
| 45 | S | 4-Cl-C₆H₄-CH₂-O- | COOH | H | p-Cl |
| 46 | S | 4-Cl-C₆H₄-CH₂-O- | COOH | H | m-Cl |

TABLE IV-continued

| Compound | X | R¹ | R² | R³ | R⁴ |
|---|---|---|---|---|---|
| 47 | S | benzyl-O- | COOH | H | H |
| 48 | S | 3-Cl-benzyl-O- | COOH | H | m-F |
| 49 | S | 2-Cl-benzyl-O- | COOH | H | H |
| 50 | S | 2-Cl-benzyl-O- | COOH | H | p-F |
| 51 | S | 2-Cl-benzyl-O- | COOH | H | p-Cl |
| 52 | S | 2-Cl-benzyl-O- | COOH | H | m-Cl |
| 53 | S | 2-Cl-benzyl-O- | COOH | H | p-CH₃ |
| 54 | S | 2-Cl-benzyl-O- | COOH | H | m-F |
| 55 | S | 4-F₃C-benzyl-O- | COOH | H | H |
| 56 | S | 4-F₃C-benzyl-O- | COOH | H | m-F |

TABLE IV-continued

| Compound | X | R¹ | R² | R³ | R⁴ |
|---|---|---|---|---|---|
| 57 | S | 4-(CF₃)-C₆H₄-C(O)O- | COOH | H | H |
| 58 | S | 4-(CF₃)-C₆H₄-C(O)O- | COOH | H | m-F |
| 59 | S | 4-(CF₃)-C₆H₄-C(O)O- | COOH | H | p-CH₃ |
| 60 | S | OCH₃ | COOH | H | p-CH₃ |
| 61 | S | isobutyl-O- | COOH | H | p-CH₃ |
| 62 | S | (CH₃)₃C-O-C(O)-NH- | COOCH₂CH₃ | H | p-F |
| 63 | S | NH₂ | COOCH₂CH₃ | H | p-F |
| 64 | S | CH₃-C(O)-NH- | COOCH₂CH₃ | H | p-CH₃ |
| 65 | S | 4-(CF₃)-C₆H₄-C(O)-NH- | COOCH₂CH₃ | H | p-CH₃ |
| 66 | S | C₆H₅-NH-C(O)-NH- | COOCH₂CH₃ | H | p-CH₃ |
| 67 | S | H₂N-CH₂CH₂-NH- | COOCH₂CH₃ | H | p-CH₃ |
| 68 | S | CH₃-NH-CH₂CH₂-NH- | COOCH₂CH₃ | H | p-Cl |

TABLE IV-continued
| Compound | X | R¹ | R² | R³ | R⁴ |
|---|---|---|---|---|---|
| 69 | S | 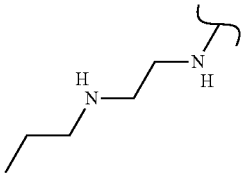 | COOCH₂CH₃ | H | p-Cl |
| 70 | S | 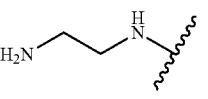 | COOCH₂CH₃ | H | p-Cl |
| 71 | S | 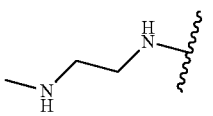 [SMILES: *NCCNC] | COOCH₂CH₃ | H | p-CH₃ |
| 72 | S | 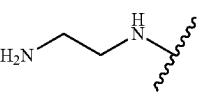 | COOCH₂CH₃ | H | p-(2-CF₃—C₆H₅) |
| 73 | S | 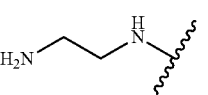 [SMILES: *NCCN] | COOCH₂CH₃ | H | m-(2-CF₃—C₆H₅) |
| 74 | S | 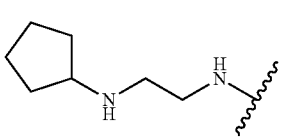 [SMILES: *NCCNC1CCCC1] | COOCH₂CH₃ | H | p-Cl |
| 75 | S | 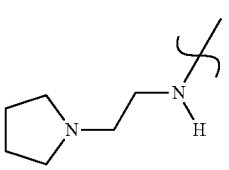 | COOCH₂CH₃ | H | H |
| 76 | S | 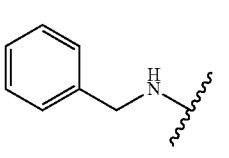 [SMILES: *NCc1ccccc1] | COOCH₂CH₃ | H | m-F |
| 77 | S | 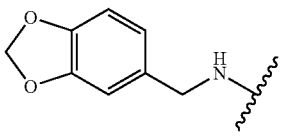 [SMILES: *NCc1ccc2c(c1)OCO2] | COOCH₂CH₃ | H | m-F |
| 78 | S | 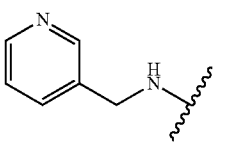 [SMILES: *NCc1cccnc1] | COOCH₂CH₃ | H | m-F |
| 79 | S | 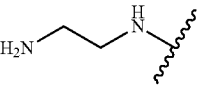 | COOH | H | p-CH₃ |
| 80 | S | 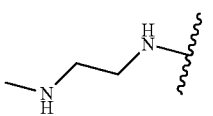 [SMILES: *NCCNC] | COOH | H | p-CH₃ |

TABLE IV-continued

| Compound | X | R¹ | R² | R³ | R⁴ |
|---|---|---|---|---|---|
| 81 | S | H₂N-CH₂-CH₂-NH- | COOH | H | m-F |
| 82 | S | 3-Cl-C₆H₄-CH₂-O- | COONa | H | m-F |
| 83 | S | 4-Cl-C₆H₄-CH₂-O- | COONa | H | p-CH₃ |
| 84 | S | 4-Cl-C₆H₄-CH₂-O- | COONa | H | p-Cl |
| 85 | S | 2-Cl-C₆H₄-CH₂-O- | COONa | H | p-Cl |
| 86 | S | 2-Cl-C₆H₄-CH₂-O- | COONa | H | p-CH₃ |
| 87 | S | 2-Cl-C₆H₄-CH₂-O- | COONa | H | m-F |
| 88 | S | 4-Cl-C₆H₄-CH₂-O- | COONa | H | m-F |
| 89 | S | C₆H₅-CH₂-O- | menthyl ester | H | p-CH₃ |

TABLE IV-continued

| Compound | X | R¹ | R² | R³ | R⁴ |
|---|---|---|---|---|---|
| 90 | S | OH | menthyl ester group (isopropyl, methyl cyclohexyl -O-C(=O)-) | H | p-cH₃ |
| 91 | S | CH₃O-CH₂-O- | COOCH₂CH₃ | H | p-Cl |
| 92 | S | CH₃O-CH₂-O- | COOH | H | p-Cl |
| 93 | S | CH₃O-CH₂-O- | C(O)NH₂ | H | p-Cl |
| 94 | S | CH₃O-CH₂-O- | CN | H | p-Cl |
| 95 | S | OH | 1H-tetrazol-5-yl | H | p-Cl |
| 96 | S | OH | 1-methyl-tetrazol-5-yl | H | p-Cl |
| 97 | S | OH | 1-methyl-tetrazol-5-yl | H | m-F |
| 98 | S | OH | 3-methyl-4H-1,2,4-triazol-5-yl | H | p-Cl |
| 99 | S | OH | 3-methyl-4H-1,2,4-triazol-5-yl | H | m-F |
| 100 | S | OH | 5-methyl-1,2,4-oxadiazol-3-yl | H | p-Cl |
| 101 | S | OH | 5-methyl-1,2,4-oxadiazol-3-yl | H | m-F |

TABLE IV-continued
| Compound | X | R¹ | R² | R³ | R⁴ |
|---|---|---|---|---|---|
| 102 | S | Cl 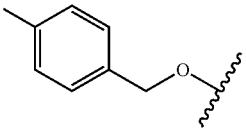 | 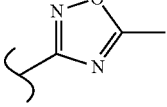 | H | m-F |
| 103 | S | OH | 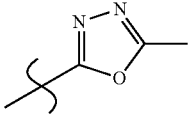 | H | p-Cl |
| 104 | S | OH | 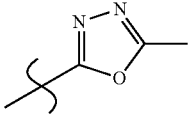 | H | m-F |
| 105 | O | OH | COOCH₂CH₃ | H | H |
| 106 | O | OH | COOCH₂CH₃ | H | m-F |
| 107 | O | OH | COOCH₂CH₃ | H | p-CH₃ |
| 108 | O | Cl 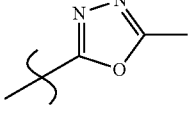 | COOCH₂CH₃ | H | H |
| 109 | O | Cl 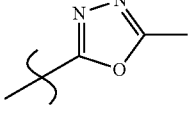 | COOCH₂CH₃ | H | m-F |
| 110 | O | Cl 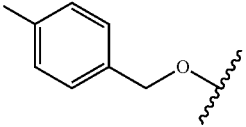 | COOCH₂CH₃ | H | p-CH₃ |
| 111 | O | F₃C 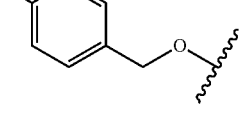 | COOCH₂CH₃ | H | H |
| 112 | O | Cl 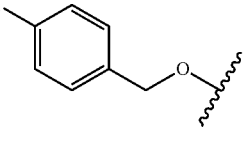 | COOH | H | H |
| 113 | O | Cl 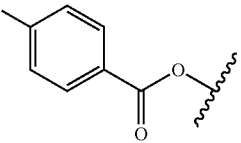 | COOH | H | m-F |
| 114 | O | Cl 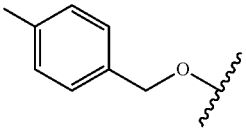 | COOH | H | p-CH₃ |

TABLE IV-continued

| Compound | X | R¹ | R² | R³ | R⁴ |
|---|---|---|---|---|---|
| 115 | O | OH | 3-methyl-1,2,4-oxadiazol-5-yl (methylene-linked) | H | m-F |
| 116 | O | Cl-C₆H₄-CH₂-O- (4-chlorobenzyloxy) | 3-methyl-1,2,4-oxadiazol-5-yl (methylene-linked) | H | m-F |
| 117 | S | OCOCH₂CH₃ | OH | H | p-CH₃ |
| 118 | S | OH | 2-ethyl-2H-tetrazol-5-yl (methylene-linked) | H | m-F |

The invention claimed is:
1. A compound selected from:
2-(4-chlorophenyl)-4-hydroxy-1,3-thiazole-5-carboxylic acid (1)
4-hydroxy-2-(4-methylphenyl)-1,3-thiazole-5-carboxylic acid (2)
2-(3-fluorophenyl)-4-hydroxy-1,3-thiazole-5-carboxylic acid (3)
2-(4-fluorophenyl)-4-hydroxy-1,3-thiazole-5-carboxylic acid (4)
methyl 2-(2,4-difluorophenyl)-4-hydroxy-1,3-thiazole-5-carboxylate (6)
ethyl 2-(3-fluorophenyl)-4-hydroxy-1,3-thiazole-5-carboxylate (10)
ethyl 2-(4-fluorophenyl)-4-hydroxy-1,3-thiazole-5-carboxylate (11)
ethyl-4-hydroxy-2-(4-pyridin-4-yl)phenyl-1,3-thiazole-5-carboxylate (12)
ethyl 2-[4-(dimethylamino)phenyl]-4-hydroxy-1,3-thiazole-5-carboxylate (13)
ethyl 4-hydroxy-2-[2'-(trifluoromethyl)biphenyl-3-yl]-1,3-thiazole-5-carboxylate (15)
ethyl 2-(2'-fluorobiphenyl-3-yl)-4-hydroxy-1,3-thiazole-5-carboxylate (16)
ethyl 4-hydroxy-2-[2'-(trifluoromethyl)biphenyl-4-yl]-1,3-thiazole-5-carboxylate (17)
ethyl 2-(2'-fluorobiphenyl-4-yl)-4-hydroxy-1,3-thiazole-5-carboxylate (18)
ethyl 2-{4-[(2-fluorobenzyl)oxy]phenyl}-4-hydroxy-1,3-thiazole-5-carboxylate (19)
ethyl 2-{4-[(4-fluorobenzyl)oxy]phenyl}-4-hydroxy-1,3-thiazole-5-carboxylate (20)
ethyl 2-(4-fluorophenyl)-4-{[(trifluoromethyl)sulfonyl]oxy}-1,3-thiazole-5-carboxylate (21)
ethyl 4-methoxy-2-(4-methylphenyl)-1,3-thiazole-5-carboxylate (22)
ethyl 2-(4-methylphenyl)-4-(2-methylpropoxy)-1,3-thiazole-5-carboxylate (23)
ethyl 4-(benzyloxy)-2-phenyl-1,3-thiazole-5-carboxylate (24)
ethyl 4-[(3-chlorobenzyl)oxy]-2-(4-chlorophenyl)-1,3-thiazole-5-carboxylate (25)
ethyl 4-[(3-chlorobenzyl)oxy]-2-(3-fluorophenyl)-1,3-thiazole-5-carboxylate (26)
ethyl 4-[(4-chlorobenzyl)oxy]-2-(4-methylphenyl)-1,3-thiazole-5-carboxylate (29)
ethyl 4-[(4-chlorobenzyl)oxy]-2-(3-fluorophenyl)-1,3-thiazole-5-carboxylate (30)
ethyl 4-[(2-chlorobenzyl)oxy]-2-(4-fluorophenyl)-1,3-thiazole-5-carboxylate (32)
ethyl 4-[(2-chlorobenzyl)oxy]-2-(4-chlorophenyl)-1,3-thiazole-5-carboxylate (33)
ethyl 4-[(2-chlorobenzyl)oxy]-2-(3-chlorophenyl)-1,3-thiazole-5-carboxylate (34)
ethyl 4-[(2-chlorobenzyl)oxy]-2-(4-methylphenyl)-1,3-thiazole-5-carboxylate (35)
ethyl 2-(3-fluorophenyl)-4-{[4-(trifluoromethyl)benzoyl]oxy}-1,3-thiazole-5-carboxylate (37)
ethyl 2-(4-methylphenyl)-4-{[4-(trifluoromethyl)benzoyl]oxy}-1,3-thiazole-5-carboxylate (38)
ethyl 4-(2-((1R,2S,5R)-2-isopropyl-5-methylcyclohexyloxy)acetoyloxy)-2-(4-methylphenyl)-1,3-thiazole-5-carboxylate (39)
ethyl 4-[(benzylcarbamoyl)oxy]-2-(4-chlorophenyl)-1,3-thiazole-5-carboxylate (40)
ethyl 4-(2-aminoethoxy)-2-(4-chlorophenyl)-1,3-thiazole-5-carboxylate (41)
ethyl 2-(4-chlorophenyl)-4-{2-[(furan-2-ylmethyl)amino]ethoxy}-1,3-thiazole-5-carboxylate (42)
4-[(4-chlorobenzyl)oxy]-2-(4-methylphenyl)-1,3-thiazole-5-carboxylic acid (43)
4-[(4-chlorobenzyl)oxy]-2-phenyl-1,3-thiazole-5-carboxylic acid (44)
4-[(4-chlorobenzyl)oxy]-2-(4-chlorophenyl)-1,3-thiazole-5-carboxylic acid (45)
4-[(4-chlorobenzyl)oxy]-2-(3-chlorophenyl)-1,3-thiazole-5-carboxylic acid (46)
4-(benzyloxy)-2-phenyl-1,3-thiazole-5-carboxylic acid (47)
4-[(3-chlorobenzyl)oxy]-2-(3-fluorophenyl)-1,3-thiazole-5-carboxylic acid (48)
4-[(2-chlorobenzyl)oxy]-2-phenyl-1,3-thiazole-5-carboxylic acid (49)
4-[(2-chlorobenzyl)oxy]-2-(4-fluorophenyl)-1,3-thiazole-5-carboxylic acid (50)

4-[(2-chlorobenzyl)oxy]-2-(4-chlorophenyl)-1,3-thiazole-5-carboxylic acid (51)
4-[(2-chlorobenzyl)oxy]-2-(3-chlorophenyl)-1,3-thiazole-5-carboxylic acid (52)
4-[(2-chlorobenzyl)oxy]-2-(4-methylphenyl)-1,3-thiazole-5-carboxylic acid (53)
4-[(2-chlorobenzyl)oxy]-2-(3-fluorophenyl)-1,3-thiazole-5-carboxylic acid (54)
2-phenyl-4-{[4-(trifluoromethyl)benzyl]oxy}-1,3-thiazole-5-carboxylic acid (55)
2-(3-fluorophenyl)-4-{[4-(trifluoromethyl)benzyl]oxy}-1,3-thiazole-5-carboxylic acid (56)
2-phenyl-4-{[4-(trifluoromethyl)benzoyl]oxy}-1,3-thiazole-5-carboxylic acid (57)
2-(3-fluorophenyl)-4-{[4-(trifluoromethyl)benzoyl]oxy}-1,3-thiazole-5-carboxylic acid (58)
2-(4-methylphenyl)-4-{[4-(trifluoromethyl)benzoyl]oxy}-1,3-thiazole-5-carboxylic acid (59)
4-methoxy-2-(4-methylphenyl)-1,3-thiazole-5-carboxylic acid (60)
2-(4-methylphenyl)-4-(2-methylpropoxy)-1,3-thiazole-5-carboxylic acid (61)
ethyl 4-[(tert-butoxycarbonyl)amino]-2-(4-fluorophenyl)-1,3-thiazole-5-carboxylate (62)
ethyl 4-amino-2-(4-fluorophenyl)-1,3-thiazole-5-carboxylate hydrochloride (63)
ethyl 4-(acetylamino)-2-(4-methylphenyl)-1,3-thiazole-5-carboxylate (64)
ethyl 2-(4-methylphenyl)-4-{[4-(trifluoromethyl)benzoyl]amino}-1,3-thiazole-5-carboxylate (65)
ethyl 2-(4-methylphenyl)-4-[(phenylcarbamoyl)amino]-1,3-thiazole-5-carboxylate (66)
ethyl 4-[(2-aminoethyl)amino]-2-(4-methylphenyl)-1,3-thiazole-5-carboxylate (67)
ethyl 2-(4-chlorophenyl)-4-{[2-(methylamino)ethyl]amino}-1,3-thiazole-5-carboxylate (68)
ethyl 2-(4-chlorophenyl)-4-{[2-(propylamino)ethyl]amino}-1,3-thiazole-5-carboxylate (69)
ethyl 4-[(2-aminoethyl)amino]-2-(4-chlorophenyl)-1,3-thiazole-5-carboxylate (70)
ethyl 4-{[2-(methylamino)ethyl]amino}-2-(4-methylphenyl)-1,3-thiazole-5-carboxylate (71)
ethyl 4-[(2-aminoethyl)amino]-2-[2'-(trifluoromethyl)biphenyl-4-yl]-1,3-thiazole-5-carboxylate (72)
ethyl 4-[(2-aminoethyl)amino]-2-[2'-(trifluoromethyl)biphenyl-3-yl]-1,3-thiazole-5-carboxylate (73)
ethyl 2-(4-chlorophenyl)-4-{[2-(cyclopentylamino)ethyl]amino}-1,3-thiazole-5-carboxylate (74)
ethyl 2-phenyl-4-{[2-(pyrrolidin-1-yl)ethyl]amino}-1,3-thiazole-5-carboxylate (75)
ethyl 4-(benzylamino)-2-(3-fluorophenyl)-1,3-thiazole-5-carboxylate (76)
ethyl 4-[(1,3-benzodioxol-5-ylmethyl)amino]-2-(3-fluorophenyl)-1,3-thiazole-5-carboxylate (77)
ethyl 2-(3-fluorophenyl)-4-[(pyridin-3-ylmethyl)amino]-1,3-thiazole-5-carboxylate (78)
4-[(2-aminoethyl)amino]-2-(4-methylphenyl)-1,3-thiazole-5-carboxylic acid (79)
4-{[2-(methylamino)ethyl]amino}-2-(4-methylphenyl)-1,3-thiazole-5-carboxylic acid (80)
4-[(2-aminoethyl)amino]-2-(3-fluorophenyl)-1,3-thiazole-5-carboxylic acid (81)
sodium 4-[(3-chlorobenzyl)oxy]-2-(3-fluorophenyl)-1,3-thiazole-5-carboxylate (82)
sodium 4-[(4-chlorobenzyl)oxy]-2-(4-methylphenyl)-1,3-thiazole-5-carboxylate (83)
sodium 4-(4-chlorobenzyloxy)-2-(4-chlorophenyl)-1,3-thiazole-5-carboxylate (84)
sodium 4-(2-chlorobenzyloxy)-2-(4-chlorophenyl)-1,3-thiazole-5-carboxylate (85)
sodium 4-(2-chlorobenzyloxy)-2-(4-methylphenyl)-1,3-thiazole-5-carboxylate (86)
sodium 4-(2-chlorobenzyloxy)-2-(3-fluorophenyl)-1,3-thiazole-5-carboxylate (87)
sodium 4-(4-chlorobenzyloxy)-2-(3-fluorophenyl)-1,3-thiazole-5-carboxylate (88)
(1R,2S,5R)-2-isopropyl-5-methylcyclohexyl-4-(benzyloxy)-2-(4-methylphenyl)-1,3-thiazole-5-carboxylate (89)
(1R,2S,5R)-2-isopropyl-5-methylcyclohexyl-4-hydroxy-2-(4-methylphenyl)-1,3-thiazole-5-carboxylate (90)
ethyl 2-(4-chlorophenyl)-4-(methoxymethoxy)-1,3-thiazole-5-carboxylate (91)
2-(4-chlorophenyl)-4-(methoxymethoxy)-1,3-thiazole-5-carboxylic acid (92)
2-(4-chlorophenyl)-4-(methoxymethoxy)-1,3-thiazole-5-carboxamide (93)
2-(4-chlorophenyl)-4-(methoxymethoxy)-1,3-thiazole-5-carbonitrile (94)
2-(4-chlorophenyl)-5-(1H-tetrazol-5-yl)-1,3-thiazol-4-ol (95)
2-(4-chlorophenyl)-5-(1-methyl-1H-tetrazol-5-yl)-1,3-thiazol-4-ol (96)
2-(3-fluorophenyl)-5-(1-methyl-1H-tetrazol-5-yl)-1,3-thiazol-4-ol (97)
2-(4-chlorophenyl)-5-(5-methyl-4H-1,2,4-triazol-3-yl)-1,3-thiazol-4-ol (98)
2-(3-fluorophenyl)-5-(5-methyl-4H-1,2,4-triazol-3-yl)-1,3-thiazol-4-ol (99)
2-(4-chlorophenyl)-5-(5-methyl-1,2,4-oxadiazol-3-yl)-1,3-thiazol-4-ol (100)
2-(3-fluorophenyl)-5-(5-methyl-1,2,4-oxadiazol-3-yl)-1,3-thiazol-4-ol (101)
3-{4-[(4-chlorobenzyl)oxy]-2-(3-fluorophenyl)-1,3-thiazol-5-yl}-5-methyl-1,2,4-oxadiazole (102)
2-(4-chlorophenyl)-5-(5-methyl-1,3,4-oxadiazol-2-yl)-1,3-thiazol-4-ol (103)
2-(3-fluorophenyl)-5-(5-methyl-1,3,4-oxadiazol-2-yl)-1,3-thiazol-4-ol (104)
ethyl 2-(3-fluorophenyl)-4-hydroxy-1,3-oxazole-5-carboxylate (106)
ethyl 4-hydroxy-2-(4-methylphenyl)-1,3-oxazole-5-carboxylate (107)
ethyl 4-[(4-chlorobenzyl)oxy]-2-phenyl-1,3-oxazole-5-carboxylate (108)
ethyl 4-[(4-chlorobenzyl)oxy]-2-(3-fluorophenyl)-1,3-oxazole-5-carboxylate (109)
ethyl 4-[(4-chlorobenzyl)oxy]-2-(4-methylphenyl)-1,3-oxazole-5-carboxylate (110)
ethyl 2-phenyl-4-{[4-(trifluoromethyl)benzoyl]oxy}-1,3-oxazole-5-carboxylate (111)
4-[(4-chlorobenzyl)oxy]-2-phenyl-1,3-oxazole-5-carboxylic acid (112)
4-[(4-chlorobenzyl)oxy]-2-(3-fluorophenyl)-1,3-oxazole-5-carboxylic acid (113)
4-[(4-chlorobenzyl)oxy]-2-(4-methylphenyl)-1,3-oxazole-5-carboxylic acid (114)
2-(3-fluorophenyl)-5-(5-methyl-1,2,4-oxadiazol-3-yl)-1,3-oxazol-4-ol (115)
3-{4-[(4-chlorobenzyl)oxy]-2-(3-fluorophenyl)-1,3-oxazol-5-yl}-5-methyl-1,2,4-oxadiazole (116)
ethyl 2-(3-fluorophenyl)-5-hydroxy-1,3-thiazole-4-carboxylate (117)

2-(3-fluorophenyl)-5-(2-ethyl-2H-tetrazol-5-yl)-1,3-thiazol-4-ol (118).

2. A pharmaceutical composition comprising as the active ingredient at least one compound of claim 1, in combination with pharmaceutically acceptable excipients and/or diluents.

* * * * *

UNITED STATES PATENT AND TRADEMARK OFFICE
CERTIFICATE OF CORRECTION

PATENT NO. : 9,856,246 B2  
APPLICATION NO. : 15/414803  
DATED : January 2, 2018  
INVENTOR(S) : Alessio Moriconi et al.

Page 1 of 1

It is certified that error appears in the above-identified patent and that said Letters Patent is hereby corrected as shown below:

In the Claims

In Claim 1, Column 68, Line 43, delete "ethyl4-(2-" and insert -- ethyl 4-(2- --, therefor.

In Claim 1, Column 70, Line 35, delete "-4-01" and insert -- -4-ol --, therefor.

Signed and Sealed this  
First Day of May, 2018

Andrei Iancu  
*Director of the United States Patent and Trademark Office*